US008389564B2

(12) United States Patent
Macherla et al.

(10) Patent No.: US 8,389,564 B2
(45) Date of Patent: *Mar. 5, 2013

(54) PROTEASOME INHIBITORS

(76) Inventors: Venkat Rami Reddy Macherla, San Diego, CA (US); Barbara Christine Potts, Escondido, CA (US); Rama Rao Manam, San Diego, CA (US); Katherine A. McArthur, La Mesa, CA (US); Ta-Hsiang Chao, San Diego, CA (US); Saskia Theodora Cornelia Neuteboom, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,627

(22) Filed: May 14, 2012

(65) Prior Publication Data
US 2012/0270919 A1 Oct. 25, 2012

Related U.S. Application Data

(60) Continuation of application No. 13/052,827, filed on Mar. 21, 2011, now Pat. No. 8,227,503, which is a division of application No. 12/464,686, filed on May 12, 2009, now Pat. No. 7,910,616.

(60) Provisional application No. 61/052,576, filed on May 12, 2008.

(51) Int. Cl.
 *A61K 31/407* (2006.01)
 *C07D 491/044* (2006.01)
(52) U.S. Cl. ........................................ 514/421; 548/453
(58) Field of Classification Search .................. 514/421; 548/453
See application file for complete search history.

(56) References Cited

U.S. PATENT DOCUMENTS

| 5,445,829 | A | 8/1995 | Paradissis et al. |
| 5,576,012 | A | 11/1996 | Bauer et al. |
| 5,601,845 | A | 2/1997 | Buxton et al. |
| 5,641,515 | A | 6/1997 | Ramtoola |
| 5,653,987 | A | 8/1997 | Modi et al. |
| 5,654,286 | A | 8/1997 | Hostetler |
| 5,667,809 | A | 9/1997 | Trevino et al. |
| 5,683,676 | A | 11/1997 | Akehurst et al. |
| 5,688,529 | A | 11/1997 | Lidgate et al. |
| 5,707,615 | A | 1/1998 | Cardin et al. |
| 5,707,641 | A | 1/1998 | Gertner et al. |
| 5,726,181 | A | 3/1998 | Hausheer et al. |
| 5,733,888 | A | 3/1998 | Carver et al. |
| 5,756,764 | A | 5/1998 | Fenteany et al. |
| 5,874,443 | A | 2/1999 | Kiely et al. |
| 5,886,210 | A | 3/1999 | Rayle et al. |
| 5,922,683 | A | 7/1999 | Or et al. |
| 6,133,308 | A | 10/2000 | Soucy et al. |
| 6,147,223 | A | 11/2000 | Fenteany et al. |
| 6,214,862 | B1 | 4/2001 | Fenteany et al. |
| 6,271,199 | B2 | 8/2001 | Brand et al. |
| 6,294,560 | B1 | 9/2001 | Soucy et al. |
| 6,333,358 | B1 | 12/2001 | Nakazato et al. |
| 6,335,358 | B1 | 1/2002 | Fenteany et al. |
| 6,350,759 | B1 | 2/2002 | Casara et al. |
| 6,458,825 | B1 | 10/2002 | Fenteany et al. |
| 6,500,825 | B2 | 12/2002 | Lan et al. |
| 6,506,787 | B2 | 1/2003 | Fujishita et al. |
| 6,509,331 | B1 | 1/2003 | Audia et al. |
| 6,566,553 | B2 | 5/2003 | Soucy et al. |
| 6,645,999 | B1 | 11/2003 | Schreiber et al. |
| 6,794,516 | B2 | 9/2004 | Soucy et al. |
| 6,838,477 | B2 | 1/2005 | Schreiber et al. |
| 6,849,743 | B2 | 2/2005 | Soucy et al. |
| 7,144,723 | B2 | 12/2006 | Fenical et al. |
| 7,176,232 | B2 | 2/2007 | Fenical et al. |
| 7,176,233 | B2 | 2/2007 | Fenical et al. |
| 7,179,834 | B2 | 2/2007 | Fenical et al. |
| 7,183,417 | B2 | 2/2007 | Corey |
| 7,276,530 | B2 | 10/2007 | Potts et al. |
| 7,371,875 | B2 | 5/2008 | Xiao et al. |
| 7,442,830 | B1 | 10/2008 | Olhava et al. |
| 7,511,156 | B2 | 3/2009 | Corey |
| 7,544,814 | B2 | 6/2009 | Potts et al. |
| 7,572,606 | B1 | 8/2009 | Lam et al. |
| 7,579,371 | B2 | 8/2009 | Palladino et al. |
| 7,635,712 | B2 | 12/2009 | Fenical et al. |
| 7,879,576 | B2 | 2/2011 | Fenical et al. |
| 7,910,616 | B2 | 3/2011 | Macherla et al. |
| 7,928,138 | B2 | 4/2011 | Feling et al. |
| 8,168,803 | B2 | 5/2012 | Palladino et al. |
| 8,217,072 | B2 | 7/2012 | Fenical et al. |
| 8,222,289 | B2 | 7/2012 | Fenical et al. |
| 8,227,503 | B2 * | 7/2012 | Macherla et al. ............. 514/421 |
| 2001/0002391 | A1 | 5/2001 | Brand et al. |
| 2001/0051654 | A1 | 12/2001 | Elliott et al. |
| 2002/0049157 | A1 | 4/2002 | Wu et al. |
| 2002/0068690 | A1 | 6/2002 | Baldwin et al. |
| 2002/0106689 | A1 | 8/2002 | Faustman et al. |
| 2003/0157695 | A1 | 8/2003 | Fenical et al. |
| 2004/0106539 | A1 | 6/2004 | Schubert et al. |

(Continued)

FOREIGN PATENT DOCUMENTS

| CA | 2429163 | 6/2002 |
| WO | WO 96/32105 | 10/1996 |

(Continued)

OTHER PUBLICATIONS

Adams, et al., "Proteasome Inhibitors: A Novel Class of Potent and Effective Antitumor Agents," *Cancer Res.*, (1999) 59:2615-2622.
Adams, J., "The Development of Novel Targeted Therapeutics for Treatment of Multiple Myeloma Research Roundtable," *Euro. J. Haematology*, (2003) 70:265.
Adams, J., "Proteasome Inhibitors as New Anticancer Drugs," *Curr. Opin. Oncol.*, (2002) 14:628-34.
Alessandri, et al., "Mobilization of Capillary Endothelium in Vitro Induced by Effectors of Angiogenesis in Vivo," *Cancer Res.*, (1983) 43(4):1790-1797.
Alm, et al. "Effects of Topically Applied PGF2 and its Isopropylester on Normal and Glaucomatous Human Eyes," *Prog. Clin. Biol. Res.*, (1989) 312:447-58.

(Continued)

*Primary Examiner* — Kristin Bianchi

(57) ABSTRACT

Disclosed herein are compounds of Formula (I) that include a sulfonate ester, ester or ether group. Compounds of Formula (I) can be included in pharmaceutical compositions, and can be used to treating and/or ameliorating a disease or condition, such as cancer, a microbial disease and/or inflammation.

21 Claims, 1 Drawing Sheet

U.S. PATENT DOCUMENTS

| | | |
|---|---|---|
| 2004/0138196 A1 | 7/2004 | Fenical et al. |
| 2005/0049294 A1 | 3/2005 | Palladino et al. |
| 2005/0203029 A1 | 9/2005 | Schubert et al. |
| 2005/0203162 A1 | 9/2005 | Xiao et al. |
| 2005/0239866 A1 | 10/2005 | Fenical et al. |
| 2005/0245435 A1 | 11/2005 | Smyth et al. |
| 2005/0288352 A1 | 12/2005 | Potts et al. |
| 2006/0008852 A1 | 1/2006 | Fenical et al. |
| 2006/0229353 A1 | 10/2006 | Stadler et al. |
| 2006/0264495 A1 | 11/2006 | Palladino et al. |
| 2006/0287520 A1 | 12/2006 | Danishefsky et al. |
| 2007/0004676 A1 | 1/2007 | Palladino et al. |
| 2007/0155815 A1 | 7/2007 | Fenical et al. |
| 2007/0161693 A1 | 7/2007 | Corey |
| 2007/0225350 A1 | 9/2007 | Anderson et al. |
| 2007/0249693 A1 | 10/2007 | Ling et al. |
| 2008/0070273 A1 | 3/2008 | Fenical et al. |
| 2008/0070969 A1 | 3/2008 | Potts et al. |
| 2008/0280968 A1 | 11/2008 | Palladino et al. |
| 2009/0022730 A1 | 1/2009 | Raulf et al. |
| 2009/0036390 A1 | 2/2009 | Anderson et al. |
| 2009/0062547 A1 | 3/2009 | Romo et al. |
| 2009/0069401 A1 | 3/2009 | Fenical et al. |
| 2009/0148445 A1 | 6/2009 | Bonavida et al. |
| 2009/0156469 A1 | 6/2009 | Ghobrial et al. |
| 2009/0197937 A1 | 8/2009 | Fenical et al. |
| 2009/0234137 A1 | 9/2009 | Ling et al. |
| 2009/0298906 A1 | 12/2009 | Macherla et al. |
| 2009/0318529 A1 | 12/2009 | Fenical et al. |
| 2010/0144826 A1 | 6/2010 | Fenical et al. |
| 2010/0168046 A1 | 7/2010 | Palladino et al. |
| 2012/0230972 A1 | 9/2012 | Fenical et al. |

FOREIGN PATENT DOCUMENTS

| | | |
|---|---|---|
| WO | WO 98/35691 | 8/1998 |
| WO | WO 99/09006 | 2/1999 |
| WO | WO 99/15183 | 4/1999 |
| WO | WO 99/22729 | 5/1999 |
| WO | WO 00/23614 | 4/2000 |
| WO | WO 02/47610 | 6/2002 |
| WO | WO 2004/043374 | 5/2004 |
| WO | WO 2004/071382 | 8/2004 |
| WO | WO 2005/002572 | 1/2005 |
| WO | WO 2005/003137 | 1/2005 |
| WO | WO 2006/028525 | 3/2005 |
| WO | WO 2005/094423 | 10/2005 |
| WO | WO 2005/099687 | 10/2005 |
| WO | WO 2006/005551 | 1/2006 |
| WO | WO 2006/060609 | 6/2006 |
| WO | WO 2006/060676 | 6/2006 |
| WO | WO 2006/060809 | 6/2006 |
| WO | WO 2006/060819 | 6/2006 |
| WO | WO 2006/118973 | 11/2006 |
| WO | WO 2007/021897 | 2/2007 |
| WO | WO 2007/033039 | 3/2007 |
| WO | WO 2007/130404 | 11/2007 |
| WO | WO 2007/138116 | 12/2007 |
| WO | WO 2008/124699 | 10/2008 |
| WO | WO 2008/137780 | 11/2008 |
| WO | WO 2009/134531 | 11/2009 |
| WO | WO 2009/140287 | 11/2009 |

OTHER PUBLICATIONS

Ando et al., Silver Fluoride Supported on Calcium Fluoride. Improved Fluorination and Halofluorination Reactions, Chem Lttrs. (1988) 11: 1877-1878.

Andtbacka, et al., "The Proteasome Inhibitor NPI-0052 Sensitizes Pancreatic Cancer Cells to TRAIL In Vitro and In Vivo," Amer. Assoc. Cancer Res., (2005) 46: Abstract #1721.

Andtbacka, et al., "The Proteasome Inhibitor NPI-0052 Overcomes TRAIL Resistance in Human Pancreatic Cancer Cells In Vitro and In Vivo," Cancer Research, (2007) (under revision).

Barral, et al., "The Proteasome Inhibitor NPI-0052 Reduces Tumor Growth and Overcomes Resistance of Prostate Cancer to rhTRAIL via Inhibition of the NF-kB Pathway," Amer. Assoc. Cancer Res., (2007): abstract 1465.

Beers et al. (Eds.), "Bacterial Diseases," *The Merck Manual of Diagnosis and Therapy*, (1999) The Merck Research Laboratories, Whitehouse Station N.J., Section 13, Chapter 157: pp. 1157-1158.

Beers et al. (Eds.), "Parasitic Infections," *The Merck Manual of Diagnosis and Therapy*, (1999) The Merck Research Laboratories, Whitehouse Station N.J., Section 13, Chapter 161: pp. 1241-1252.

Beers et al. (Eds.), *The Merck Manual of Diagnosis and Therapy*, $17^{th}$ Ed. 1999, The Merck Research Laboratories, Whitehouse Station N.J., pp. 397-399, 948-949, 1916-1917, 1974-1975 and 1978-1983.

Beers et al. (Eds.), *The Merck Manual of Diagnosis and Therapy*, $17^{th}$ Ed. 1999, The Merck Research Laboratories, Whitehouse Station N.J., pp. 1193-1201 & 1204.

Beers, et al. (Eds), "The Merck Manual of Diagnosis and Therapy", $17^{th}$ Ed. 1999, The Merck Research Laboratories, Whitehouse Station N.J., pp. 1085-1088, 1101-1135, and 1237-1276.

Bernan, et al., "Marine Microorganisms as a Source of New Natural Products," *Advances in Applied Microbiology*, (1997) 43:57-90.

Bhalla, et al., "High-Dose Mitoxantrone Induces Programmed Cell Death or Apoptosis in Human Myeloid Leukemia Cells," *Blood*, (1993) 82(10):3133-3140.

Bicknell, et al. (Eds.), *Tumour Angiogenesis*, Oxford University Press, New York (1997), Table of Contents, pp. 5.

Blum, et al., "Adriamycin: A New Anticancer Drug with Significant Clinical Activity," *Ann Intern Med*, (1974) 80(2):249-259.

Blunt, et al., << Marine Natural Products,>> *Nat. Prod. Rep.*, (2003) 20:1-48.

Bodart, et al., "Anthrax, MEK and Cancer," *Cell Cycle*, (2002) 1:10-15.

Bradley, et al., "Identification of the Cellular Receptor for Anthrax Toxin," *Nature*, (2001) 414:225-229.

Brosius, et al., "Complete nucleotide sequence of a 16S ribosomal RNA gene from *Eschericia coli*," *Biochemistry*, (1978) 75(10)4801-4805.

Bull, et al., "Search and Discovery Strategies for Biotechnology: the Paradigm Shift," *Microbiol. Mol. Biol. Rev.*, (2000) 64(3):573-606.

Carey, Francis, *Organic Chemistry*, $2^{nd}$ ed., McGraw Hill, Inc., New York (1992), pp. 328-331.

Chao et al., "Leaving Groups Extend the Duration of Proteasome Inhibition and Enhance the Potency of Salinosporamides", Nereus Pharmaceuticals, Inc. Release (Feb. 2008), Poster circulated at Marine Natural Products Gordon Research Conference, Ventura, CA, 1 page.

Chatterjee, et al., "RKIP Sensitizes Prostate and Breast Cancer Cells to Drug-induced Apoptosis" *The Journal of Biological Chemistry* (2004) 279(14):17515-17523.

Chauhan, et al., "A Novel Orally Available Proteasome Inhibitor NPI-0052 Induces Killing in Multiple Myeloma (MM) Cells Resistant to Conventional and Bortezomib Therapies," *Blood*, (2004) 104(11): 2405.

Chauhan, et al., "A Novel Orally Active Proteasome Inhibitor Induces Apoptosis in Multiple Myeloma Cells with Mechanisms Distinct from Bortezomib," *Cancer Cell*, (2005) 8:407-419.

Chauhan, et al., "A Novel Proteasome Inhibitor NPI-0052 as an Anticancer Therapy," *British Journal of Cancer*, (2006) 95(8):961-965.

Cheng, et al., "Arenaric Acid, a New Pentacyclic Polyether Produced by a Marine Bacterium (Actinomycetales)", *J. Nat. Prod.*, (1999) 62:605-607.

Cheng, et al., "Luisols A and B, New Aromatic Tetraols Produced by an Estuarine Marine Bacterium of the Genus *Streptomyces* (Actinomycetales)," *J. Nat. Prod.*, (1999) 62:608-610.

Chow, et al., "Anti-CD20 antibody (IDEC-C2B8, rituximab) Enhances Efficacy of Cytotoxic Drugs on Neoplastic Lymphocytes in vitro: Role of Cytokines, Complement, and Caspases" *Haematologica* (2002) 87:33-43.

Ciechanover, et al., (Eds.) "The Ubiquitin-Proteasome Proteolytic System—From Classical Biochemistry to Human Diseases" by Baumeister et al., (2002) pp. 68-70.

Claverol, et al., "Mapping and Structural Dissection of Human 20 S Proteasome Using Proteomic Approaches," *Mol Cell Proteomics*, (2002) 1:567-78.

Cole, et al., "The Ribosomal Database Project (RDP-II): sequences and tools for high-throughput rRNA analysis," *Nucleic Acids Research*, (2005) 33: D294-D296.

Colquhoun, et al, "Rapid Characterization of Deep-Sea Actionmycetes for Biotechnology Screening Programmes", *Antonie Van Leeuwenoek*, (2000) 77:359-367.

Colquhoun, et al., "Novel Rhodococci and Other Mycolate Actinomycetes From the Deep Sea," *Antonie van Leeuwenhoek*, (1998) 74:27-40.

Colquhoun, et al., "Taxonomy and Biotransformation Activites of Some Deep-Sea Actinomycetes," *Extremophiles*, (1998) 2:269-277.

Corey et al. "The Structural Requirements for Inhibition of Proteasome Function by the Lactacystin-derived beta-lactone and Synthetic Analogs," *Tetrahedron* (1999) 55(11):3305-3316.

Corey, et al., "Total Synthesis of Lactacystin," *J. Am. Chem. Soc.*, (1992) 114(26):10677-10678.

Corey, et al., "An Efficient Total Synthesis of a New and Highly Active Analog of Lactacystin," *Tetrahedron Letters*, (1998) 39:7475-7478.

Cragg, et al. "Chemical Diversity: A Function of Biodiversity," *Trends Pharmacol. Sci.*, (2002) 23:404-5.

Crane, et al., "A Novel Enantioselective Synthetic Route to Omuralide Analogues with the Potential for Species Selectivity in Proteasome Inhibition," *Organic Letters*, (2001) 1395-1397.

Crueger, et al. (Eds.), *Biotechnology: A Textbook of Industrial Microbiology*, 2nd ed. (English Edition, Thomas D. Brock Ed.), Sinauer Associates Inc, Sunderland MA, (1990) Chapter 2:4-8.

Cusack, et al. "Enhanced Chemosensitivity to CPT-11 with Proteasome Inhibitor PS-341: . Implications for Systemic Nuclear Factor-kB Inhibition", *Cancer Res.*, (May 1, 2001) 61(9):3535-40.

Cusack, et al., "NPI-0052 Enhances Tumoricidal Response to Conventional Cancer Therapy in a Colon Cancer Model," *Clin. Cancer Res.*, (2006) 22:6758-6764.

Cusack, et al., "Rationale for the Treatment of Solid Tumors with the Proteasome Inhibitor Bortezomib," *Cancer Treat Rev.*, (2003) 29(suppl 1): 21-31.

Cusack, et al., "Oral proteasome inhibitor (NPI-0052) enhances sensitivity to combination Gemcitabine and Erbitux in a pancreatic cancer xenograft model," Nereus Pharmaceuticals, Inc., (Apr. 19, 2005), abstract 4943 for presentation at the American Association of Cancer Research Annual Meeting held on Apr. 19, 2005 in Orange County, CA, 1 pages.

Davidson, Bradley S., "New Dimensions in Natural Products Research: Cultured Marine Microorganisms," *Current Opinion in Biotechnology*, (1995) 6:284-291.

Decker, et al., "Inhibition of Caspase-3-mediated Poly(ADP-ribose) Polymerase (PARP) Apoptotic Cleavage by Human PARP Autoantibodies and Effect on Cells Undergoing Apoptosis," *J. Biol. Chem.*, (2000) 275(12):9043-9046.

DeLong, et al. "Environmental Diversity of Bacteria and Archaea," *Syst. Biol.*, (2001) 50(4):470-478.

Developmental Therapeutics Program—NCI/NIH, "DTP Human Tumor Cell Line Screen." Screening Services. DPI. Sep. 28, 2005 http://dtp.nci.nih.gov/branches/btb/ivclsp.html.

Developmental Therapeutics Program—NCI/NIH, "Cell Lines in the in Vitro Screen", online: http://dtp.nci.nih.gov/docs/misc/common_files/cell_list/html, accessed Oct. 27, 2009.

Dick, et al., "Mechanistic Studies on the Inactivation of the Proteasome by Lactacystin," *J. Biol. Chem.*, (1996) 271(13):7273-7276.

Ding, et al., "Proteasome Inhibition Induces Reversible Impairments in Protein Synthesis," *The FASEB Journal.*, (2006) 20:1055-1063.

Duesbery, et al., "Proteolytic Inactivation of MAP-Kinase-Kinase by Anthrax Lethal Factor," *Science*, (1998) 280:734-737.

Elliott, et al. "The Proteasome: A New Target for Novel Drug Therapies," *American Journal of Clinical Pathology*, (Nov. 2001) 637-646.

Elliott, et al., "Proteasome Inhibition: A New Anti-Inflammatory Strategy," *J. Mol. Med.*, (2003) 81:235-245.

Endo, et al., "Total Synthesis of Salinosporamide A," *J. Am. Chem. Soc.*, (2005) 127(23): 8298-8299 and Supporting Information S1-S23.

Erba, et al., "Mode of Action of Thiocoraline: A Natural Marine Compound With Anti-Tumor Activity," *British Journal of Cancer*, (1999) 88(7):971-980.

Escuyer, et al., "Anthrax Protective Antigen Interacts with a Specific Receptor on the Surface of CHO-K1 Cells," *Infect. Immun.*, (1991) 59(10):3381-3386.

Faulkner, D. John, "Marine Natural Products," *Nat. Prod. Rep.*, (2001) 18(1):1-49.

Feling, et al. "Salinosporamide A: A Highly Cytotoxic Proteasome Inhibitor from a Novel Microbial Source, a Marine Bacterium of the New Genus Salinospora," *Angew. Chem. Int. Ed.*, (2003) 42(3):355-357.

Fenical, et al., "Discovery and Development of the Anticancer Agent Salinosporamide A (NPI-0052)," *Bioorganic & Med. Chem.*, (2009) 17:2175-2180.

Fenical, et al., "Marine Microorganisms as a Biomedical Source: Are They Unculturable or Uncultured?" PowerPoint Presentation, Center for Marine Biotechnology and Biomedicine (Feb. 24, 2002).

Fenical, et al., "Marine Microorganisms as a Developing Resource for Drug Discovery," *Pharmaceutical News*, (2002) 9:489-494.

Fenical, et al., "Salinospora, a Major New Marine Actinomycete Taxon for Drug Discovery," Powerpoint Presentation, Center for Marine Biotechnology and Biomedicine (Jun. 24, 2001).

Fenical, William, "Chemical Studies of Marine Bacteria: Developing a New Resource," *Chem. Rev.*, (1993) 93(5):1673-1683.

Fenical, William, "New Pharmaceuticals From Marine Organisms," *Marine Biotechnology*, (1997) 15:339-341.

Fenteany, et al., "Lactacystin, Proteasome Function, and Cell Fate," *J. Biol. Chem.* (1998) 273(15): 8545-8548.

Fenteany, et al., "Inhibition of Proteasome Activities and Subunit-Specific Amino-Terminal Threonine modification by Lactacystin," *Science*, (1995) 268:726-731.

Fernandez-Chimeno, et al., "IB-96212, a Novel Cytotoxic Macrolide Produced by a Marine *Micromonospora*," *Journal of Antibiotics*, (2000) 53(5):474-478.

Fingl, et al., "General Principals," *The Pharmaceutical Basis of Therapeutics*, 5th Ed., (Goodman et al. Eds., 1975), MacMillan Publishing Co. Inc., New York, Chapter 1:1-46.

Folkman, Judah, "Angiogenesis-Dependent Diseases," *Seminars in Oncology*, (Dec., 2001) 28:536-542.

Folkman, Judah, "Tumor Angiogenesis," *Adv Cancer Res.*, (1985) 43:175-203.

Fukuchi, et al., "Direct proteasome inhibition by clasto-lactacystin β-lactone permits the detection of ubiquitinated p21 in ML-1 Cells," *Biochem. Biophys. Acta*, (1999) 1451:206-210.

Gale, et al. (Eds.), *The Molecular Basis of Antibiotic Action*, 2nd ed., John Wiley and Sons, London (1981) Table of Contents, pp. 1-13.

Gantt, et al., "Proteasome Inhibitors Block Development of Plasmodium SPP", *Antimicrobial Agents and Chemotherapy*, (1998) 2731-2738.

Geier, et al., "A Giant Protease with Potential to Substitute for Some Functions of the Proteasome," *Science*, (1999) 283:978-981.

Gennaro, A.R. (Ed.), *Remington's Pharmaceutical Sciences*, 17th Ed., Mack Publishing Co., Easton, PA, (1985), Table of Contents, pp. 5.

Gennaro, A.R. (Ed.), *Remington's Pharmaceutical Sciences*, 18th Ed., Mack Publishing Co., Easton, PA (1990), Table of Contents, pp. 5.

Giannangeli et al., "Effect of Modifications of the Alkylpiperazine Moiety of Trazodone on $5HT_{2A}$ and $a_1$ Receptor Binding Affinity," *J. Med. Chem.*, (1999) 42(3):336-45.

Giovannoni, Stephen, "Oceans of Bacteria," *Nature*, (Jul. 29, 2004) 430:515-16.

Goldberg, et al., "Not Just Research Tools—Proteasome Inhibitors Offer Therapeutic Promise," *Natural Medicine*, (2002) 338-40.

Golub, et al., "Molecular Classification of Cancer; Class Discovery and Class Prediction by Gene Expression Monitoring", *Science*, (1999) 286:531-37.

Goodfellow, et al., "Actinomycetes in Biotechnology," *Search and Discovery of New Antibiotics*, Okami, et al., eds., Academic Press, San Diego, (1988) Chapter 2:33-67.

Goodfellow, et al., "Actinomycetes in Marine Sediments," *Biological Biochemical and Biomedical Aspects of Actinomycetes*, Ortiz-Ortiz, et al., eds., Academic Press, Inc., Orlando (1984) 453-72.

Goodfellow, et al., "Ecology of Actinomycestes," *Ann. Rev. Microbiol.*, (1983) 37:189-216.

Goodfellow, et al., "Search and Discovery of Industrially Significant Actinomycetes," *Microbial Products: New Approaches, Society for General Microbiology Symposium*, (1989) 44:343-83.

Grant, et al., "Intracellular Mechanisms Involved in Basement Membrane Induced Blood Vessel Differentiation in Vitro," *In Vitro Cell Dev. Biol.*, (1991) 27A:327-36.

Greene et al., *Protective Groups in Organic Synthesis*, 3. Ed., John Wiley & Sons, 1999.

Grosios, et al., "Angiogenesis Inhibition by the Novel VEGF Receptor Tyrosine Kinase Inhibitor; PTK787/ZK222584, Causes Significant Anti-Arthritic Effects in Models of Rheumatoid Arthritis," *Inflamm Res*, (2004) 53: 133-142.

Hanna, et al., "On the Role of Macrophages in Anthrax," *Proc. Natl. Acad. Sci. USA*, (1993) 90:10198-10201.

Hardt, et al., "Neomarinone, and New Cytotoxic Marinone Derivatives, Produced by a Marine Filamentous Bacterium (Actinomycetales)," *Tetrahedron Letters*, (2000) 41(13):2073-2076.

Harker, et al., "Multidrug Resistance in Mitoxantrone-Selected HL-60 Leukemia Cells in the Absence of P-Glycoprotein Overexpression", *Cancer Res.*, (1989) 49(16): 4542-4549.

He, et al., "Lomaiviticins A and B, Potent Antitumor Antibiotics from *Micromonospora lomaivitiensis*," *J. Am. Chem. Soc.*, (2001) 123(22):5362-5363.

Helmke, et al., "*Rhodococcus marinonascens* sp. nov.: An Actinomycete From the Sea," *International J. of Systematic Bacteriology*, (Apr. 1984) 34(2):127-138.

Hideshima, et al., "NF-κβ as a Therapeutic Target in Multiple Myeloma," *J. Biol. Chem.*, (2002) 277(19):16639-16647.

Higuchi, et al., "Pro-Drugs as Novel Delivery Systems," vol. 14, A.C.S. Symposium Series *American Chemical Society*, Atlantic City, NJ., Sep. 10, 1974, (1975) Table of Contents, pp. 3.

Hogan, et al., "Proteasome Inhibition by a Totally Synthetic β-Lactam Related to Salinosporamide A and Omuralide," *J. Am. Chem. Soc.*, (2005) 127(44):15386-15387.

Hopwood, et al., "Genetic Manipulation of Streptomyces Polyketide Synthase Genes for Novel Secondary Metabolite Production," *FEMS Microbiology Reviews*, (1995) 16:233-234.

Horan, Ann C., "Aerobic Actinomycetes: A Continuing Source of Novel Natural Products," *The Discovery of Natural Products with Therapeutic Potential (Biotechnology)*, Vincent P. Gullo (Ed.), Butterworth-Heinemann, Boston (1994) Chapter 1: 1-30.

Hull, et al., "Antiangiogenic Agents Are Effective Inhibitors of Endometriosis," *J. Clinical Endocrinology Metabolism*, (2003) 88:2889-2899.

Jensen, et al., "Distribution of Actinomycetes in Near-Shore Tropical Marine Sediments," *Applied and Environmental Microbiology*, (Apr. 1991) 57(4):1102-1108.

Jensen, et al., "Strategies for the Discovery of Secondary Metabolites from Marine Bacteria: Ecological Perspectives," *Annu. Rev. Microbiology*, (1994) 48:559-584.

Jensen, et al., "The Relative Abundance and Seawater Requirements of Gram-Positive Bacteria in Near-Shore Tropical Marine Samples," *Microbial Ecology*, (1995) 29(3):249-257.

Jensen, et al., "Marine Microorganisms and Drug Discovery: Current Status and Future Potential," *Drugs from the Sea*, Nobuhiro Fusetani Ed., Krager, Basel Switzerland (2000) 6-29.

Jia et al., "The Proteasome Inhibitor NPI-0052 in Combination with Bortezomib Induces Antitumor Activity in Waldenstrom Macroglobulinemia," Blood ASH Annual Meeting Abstracts (Nov. 2006) 108: Abstract 4746.

Jiang, et al., "Antinoflavoside, A Novel Flavonoid-Like Glycoside Produced by a Marine Bacterium of the Genus Streptomyces," *Tetrahedron Letters*, (1997) 38(29):5065-5068.

Johnson et al., "Relationships between drug activity in NCI preclinical in vitro and in vivo models and early clinical trials", *British J Cancer*, (2001) 84(11): 1424-1431.

Joseph, et al., "Laboratory Cultivation of Widespread and Previously Uncultured Soil Bacteria," *Applied and Environmental Microbiology*, (2003) 69(12):7210-7215.

Joshi, A., "Microparticulates for Ophthalmic Drug Delivery," *J. Ocul. Pharmacol.*, (1994) 10:29-45.

Kalns, et al., "Delayed Treatment With Doxycycline Has Limited Effect on Anthrax Infection in BLK57/B6 Mice," *Biochem. Biophys. Res. Commun.*, (2002) 297:506-509.

Kalns, et al., "TNF Receptor 1, IL-1 Receptor, and iNOS Genetic Knockout Mice Are Not Protected from Anthrax Infection," *Biochem. Biophys. Res. Commun.*, (2002) 292:41-44.

Kerr, et al., "Marine Natural Products as Therapeutic Agents", Exp. Opinion on Therapeutic Patents, (1999) 9(9):1207-1222.

Khanbolooki, et al., "Novel NFκβ inhibitors NPI-1342/NPI-1387 and proteasome inhibitor NPI-0052 overcome resistance of pancreatic carcinoma to rhTRAIL," Nereus Pharmaceuticals, Inc., (Apr. 2, 2006), abstract 780 for presentation at the American Association of Cancer Research Annual Meeting held on Apr. 2, 2006 in Washington, D.C., 1 page.

Kim, et al., "Sensitizing Anthrax Lethal Toxin-Resistant Macrophages to Lethal Toxin-Induced Killing by Tumor Necrosis Factor," *J. Biol. Chem.*, (2003) 278:7413-7421.

King, et al., "How Proteolysis Drives the Cell Cycle," *Science*, (1996) 274:1652-1659.

Kisselev, et al., "Proteasome Inhibitors: From Research Tools to Drug Candidates," *Chem. Biol.*, (2001) 8:739-758.

Kisselev et al., "Importance of the Different Proteolytic Sites of the Proteasome and the Efficacy of Inhibitors Varies with the Protein Substrate," J Bio Chem., (Mar. 2006) 281(13): 8582-8590.

Koch, et al., "16S Ribosomal DNA Analysis of the Genera *Micromonospora, Actinoplanes, Catellatospora, Catenuloplanes, Dactylosporangium,* and *Pillimelia* and Emendation or the Family *Micromonosporaceae,*" *Intl Journal of Systematic Bacteriology*, (Jul. 1996) 46(3):765-768.

Kozlowski, et al., "Lactacystin Inhibits Cathepsin A Activity in Melanoma Cell Lines," *Tumor Biol.*, (2001) 22:211-215.

Lacy, et al. "Mapping the Anthrax Protective Antigen Binding Site on the Lethal and Edema Factors," *J. Biol. Chem.*, (2002) 277:3006-3010.

Lala et al., "Role of nitric oxide in tumor progression: lessons from experimental tumors", Cancer Metastasis Rev. (1998) 17(1):91-106.

Lam, et al. "Isolation of a Bromo Analog of Rebeccamycin From *Saccharothrix aerocolonigenes*," *J. Antibiotics*, (Sep. 1991) 44(9):934-939.

Lam, et al., "Production Isolation and Structure Determination of Novel Fluoroindolocarbazoles from *Saccharothrix aerocolonigenes* ATCC 39243," *J. Antibiotics*, (2001) 54(1):1-9.

Lawley, et al., "Induction of Morphologic Differentiation of Endothelial Cells in Culture," *J. Investigative Dermatology*, (Aug. 1989) 93(2 Supplement):59S-61S.

Lenz, et al., "Clinical Update: Proteasome Inhibitors in Solid Tumors", *Cancer Treatment Reviews*, (2003) 29 (1 Supplement):41-48.

Lightcap, et al., "Proteasome Inhibition Measurements Clinical Application," *Clin. Chem.*, (2000) 46(5):673-683.

Lin, et al. "Cytotoxic Effects of Anthrax Lethal Toxin on Macrophage-Like Cell Line J774A.1," *Curr. Microbiol.*, (1996) 33:224-227.

Liu, et al., "Angiogenesis Inhibitors May Regulate Adiposity," *Nutr. Rev.*, (2003) 61:384-387.

Liu, et al. "Precursor Supply for Polyketide Biosynthesis: The Role of Crotonyl-CoA Reductase," *Metab. Eng.*, (2001) 3:40-48.

Macherla, et al., "Structure-Activity Relationship Studies of Salinosporamide A (NPI-0052), a Novel Marine Derived Proteasome Inhibitor," *J. Med. Chem.*, (2005) 48(11): 3684-3687.

Manam, et al., "Stereoselective Enzymatic Reduction of Keto-Salinosporamide to (−)- salinosporamide A (NPI-0052)," *Tetra. Lettr.*, (2007) 48: 2537-2540.

Manam et al., Leaving Groups Prolong the Duration of 20S Proteasome Inhibition and Enhance the Potency of Salinosporamide, J Med Chem., (Oct. 2008) 51(21): 6711-6724.

Manchand, et al., "Syntheses of the Anti-AIDS Drug 2',3'-Dideoxycytidine from Cytidine," *J. Org. Chem.*, (1992) 57:3473-3478.

Mayer, et al., "Efficacy of a Novel Hydrogel Formulation in Human Volunteers," *Ophthalmologica*, (1996) 210(2):101-103.

Mayer, et al., "Marine Pharmacology in 1999: Antitumor and Cytotoxic Compounds," *Anticancer Res.*, (2001) 21:2489-2500.

McMurry, John, *Organic Chemistry*, 5th ed., Brooks/Cole, Pacific Grove, CA. (2000), Chapter 11.5, pp. 398-408.

Mcomie, *Protective Groups in Organic Chemistry*, Plenum Press, 1973.

Meng, et al., "Eponemycin Exerts its Antitumor Effect Through the Inhibition of Proteasome Function," *Cancer Res.*, (1999), 59(12):2798-2801.

Meng, et al., "Epoxomicin, a Potent and Selective Proteasome Inhibitor, Exhibits In Vivo Anti-Inflammatory Activity," *Proc. Natl. Acad. Sci. USA*, (Aug. 1999) 96:10403-10408.

Merriam-Webster Online Dictionary, "Heteroatom", 2010, Merriam-Webster Online, accessed Jun. 16, 2010, http://merriam-webster.com/dictionary/heteroatom.

Min, et al., "Urokinase Receptor Antagonists Inhibit Angiogenesis and Primary Tumor Growth in Syngeneic Mice," *Cancer Res.*, (May 15, 1996) 56(10):2428-2433.

Mincer, et al., "Widespread and Persistent Populations of a Major New Marine Actinomycete Taxon in Ocean Sediments," *Applied and Environmental Microbiology*, (Oct. 2002) 68(10):5005-5011.

Mogridge, et al., "Stoichiometry of Anthrax Toxin Complexes," *Biochemistry*, (2002) 41:1079-1082.

Momose, et al., "2(3H)-and 2(5H)-Furanones. VII. Chirality Transfer on the Tetronic Acid Templates," *Heterocycles*, (1999) 51(6):1321-1343.

Moore, B.S., "Biosynthesis of Marine Natural Products: Microorganisms and Macroalgae," *Nat. Prod. Rep.*, (1999) 16(6):653-674.

Moran, et al., "Evidence for Indigenous Streptomyces Populations in Marine Environment Determined with a 16S rRNA Probe," *Applied and Environmental Microbiology*, (Oct. 1995) 61(10):3695-3700.

Mordenti, et al., "Intracular Pharmacokinetics and Safety of a Humanized Monoclonal Antibody in Rabbits after Intravitreal Administration of a Solution or a PLGA Microsphere Formulation," *Toxicol. Sci.*, (1999) 52(1):101-106.

Mousa, et al., "Angiogenesis Inhibitors: Current & Future Directions," *Current Pharmaceutical Design*, (2004) 10:1-9.

Mulholland et al., "A Concise Total Synthesis of Salinosporamide A," *Org. Biomol. Chem.*, (2006) 4: 2845-6.

Murray, J. Clifford (Ed.), *Angiogenesis Protocols (Methods in Molecular Medicine)*, Humana Press, Totowa, NJ. (2001) Table of Contents, p. 4.

Mutomba, et al., "Inhibition of Proteasome Activity Blocks Cell Cycle Progression at Specific Phase Boundaries in African Trypanosomes", *Mol. Biochem. Parasitology*, (1997) 90:491-504.

NCBI website, sequence for AB242910, http://www.ncbi.nlm.nih.gov/entrez/viewer.fcgi?db=nucleotide&val=124300751, 2 pages, downloaded Feb. 15, 2007, 2 pages.

NCBI website, sequence for EF105548, http://www.ncbi.nlm.nih.gov/entrez/viewer.fcgi?db=nucleotide&val=118640518, 2 pages, downloaded Feb. 15, 2007, 2 pages.

NCBI website, Sequence for EF191171, http://www.ncbi.nlm.nih.gov/entrez/viewer.fcgi?db=nucleotide&val=124014014, 2 Pages, downloaded Feb. 15, 2007, 2 pages.

Nesterneko, et al., "*Rhodococcus luteus* nom. nov., and *Rhodococcus maris* nom. nov.", *Int'l Journal of Systematic Bacteriology*, (Jan., 1982) 32(1):1-14.

Newton. "Il fondo agli oceani potenti antibiotici e anticancro." www.newton.rcs.it/PrimoPiano/News/2003/02_Febbraio/03/Antobiotico.html. (Feb. 2, 2003) 1 page.

Nicholson, D.W., "ICE/CED 3-Like Proteases as Therapeutic Targets for the Control of Inappropriate Apoptosis," *Nat. Biotechnology*, (1996) 14:297-301.

Nicolaus B.J. R. "Symbiotic Approach to Drug Design," *Decision Making in Drug Research*, (1983) 173-186.

Nicosia, et al., "Growth of Microvessels in Serum-Free Matrix Culture of Rat Aorta: A Quantitative Assay of Angiogenesis In Vitro," *Laboratory Investigation*, (Jul. 1990) 63(1):115-122.

Nolan, et al., "Isolation and Screening of Actinomycetes," *Actinomycetes in Biotechnology*, (1988) Chapter 1:1-32.

O'Donnel, Anthony G., "Recognition of Novel Actinomycetes," *Actinomycetes in Biotechnology*, Academic Press, (1988) Chapter 3:69-88.

Ogiso, et al., "Proteosome Inhibition Circumvents Solid Tumor Resistance to Topoisomerase II-directed Drugs," *Cancer Research*, (2000) 60:2429-2434.

Oikawa, et al., "Angiogenic Factor of a Rat Mammary Tumor Cell Line (RMT-1) (I). Secretion of Two Distinct Angiogenic Factors into Serum-Free Conditioned Medium by RMT-1 Cells," *Cancer Letters*, (1991) 59:57-66.

Okami, et al., "Search and Discovery of New Antibiotics", Actinomycetes in Biotechnology, Academic Press (1988) Chapter 2:33-67.

Okami, Y., "The Search for Bioactive Metabolites from Marine Bacteria," *J. Marine Biotechnology*, (1993) 1: 59-65.

Omura, et al., "Lactacystin, A Novel Microbial Metabolite, Induces Neuritogenesis of Neuroblastoma Cells," *J. Antibiotics*, (1991) 44(1): 113-116.

O'Neil et al. eds., "The Merck Index," 13th Ed. 2001, Merck Research Laboratories, Whitehouse Station N.J., pp. THER-5-THER-7.

Online URL:http://aidsinfo.nih.gov/DrugsNew/DrugDetailNT.aspx?Menultem=Drugs&Search=On&int_id=244; pp. 1-2.

Online URL:http://web.archive.org/web/20060117081111/hivhep.tempdomainname.com/hiv and aids/norvir effects . . . Nov. 22, 2010. 1 page.

Online URL:http://en.wikipedia.org/wiki/Myeloma; pp. 1-8.

Online URL:http://en.wikipedia.org/wiki/Sarcoma; pp. 1-2.

Online www.netdoctor.co.uk "Isoniazid: Treatment of Tuberculosis", [accessed on Apr. 8, 2008] pp. 1-2.

Ostrowska, et al., "Lactacystin, A Specific Inhibitor of the Proteasome, Inhibits Human Platelet Lysosomal Cathepsin A-like Enzyme," *Biochem. Biophys. Res. Commun.*, (1997) 234:729-732.

Ostrowska, et al., "Separation of Cathepsin A-like Enzyme and the Proteasome: Evidence that Lactacystin/β-Lactone is not a Specific Inhibitor of the Proteasome," *Int. J. Biochem. Cell Biol.*, (2000) 32:747-757.

Otoguro, et al., "An ntergrated method for the enrichment and selective isolation of *Actinokineospora* spp. in soil and plant litter," *J. Appl. Microbiol.*, (2001) 92:118-130.

Pagano, et al., "Role of the Ubiquitin-Proteasome Pathway in Regulating Abundance of the CyclinDependent Kinase Inhibitor p27," *Science*, (1995) 269(5224):682-685.

Page, Roderic D.M., "TreeView: An Application to Display Phylogenetic Trees on Personal Computers," *Computer Applications in the Biosciences*, (1996) 12:357-358.

Painter, Robert B., "Inhibition of DNA Replicon Initiation by 4-Nitroquinoline 1-Oxide, Adriamycin, and Ethyleneimine," *Cancer Res.*, (1978) 38(12):4445-4449.

Palayoor, et al., "Constitutive Activation of IκB Kinase α and NF-κB in Prostate Cancer Cells is Inhibited by Ibuprofen," *Oncogene*, (1999) 18:7389-7394.

Peckham et al. (Eds.), "The Oxford Textbook of Oncology," *Oxford University Press*, Oxford (1995) vol. 1:447-453.

Pieters et al., "Microbiology: Chemical Warfare and Mycobacterial Defense", *Science*, (Dec. 2003) 302:1900-1902.

Plunkett, et al., "Methods in Laboratory Investigation: An In Vivo Quantitative Angiogenesis Model Using Tumor Cells Entrapped in Alginate," *Laboratory Investigation*, (Apr. 1990) 62(4):510-517.

Prudhomme et al., "Marine Actinomycetes: A New Source of Compounds against the Human Malaria Parasite," Plos One, (2008) 3(6): 1-8.

Qureshi, et al., "The Proteasome as a Lipopolysaccharide-Binding Protein in Macrophages: Differential Effects of Proteasome Inhibition on Lipopolysaccharide-Induced Signaling Events," *J. Immunol.*, (2003) 171(3):1515-1525.

Rappe, et al., "Cultivation of the Ubiquitous SAR11 Marine Bacterioplankton Clade," *Nature*, (Aug. 8, 2002) 418:630-633.

Reddy, et al., "A Simple Stereocontrolled Synthesis of Salinosporamide A," *J. Am. Chem. Soc.*, (2004) 126(20):6230-6231.

Reed et al., "Salinosporamides D-J from the Marine Actinomycete *Salinispora tropica*, Bromosolinosporamide, and Thioester Derivatives Are Potent Inhibitors of the 20S Proteasome", *J Nat Prod.*, (2007) 70: 269-276.

Riva, S., "Biocatalytic Modification of Natural Products," *Curr. Opin. Chem. Biol.*, (2001) 5:106-111.

Roccaro, et al., "Dual Targeting of the Proteasome Regulates Survival and Homing in Waldenstrom Macroglobulinemia." Blood, (Mar. 2008) 111(9): 4752-4763.

Roche, Edward B. (Ed.), "Bioreversible Carriers in Drug Design: Theory and Application," Pergamon Press, Elmsford, NY (1987), pp. 14-21.

Rockwell, et al., "Proteasome Inhibition in Neuronal Cells Induces a Proinflammatory Response Manifested by Upregulation of Cyclooxygenase-2, Its Accumulation as Ubiquitin Conjugates, and Production of the Prostaglandin $PGE_2$," *Arch. Biochem. and Biophysics*, (2000) 374(2):325-333.

Romero, et al., "Thiocoraline, a New Depsipeptide with Antitumor Activity Produced by a Marine *Micromonospora*," *J. Antibiotics*, (1997) 50(9):734-737.

Rubanyi, Gabor M., "Angiogenesis in Health and Disease: Basic Mechanisms and Clinical Applications", *Marcel Dekker*, New York, NY (1999) pp. 6 Content Pages Only.

Ruiz, et al., "The Proteasome Inhibitor NPI-0052 is a More Effective Inducer of Apoptosis than Bortezomib in Lymphocytes from Patients with Chronic Lymphocytic Leukemia," *Mol. Cancer Ther.*, (2006) 5(7): 1836-1843.

Sapi, et al., "Simple and Condensed β-Lactam. Part 32. Base- and Acid-Catalyzed Ring Expansions of 3-Substituted 4-Acetylazetidin-2-ones and Related Compounds". *Collect. Czech. Chem. Commun.* (1999) 64(2):190-202.

Saravanan, et al., "A Short, Stereocontrolled, and Practical Synthesis of α-Methylomuralide, a Potent Inhibitor of Proteasome Function," *J. Org. Chem.*, (2003) 68(7):2760-2764.

Sausville et al., "Contributions of human tumor xenografts to anticancer drug development", *Cancer Res.* (2006) 66(7): 3351-3354.

Schiewe, H. (Reprint) Haustedt, et al., "Rational approaches to natural-product-based drug design", *Curr Opin Drug Disc Devel.* (2006) 9(4):445-462.

Schnaper, et al., "Plasminogen Activators Augment Endothelial Cell Organization in Vitro by Two Distinct Pathways," *J. Cell. Physiol.*, (1995) 165:107-118.

Shadomy, et al., "Antimycotic and Antirickettsial," *Antibiotics, Chemotherapeutics, and Antibacterial Agents for Disease Control*, Martin Grayson (Ed.) *John Wiley and Sons*, New York (1982) 371-395.

Shah, et al., "Early Clinical Experience With the Novel Proteasome Inhibitor PS-519," *J. Clin. Pharmacol.*, (2002) 54:269-276.

Shedden, et al., "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double Masked, Multicenter Study," *Clin. Ther.*, (2001) 23(3):440-450.

Shimada, et al., "Contributions of Mitogen-Activated Protein Kinase and Nuclear Factor Kappa B to N-(4-hydroxyphenyl) Retinamide-Induced Apoptosis in Prostate Cancer Cells," *Molecular Carcinogenesis*, (2002) 35(3):127-137.

Shoemaker, R., "The NCI60 Human Tumour Cell Line Anticancer Drug Screen," *Nature Reviews Cancer*, (2006) 6:813-823.

Silva-Jardim, et al., "The *Leishmania chagasi* Proteasome: Role in Promastigotes Growth and Amastigotes Survival within Murine Macrophages", *Acta Tropica*, (2004) 91:121-130.

Silverman, Richard B., *The Organic Chemistry of Drug Design and Drug Action*, Academic Press, San Diego, (1992) 19-21.

Stach, et al., "New Primers for the Class *Actinobacteria*: Application to Marine and Terrestrial Environments," *Environmental Mircrobiology*, (2003) 5(10):828-841.

Stach, et al., "Statistical Approaches for Estimating Actinobacterial Diversity in Marine Sediments," *Appl. Environ.I Mircrobiol.*, (Oct. 2003) 69(10):6189-6200.

Stackebrandt, et al., "Proposal for a New Hierarchic Classification Systems, *Actinobacteria* classis Nov.," *Int. J. of Syst. Bacteriol.*, (Apr. 1997) 47(2):479-491.

Stackebrandt, et al., "Taxonomic Note: A Place for DNA-DNA Reassociation and 16S rRNA Sequence Analysis in the Present Species Definition in Bacteriology," *Int. J. of Syst. Bacteriol.*, (Oct. 1994) 44(4):846-849.

Stadler et al., "Cinnabaramides A-G: Analogues of Lactacystin and Salinosporamide from a Terrestrial Streptomycete," *J. Nat. Prod.* (Feb. 2007) 70(2):246-252.

Stanford, et al., "Bortezomib Treatment for Multiple Myeloma," *Ann. Pharmacother.*, (2003) 37:1825-1830.

Stella et al., (Ed.), "Prodrugs: Challenges and Rewards, Part 1", American Association of Pharma. Scientists (2007), p. 24.

Streitwieser et al., *Introduction to Organic Chemistry*, 2nd ed., Macmillan Publishing Co. Inc., New York, NY (1981) pp. 169-171.

Sunwoo, et al., "Novel Proteasome Inhibitor PS-341 Inhibits Activation of Nuclear Factor-kB, Cell Survival, Tumor Growth, and Angiogenesis in Squamous Cell Carcinoma," *Clin. Cancer Res.*, (2001) 7:1419-1428.

Suzuki, et al., "Chemosensitization of Drug and Rituximab-Resistant Daudi B-NHL Clones to Drug-Induced Apoptosis by the Proteasome Inhibitor NPI-0052," Blood, (2005) 106:1521 abstract.

Tabuchi, et al., "Application of 'Proteasome Tolerance' to Therapies for Neurodegenerative Disease," Alzheimer's and Dementia, (2006) 2(3) (1 Supplement):5628.

Takeuchi, et al., "Troglitazone Induces G1 Arrest by p27 Induction That Is Mediated by Inhibition of Proteasome in Human Gastric Cancer Cells," *Jpn. J. Cancer Res.*, (2002) 93:774-782.

Tang, et al., "Cloning and Hererologous Expression of the Epothilong Gene Cluster," *Science*, (Jan. 28, 2000) 287:640-642.

Tang, et al., "Proteasome Activity is Required for Anthrax Lethal Toxin to Kill Macrophages," *Infect. Immun.*, (1999) 67(6):3055-3060.

Tauchi, et al., "Molecular Mechanisms of Resistance of Leukemia to Imatinib Mesylate," *Leukemia Research*, (May, 2004) 28:39-45.

Thompson, et al., "Clustal W: improving the sensitivity of progressive multiple sequence alignment through sequence weighting, position-specific gap penalties and weight matrix choice," *Nucleic Acids Research*, (1994) 22(22):4673-4680.

Tomida, et al., "Drug Resistance Pathways As Targets", Anticancer Drug Development, Academic Press, (2002) Chapter 5:77-90.

Versalovic, et al., "Distribution of repetitive DNA sequences in eubacteria and application to fingerprinting of bacterial genomes," *Nucleic Acids Research*, (1991) 19(24):6823-6831.

Vitale, et al., "Anthrax lethal factor cleaves the N-terminus of MAPKKS and induces tyrosine/threonine phosphorylation of MAPKS in cultured macrophages," *J. Applied Microbiology*, (1999) 87:288.

Vitale, et al., "Susceptibility of Mitogen-Activated Protein Kinase Kinase Family Members to Proteolysis by Anthrax Lethal Factor," *Biochem. J.*, (2000) 352:739-745.

Voskoglou-Nomikos, et al., "Clinical Predictive Value of the in Vitro Cell Line, Human Xenograft, and Mouse Allograft Preclinical Cancer Models", *Clin Cancer Res.*, (2003) 9:4227-4239.

Ward, Bess B., "How Many Species of Prokaryotes are There?" *Proc. Natl. Acad. Sci. USA*, (Aug. 6, 2002) 99(16):10234-10236.

Watve, et al., "How Many Antibiotics are Produced by the Genus *Streptomyces*?" *Arch. Microbio.*, (2001) 176:386-390.

Weyland, H., "Actinomycetes in North Sea and Atlantic Ocean Sediments," *Nature*, (1969) 223:858.

Weyland, H., "Distribution of Actinomycetes on the Sea Floor," *Actinomycetes ZBL*. Bakt. Suppl., (1981) 11:185-193.

Wheelis, et al., "On the Nature of Global Classification," *Proc. Natl. Acad. Sci. USA*, (Apr. 1992) 89:2930-2934.

Williams et al., "New Cytotoxic Salinosporamides from the Marine Actinomycete *Salinispora Tropica*," *J. Org. Chem.*, (2005) 70(16):6196-6203.

Woese, Carl R., "Bacterial Evolution," *Microbiological Rev.*, (Jun. 1987) 51(2):221-271.

Yew, et al., "Proteasome Inhibition by Lactacystin in Primary Neuronal Cells Induces Both Potentially Neuroprotective and Pro-Apoptotic Transcriptional Responses: a Microarray Analysis," *J. Neurochem.*, (2005) 94(4):943-956.

Zaks, A., "Industrial Biocatalysis," *Curr. Opin. Chem. Biol.*, (2001) 5:130-136.

Zhang, et al., "Postischemic (6 Hour) Treatment with Recombinant Human Tissue Plaminogen Activator and Proteasome Inhibitor PS-519 Reduces Infarction in a Rat Model of Embolic Focal Cerebral lschemia," *Stroke*, (2001) 2926-2931.

Zheng, et al., "Detection of Antitumor and Antimicrobial Activities in Marine Organism Associated . Actinomycetes Isolated From the Taiwan Strait, China," *FEMS Microbiology Letters*, (2000) 188:87-91.
International Search Report and Written Opinion dated Jul. 12, 2006 in International Application No. PCT/US2005/044091, International Filing Date: Dec. 2, 2005.
International Preliminary Report on Patentability dated Jun. 14, 2007 in International Application No. PCT/US2005/044091, International Filing Date: Dec. 2, 2005.
International Search Report and Written Opinion (corrected version) dated Jul. 8, 2005 in International Application No. PCT/US2004/019543, International Filing Date: Jun. 18, 2004.
International Preliminary Report on Patentability dated Jan. 3, 2006 in International Application No. PCT/US2004/019543, International Filing Date: Jun. 18, 2004.
International Search Report and Written Opinion dated Nov. 29, 2004 in International Application No. PCT/US2004/019453, International Filing Date: Jun. 18, 2004.
International Preliminary Report on Patentability dated Mar. 14, 2005 in International Application No. PCT/US2004/19453, International Filing Date: Jun. 18, 2004.
International Search Report and Written Opinion dated Dec. 29, 2006 in International Application No. PCT/US2005/014846, International Filing Date: Apr. 29, 2005.
International Preliminary Report on Patentability dated Jan. 23, 2007 in International Application No. PCT/US2005/014846, International Filing Date: Apr. 29, 2005.
International Search Report dated Aug. 2, 2002 in International Application No. PCT/US01/043758, International Filing Date: Nov. 16, 2001.
International Preliminary Report on Patentability dated Aug. 24, 2004 in International Application No. PCT/US2001/043758, International Filing Date: Nov. 16, 2001.
International Search Report and Written Opinion dated Feb. 27, 2007 in International Application No. PCT/US06/016104, International Filing Date: Apr. 27, 2006.
International Preliminary Report on Patentability dated Oct. 30, 2007 in International Application No. PCT/US2006/016104, International Filing Date: Apr. 27, 2006.
International Search Report and Written Opinion mailed Jan. 29, 2009 for corresponding International Application No. PCT/US2008/062553 International Filing Date: May 2, 2008.
International Preliminary Report on Patentability dated Nov. 19, 2009 in International Application No. PCT/US2008/062553, International Filing Date: May 2, 2008.
International Search Report and Written Opinion dated Sep. 28, 2009 for International Application No. PCT/US2009/043644, International Filing Date: May 12, 2009.
International Preliminary Report on Patentability (Chapter II) dated Aug. 6, 2010 for International Application No. PCT/US2009/043644, International Filing Date: May 12, 2009.
International Search Report and Written Opinion dated May 12, 2006 in International Application No. PCT/US2005/043668, International Filing Date: Dec. 2, 2005.
International Preliminary Report on Patentability dated Jun. 14, 2007 in International Application No. PCT/US2005/043668, International Filing Date: Dec. 2, 2005.
International Search Report and Written Opinion dated Nov. 15, 2005 in International Application No. PCT/US2005/012218, International Filing Date: Apr. 11, 2005.
International Preliminary Report on Patentability dated Oct. 11, 2006 in International Application No. PCT/US2005/012218, International Filing Date: Apr. 11, 2005.
International Search Report and Written Opinion dated Oct. 19, 2005 in International Application No. PCT/US2005/012113, International Filing Date: Apr. 11, 2005.
International Preliminary Report on Patentability dated Oct. 11, 2006 in International Application No. PCT/US2005/012113, International Filing Date: Apr. 11, 2005.
International Search Report and Written Opinion dated Jan. 10, 2007 in International Application No. PCT/US2006/031314, International Filing Date: Aug. 10, 2006.
International Preliminary Report on Patentability dated Feb. 12, 2008 in International Application No. PCT/US2006/031314, International Filing Date: Aug. 10, 2006.
International Search Report and Written Opinion dated Aug. 3, 2007 in International Application No. PCT/US2006/035196, International Filing Date: Sep. 8, 2006.
International Preliminary Report on Patentability dated Mar. 18, 2008 in International Application No. PCT/US2006/035196, International Filing Date: Sep. 8, 2006.
International Search Report and Written Opinion dated Nov. 27, 2007 in International Application No. PCT/US2006/043277, International Filing Date: Nov. 6, 2006.
International Preliminary Report on Patentability dated May 6, 2008 in International Application No. PCT/US2006/043277, International Filing Date: Nov. 6, 2006.
EFS File History of U.S. Appl. No. 12/329,518, filed Dec. 5, 2008.
EFS File History of U.S. Appl. No. 10/871,368, filed Mar. 3, 2005.
EFS File History of U.S. Appl. No. 12/136,688, filed Jun. 10, 2008 as of Apr. 11, 2012, Uploaded in 5 Parts.
EFS File History of U.S. Appl. No. 11/118,260, filed Apr. 29, 2005.
EFS File History of U.S. Appl. No. 09/991,518, filed Nov. 16, 2001.
EFS File History of U.S. Appl. No. 11/228,416, filed Sep. 15, 2005.
EFS File History of U.S. Appl. No. 11/841,588, filed Aug. 20, 2007.
EFS File History of U.S. Appl. No. 11/966,787, filed Dec. 28, 2007.
EFS File History of U.S. Appl. No. 11/966,801, filed Dec. 28, 2007.
EFS File History of U.S. Appl. No. 10/600,854, filed Jun. 20, 2003.
EFS File History of U.S. Appl. No. 10/838,157, filed Apr. 30, 2004.
EFS File History of U.S. Appl. No. 11/147,622, filed Jun. 7, 2005.
EFS File History of U.S. Appl. No. 11/705,694, filed Feb. 12, 2007.
EFS File History of U.S. Appl. No. 12/638,860, filed Dec. 15, 2009 as of Mar. 9, 2012, Uploaded in 3 Parts.
EFS File History of U.S. Appl. No. 10/561,711, filed Sep. 11, 2009 as of Apr. 21, 2012, Uploaded in 5 Parts.
EFS File History of U.S. Appl. No. 11/412,476, filed Apr. 27, 2006.
EFS File History of U.S. Appl. No. 11/865,704, filed Oct. 1, 2007.
EFS File History of U.S. Appl. No. 11/453,374, filed Jun. 15, 2006.
EFS File History of U.S. Appl. No. 12/114,449, filed May 2, 2008.
EFS File History of U.S. Appl. No. 12/720,557, filed Mar. 9, 2010 as of Dec. 9, 2011.
EFS File History of U.S. Appl. No. 12/464,686, filed May 12, 2009.
EFS File History of U.S. Appl. No. 13/052,827, filed Mar. 21, 2011 as of Mar. 20, 2012.
EFS File History of U.S. Appl. No. 11/293,354, filed Dec. 2, 2005.
EFS File History of U.S. Appl. No. 12/183,007, filed Jul. 30, 2008 as of Nov. 7, 2011.
EFS File History of U.S. Appl. No. 12/329,504, filed Dec. 5, 2008 as of Aug. 16, 2011.
EFS File History of U.S. Appl. No. 10/821,621, filed Apr. 9, 2004.
EFS File History of U.S. Appl. No. 11/539,648, filed Oct. 9, 2006.
EFS File History of U.S. Appl. No. 12/028,024, filed Feb. 8, 2008.
EFS File History of U.S. Appl. No. 11/224,589, filed Sep. 12, 2005.
EFS File History of U.S. Appl. No. 12/282,343, filed Feb. 19, 2009 as of Jan. 26, 2012.
Stinson et al., "Morphological and immunocytochemical characteristics of human tumor cell lines for use in a disease-oriented anticancer drug screen" *Anticancer Research* (Jan. 1, 1992) 12:1035-1053.
EFS File History of U.S. Appl. No. 12/136,688, filed Jun. 10, 2008, Uploaded in 5 Parts.
EFS File History of U.S. Appl. No. 12/638,860, filed Dec. 15, 2009, Uploaded 3 Parts.
EFS File History of U.S. Appl. No. 10/561,711, filed Sep. 11, 2009, Uploadedin 5 Parts.
EFS File History of U.S. Appl. No. 12/720,557, filed Mar. 9, 2010.
EFS File History of U.S. Appl. No. 13/052,827, filed Mar. 21, 2011.
EFS File History of U.S. Appl. No. 12/329,504, filed Dec. 5, 2008 as of Aug. 9, 2012.
EFS File History of U.S. Appl. No. 12/282,343, filed Feb. 19, 2009.
EFS File History of U.S. Appl. No. 13/490,232, filed Jun. 6, 2012 as of Sep. 14, 2012.

* cited by examiner

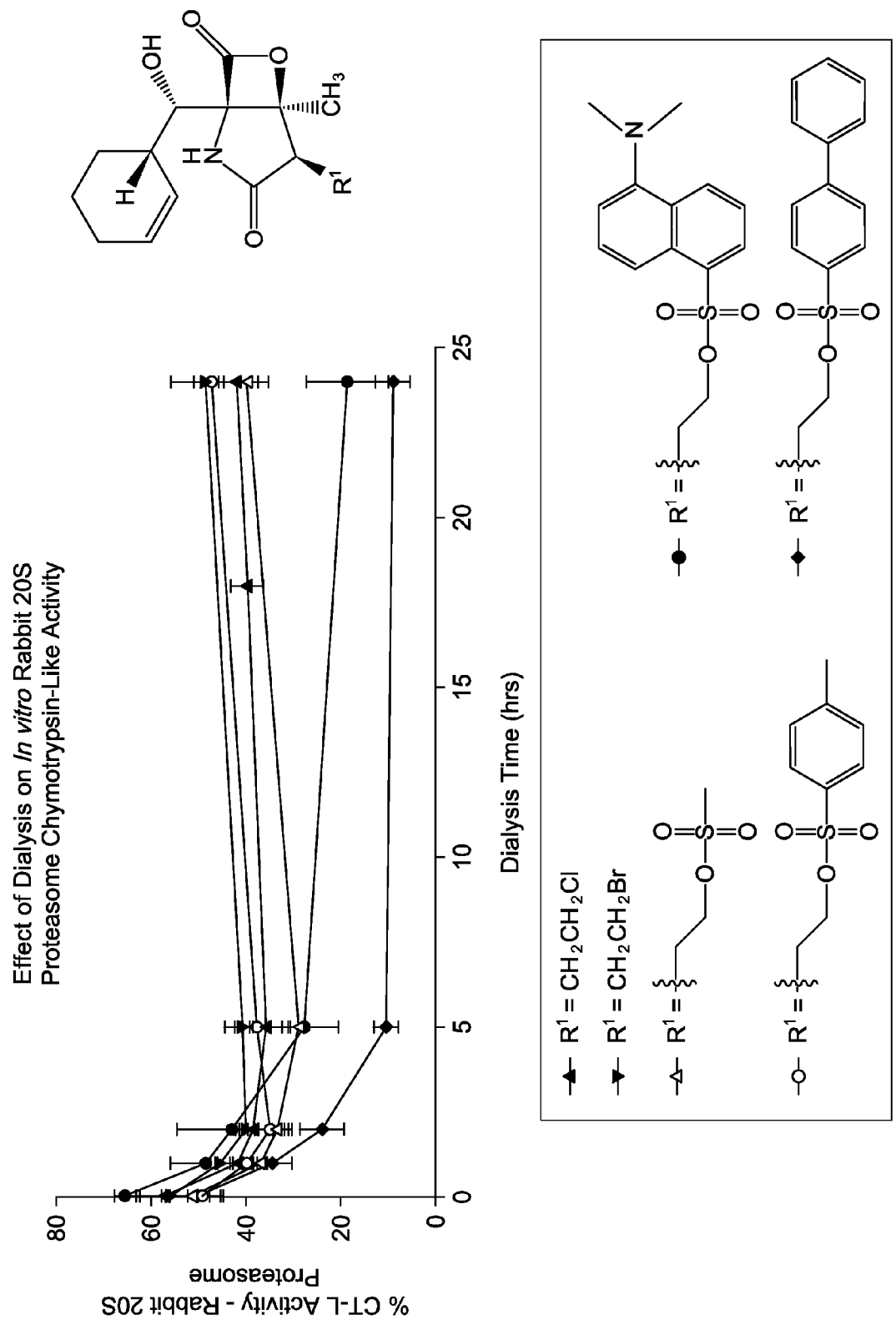

PROTEASOME INHIBITORS

CROSS-REFERENCE TO RELATED APPLICATIONS

This application is a continuation of U.S. application Ser. No. 13/052,827, entitled "PROTEASOME INHIBITORS," filed Mar. 21, 2011, which is a divisional of U.S. application Ser. No. 12/464,686, entitled "PROTEASOME INHIBITORS," filed May 12, 2009, now U.S. Pat. No. 7,910,616, which claims priority to U.S. Provisional Patent Application No. 61/052,576, entitled "PROTEASOME INHIBITORS," filed May 12, 2008, all of which is incorporated herein by reference in their entireties, including any drawings.

BACKGROUND

1. Field

The present application relates to certain compounds and to methods for the preparation of certain compounds that can be used in the fields of chemistry and medicine.

2. Description

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria, fungi and protozoa are becoming increasingly difficult to treat and cure. For example, more and more bacteria, fungi and protozoa are developing resistance to current antibiotics and chemotherapeutic agents. Examples of such microbes include *Bacillus, Leishmania, Plasmodium* and *Trypanosoma*.

Furthermore, a growing number of diseases and medical conditions are classified as inflammatory diseases. Such diseases include conditions such as asthma to cardiovascular diseases. These diseases continue to affect larger and larger numbers of people worldwide despite new therapies and medical advances.

Therefore, a need exists for additional chemotherapeutics, anti-microbial agents, and anti-inflammatory agents to treat cancer, inflammatory diseases and infectious disease. A continuing effort is being made by individual investigators, academia and companies to identify new, potentially useful chemotherapeutic and anti-microbial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY

The embodiments disclosed herein generally relate compounds, including heterocyclic compounds and analogs thereof that include a sulfonate ester, carboxylic ester or ether group. Some embodiments are directed to the chemical compounds and pharmaceutical compositions that contain one or more chemical compounds. Other embodiments are directed to methods of synthesizing the chemical compounds. Still other embodiments are directed to methods of treating and/or ameliorating a disease or conditions with one or more chemical compounds or a pharmaceutical composition that contains one or more chemical compounds.

Some embodiments disclosed herein relate to a compound of Formula (I), or pharmaceutically acceptable salt, ester or prodrug thereof:

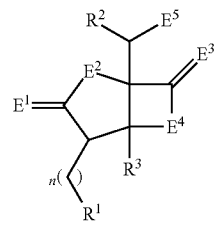

wherein $R^1$, $R^2$, $R^3$, $E^1$, $E^2$, $E^3$, $E^4$, $E^5$ and n are described herein.

Other embodiments described herein relate to a method of synthesizing a compound of Formula (I) that includes reacting a compound of Formula (A) with a silver reagent, such as AgF or AgF—$CaF_2$, to form a compound of Formula (B), and then reacting the compound of Formula (B) with

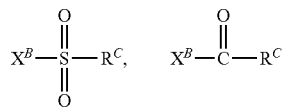

or $X^B$—$R^C$ to form a compound of Formula (I). The variables $R^1$, $R^2$, $R^3$, $E^1$, $E^2$, $E^3$, $E^4$, $E^5$, $R^A$, $R^B$, $R^D$, $E^A$, $E^B$, $E^D$, $E^E$, $E^E$, $X^A$, $X^B$, $R^C$, n and m.

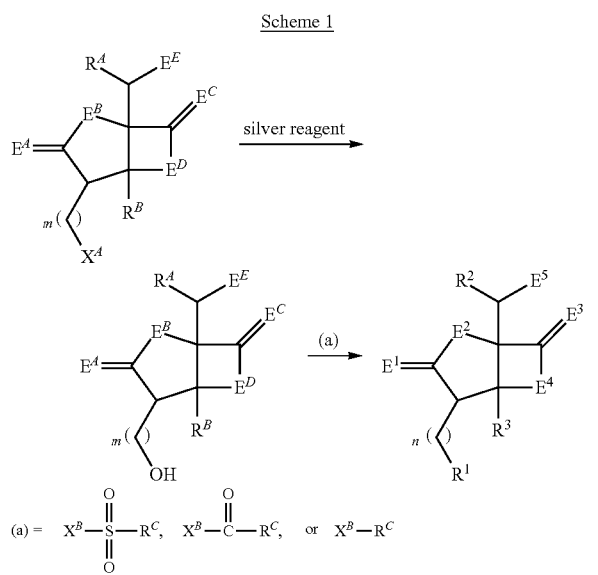

Scheme 1

DETAILED DESCRIPTION

Numerous references are cited herein. The references cited herein, including the U.S. patents cited herein, are each to be considered incorporated by reference in their entirety into this specification.

Salinosporamide A and its analogs thereof have various biological activities. The structure of Salinosporamide A is shown below.

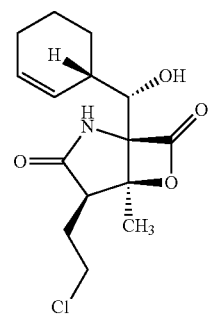

Studies have been conducted that show Salinosporamide A and its analogs have proteasome inhibitory activity, effect NF-κB/IκB signaling pathway, and have anti-anthrax activity. Salinosporamide A and several analogs, as well as biological activity of the same, are described in U.S. Provisional Patent Applications Nos. 60/480,270, filed Jun. 20, 2003; 60/566,952, filed Apr. 30, 2004; 60/627,461, filed Nov. 12, 2004; 60/633,379, filed Dec. 3, 2004; 60/643,922, filed Jan. 13, 2005; 60/658,884, filed Mar. 4, 2005; 60/676,533, filed Apr. 29, 2005; 60/567,336, filed Apr. 30, 2004; 60/580,838, filed Jun. 18, 2004; 60/591,190, filed Jul. 26, 2004; 60/627,462, filed Nov. 12, 2004; 60/644,132, filed Jan. 13, 2005; 60/659,385, filed Mar. 4, 2005; 61/034,900, filed Mar. 7, 2008 and 61/073,545, filed Jun. 18, 2008; U.S. patent applications No. 10/871,368, filed Jun. 18, 2004; Ser. No. 11/118,260, filed Apr. 29, 2005; Ser. No. 11/412,476, filed Apr. 27, 2006; Ser. No. 11/453,374, filed Jun. 15, 2006; Ser. No. 11/865,704, filed Oct. 1, 2007; Ser. No. 11/697,689, filed Apr. 6, 2007; Ser. No. 12/136,688, filed Jun. 10, 2008 and Ser. No. 12/399,382, filed Mar. 6, 2009; and International Patent Applications Nos. PCT/US2004/019543, filed Jun. 18, 2004; PCT/US2005/044091, filed Dec. 2, 2005; PCT/US2005/014846, filed Apr. 29, 2005; PCT/US2006/016104, filed Apr. 27, 2006; PCT/US2007/008562, filed Apr. 6, 2007; PCT/US2009/036376, filed Mar. 6, 2009; each of which is hereby incorporated by reference in its entirety.

Disclosed herein analogs of Salinosporamide A that include a sulfonate ester, carboxylic ester or ether group. Also disclosed herein are pharmaceutical compositions that include one or more of the Salinosporamide A analogs with a sulfonate ester, carboxylic ester or ether group, methods of making Salinosporamide A analogs with a sulfonate ester, carboxylic ester or ether group and methods of using Salinosporamide A analogs with a sulfonate ester, carboxylic ester or ether group for treating and/or ameliorating a disease or condition such as cancer, a microbial disease and/or inflammation. In some embodiments, analogs of Salinosporamide A can include a bulky sulfonate ester, a bulky carboxylic ester or a bulky ether group. In an embodiment, analogs of Salinosporamide A that include a bulky sulfonate ester, a bulky carboxylic ester or a bulky ether group have improved inhibition of the caspase activity.

Some embodiments described herein relate to a pharmaceutical composition that can include one or more compounds described herein, such as a compound of Formula (I), or pharmaceutically acceptable salt, ester or prodrug thereof, and one or more selected from a diluent, an excipient and a carrier.

Another embodiment described herein relates to a method for treating, alleviating or diagnosing a neoplastic disease that can include administering to a subject a therapeutically effective amount of one or more compounds described herein (for example, a compound of Formula (I)), or pharmaceutically acceptable salt, ester or prodrug thereof, or a pharmaceutical composition described herein, such as a pharmaceutical composition that includes one or more compounds of Formula (I).

Other embodiments described herein relate to a method for inhibiting the growth of a cancer cell that can include contacting the cancer cell with an effective amount of one or more compounds described herein, such as a compound of Formula (I), or pharmaceutically acceptable salt, ester or prodrug thereof, or a pharmaceutical composition that includes one or more compounds of Formula (I).

An embodiment described herein relates to a method for inhibiting proteasome activity that can include contacting a cell with an effective amount of one or more compounds described herein, such as a compound of Formula (I), or pharmaceutically acceptable salt, ester or prodrug thereof, or a pharmaceutical composition that includes one or more compounds of Formula (I).

Some embodiments described herein relate to a method for inhibiting NF-κB activation that can include contacting a cell with an effective amount of one or more compounds described herein (for example, a compound of Formula (I)), or pharmaceutically acceptable salt, ester or prodrug thereof, or a pharmaceutical composition that includes one or more compounds of Formula (I).

BRIEF DESCRIPTION OF THE DRAWINGS

FIG. 1 shows a graph of the results of a dialysis experiment in the 20S proteasome of several compound of Formula (I).

Unless otherwise indicated, when a substituent is deemed to be "optionally substituted," or "substituted" it is meant that the indicated group may be substituted with one or more group(s) individually and independently selected from alkyl, alkenyl, alkynyl, alkoxy, cycloalkyl, cycloalkenyl, cycloalkynyl, acyl, acylamino, acyloxy, amino, mono-substituted amine, di-substituted amine, alkyl amino, aminoacyl, aminoacyloxy, oxyacylamino, halogen, mono-haloalkyl, di-haloalkyl, tri-haloalkyl, mono-haloalkoxy, di-haloalkoxy, tri-haloalkoxy, hydroxy, carboxylalkyl, thioketo, thiol, thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$—H, —SO$_2$—OH, —SO$_2$-alkyl, —SO$_2$-aryl and —SO$_2$-heteroaryl, boronate alkyl, boronic acid, (OH)$_2$B-alkyl, phosphate and phosphate esters, phosphonooxy, phosphonooxyalkyl, azido, azidoalkyl, ammonium, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, cyano, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl.

Whenever a group is described as "optionally substituted" the group may be unsubstituted or substituted with one or more substituents as described herein.

As used herein, any "R" group(s) such as, without limitation, R, R$^1$, R$^2$, R$^3$, R$^4$, R$^5$, R$^6$, R$^7$, R$^8$, R$^a$, R$^b$, R$^A$, R$^B$ and R$^C$ represent substituents that can be attached to the indicated atom. An R group may be substituted or unsubstituted. If two "R" groups are covalently bonded to the same atom or to adjacent atoms, then they may be "taken together" as defined herein to form a cycloalkyl, aryl, heteroaryl or heterocycle. For example, without limitation, if R$^{1a}$ and R$^{1b}$ of an NR$^{1a}$R$^{1b}$ group are indicated to be "taken together," it means that they are covalently bonded to one another to form a ring:

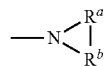

As used herein, "C$_m$ to C$_n$" in which "m" and "n" are integers refers to the number of carbon atoms in an alkyl, alkenyl or alkynyl group or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "m" to "n", inclusive, carbon atoms. Thus, for example, a "C$_1$ to C$_4$ alkyl" group refers to all alkyl groups having from 1 to 4 carbons, that is, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—. If no "m" and "n" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed. Whenever it appears herein, a numerical range such as "1 to 20" refers to each integer in the given range. For example, "1 to 20 carbon atoms" means that the indicated group may consist of 1 carbon atom, 2 carbon atoms, 3 carbon atoms, etc., up to and including 20 carbon atoms.

The term "alkyl," as used herein, means any unbranched or branched, substituted or unsubstituted, saturated hydrocarbon, with C$_1$-C$_{24}$ preferred, and C$_1$-C$_6$ hydrocarbons being preferred, with methyl, ethyl, propyl, isopropyl, butyl, isobutyl, and tert-butyl, and pentyl being most preferred.

The term "alkenyl," as used herein, means any unbranched or branched, substituted or unsubstituted, unsaturated hydrocarbon containing one or more double bonds. Some examples of alkenyl groups include allyl, homo-allyl, vinyl, crotyl, butenyl, pentenyl, hexenyl, heptenyl and octenyl.

The term "alkynyl" as used herein, means any unbranched or branched, substituted or unsubstituted, unsaturated hydrocarbon with one or more triple bonds As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, and the like.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

The term "acyl" refers to hydrogen, alkyl, alkenyl, alkynyl, cycloalkyl, cycloalkenyl, cycloalkynyl, aryl, heteroaryl or heterocyclyl connected, as substituents, via a carbonyl group. Examples include formyl, acetyl, propanoyl, benzoyl, and acryl. An acyl may be substituted or unsubstituted.

The term "carboxy" group refers to a "—C(=O)OR" group in which R can be hydrogen, alkyl, alkenyl, alkynyl, cycloalkyl, cycloalkenyl, cycloalkynyl, aryl, heteroaryl or heterocyclyl. A carboxy may be substituted or unsubstituted.

As used herein, "aryl" refers to a hydrocarbon monocyclic or multicyclic aromatic ring system that has a fully delocalized pi-electron system throughout all the rings. The number of carbon atoms in an aryl group can vary. For example, the aryl group can be a C$_6$-C$_{14}$ aryl group, a C$_6$-C$_{10}$ aryl group, or a C$_6$ aryl group. Moreover, the term "aryl" includes fused ring systems wherein two carbocyclic rings share least one chemical bond. Some examples of "aryl" rings include optionally substituted phenyl, naphthalenyl, phenanthrenyl and anthracenyl. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. A heteroaryl can be substituted or unsubstituted. A non-limiting list of examples of heteroaryls include furan, thiophene, phthalazine, pyrrole, oxazole, thiazole, imidazole, pyrazole, isoxazole, isothiazole, triazole, thiadiazole, pyridine, pyridazine, pyrimidine, pyrazine, triazine, benzofuran, benzothiopene and quinoline.

The terms "heterocycle" and "heterocyclyl" are intended to mean three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, cyclic carbamates, and the like. When composed of two or more rings, the rings may be joined together in a fused fashion. Examples of benzo-fused heterocyclyl groups include, but are not limited to, benzimidazolidinone, tetrahydroquinoline, and methylenedioxybenzene ring structures. Some examples of heterocyclyls include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyridine, pyridinium, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. A heterocycle group may be substituted or unsubstituted.

The term "alkoxy" refers to any unbranched, or branched, substituted or unsubstituted, saturated or unsaturated ether. In some embodiments, the alkoxy is an unbranched or branched alkyl group connected to the indicated group via an oxygen atom. Examples of alkoxy groups include methoxy, ethoxy, isopropoxy, tert-butoxy and the like.

The term "(cycloalkyl)alkyl is understood as a cycloalkyl group connected, as a substituent, via a lower alkylene. The (cycloalkyl)alkyl group and lower alkylene of a (cycloalkyl)alkyl group may be substituted or unsubstituted.

The terms "(heterocycle)alkyl" and "(heterocyclyl)alkyl" are understood as a heterocycle group connected, as a substituent, via a lower alkylene. The heterocycle group and the lower alkylene of a (heterocycle)alkyl group may be substituted or unsubstituted.

The term "arylalkyl" is intended to mean an aryl group connected, as a substituent, via a lower alkylene, each as defined herein. The aryl group and lower alkylene of an arylalkyl may be substituted or unsubstituted. Examples include benzyl, substituted benzyl, 2-phenylethyl, 3-phenylpropyl, and naphthylalkyl.

The term "heteroarylalkyl" is understood as heteroaryl groups connected, as substituents, via a lower alkylene, each as defined herein. The heteroaryl and lower alkylene of a heteroarylalkyl group may be substituted or unsubstituted. Examples include 2-thienylmethyl, 3-thienylmethyl, furylmethyl, thienylethyl, pyrrolylalkyl, pyridylalkyl, isoxazolylalkyl, imidazolylalkyl, and their substituted as well as benzo-fused analogs.

The term "halogen atom," as used herein, means any one of the radio-stable atoms of column 7 of the Periodic Table of the Elements, i.e., fluorine, chlorine, bromine, or iodine, with bromine and chlorine being preferred.

As used herein, the term "mono-substituted amine" refers to a "—NHR" group, wherein R can be alkyl, alkenyl, alkynyl, cycloalkyl, cycloalkenyl, cycloalkynyl, aryl, heteroaryl or heterocyclyl. A mono-substituted amine may be substituted or unsubstituted.

As used herein, the term "di-substituted amine" refers to a "—NR'R'" group, wherein each R' can be independently alkyl, alkenyl, alkynyl, cycloalkyl, cycloalkenyl, cycloalkynyl, aryl, heteroaryl or heterocyclyl. A di-substituted amine may be substituted or unsubstituted.

As employed herein, the following terms have their accepted meaning in the chemical literature.
ACN acetonitrile
C-L caspase-like
CT-L chymotrypsin-like
DCC N,N'-dicyclohexylcarbodiimide
DMAP 4-(dimethylamino)pyridine
DMSO dimethylsulfoxide
EDC 1-ethyl-3-(3-dimethylaminopropyl) carbodiimide
EDTA ethylenediaminetetraacetic acid
EtOAc ethyl acetate
HPLC high performance liquid chromatography
HRESIMS high-resolution mass spectrometry
TFA trifluoroacetic acid
THF tetrahydrofuran
T-L trypsin-like The terms "protecting group moiety" and "protecting group moieties" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference. The protecting group moiety may be chosen in such a way, that they are stable to the reaction conditions applied and readily removed at a convenient stage using methodology known from the art. A non-limiting list of protecting groups include benzyl; substituted benzyl; alkylcarbonyls (e.g., t-butoxycarbonyl (BOC)); arylalkylcarbonyls (e.g., benzyloxycarbonyl, benzoyl); substituted methyl ether (e.g. methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g. benzoate ester); carbonates (e.g. methoxymethylcarbonate); sulfonates (e.g. tosylate, mesylate); acyclic ketal (e.g. dimethyl acetal); cyclic ketals (e.g., 1,3-dioxane or 1,3-dioxolanes); acyclic acetal; cyclic acetal; acyclic hemiacetal; cyclic hemiacetal; and cyclic dithioketals (e.g., 1,3-dithiane or 1,3-dithiolane). As used herein, any "PG" group(s) such as, without limitation, $PG^1$, $PG^2$ and $PG^3$ represent a protecting group moiety.

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, $5^{th}$ ed., John McMurry (2000), pages 398 and 408; all of which are incorporated herein by reference for the limited purpose of disclosing characteristics and examples of leaving groups.

The terms "pure," "purified," "substantially purified," and "isolated" as used herein refer to the compound of the embodiment being free of other, dissimilar compounds with which the compound, if found in its natural state, would be associated in its natural state. In certain embodiments described as "pure," "purified," "substantially purified," or "isolated" herein, the compound may comprise at least 0.5%, 1%, 5%, 10%, or 20%, and most preferably at least 50% or 75% of the mass, by weight, of a given sample.

The terms "derivative," "variant," or other similar term refers to a compound that is an analog of the other compound.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition it is understood that, in any compound described herein having one or more double bond(s) generating geometrical isomers that can be defined as E or Z, each double bond may independently be E or Z a mixture thereof. Likewise, all tautomeric forms are also intended to be included.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference for the limited purpose describing procedures and preparation of suitable prodrug derivatives.

The term "pro-drug ester" refers to derivatives of the compounds disclosed herein formed by the addition of any of several ester-forming groups that are hydrolyzed under physiological conditions. Examples of pro-drug ester groups include pivaloyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference for the limited purpose of disclosing ester-forming groups that can form prodrug esters.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

Compounds

Some embodiments disclosed herein relate to a compound of Formula (I), or pharmaceutically acceptable salt, ester or prodrug thereof:

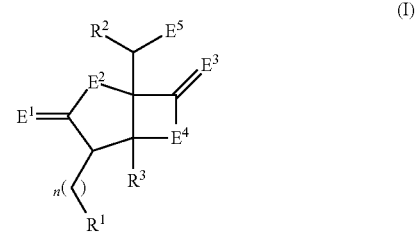

wherein: $R^1$ can have a structure selected from:

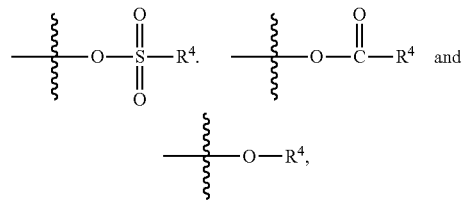

wherein $R^4$ can be selected from a mono-substituted, a poly-substituted or an unsubstituted variant of the following residues: aryl, aryl($C_{1-6}$ alkyl), heteroaryl, heteroaryl($C_{1-6}$ alkyl), heterocyclyl and heterocyclyl($C_{1-6}$ alkyl), wherein $R^4$ can be optionally substituted with

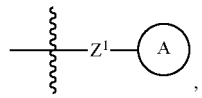

wherein A can be selected from a mono-substituted, a poly-substituted or an unsubstituted variant of the following residues: heterocyclyl, aryl and heteroaryl; and $Z^1$ can be selected from O (oxygen), S (sulfur), N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—$C(=O)N(R^{17})$, CH=CH—$C(=O)$, $O(CH_2)_{1-6}O$, $O(CH_2)_{1-6}$ and $N(R^{17a})C(=O)N(R^{17b})$, wherein $R^{17}$, $R^{17a}$ and $R^{17b}$ can be independently selected from: H, $C_{1-4}$ alkyl, a substituted or unsubstituted benzyl, an allyl, and t-butoxycarbonyl (t-BOC); $R^2$ can be selected from a hydrogen, a halogen, cyano, a mono-substituted, a poly-substituted or an unsubstituted variant of the following residues: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, mono-haloalkyl, di-haloalkyl, tri-haloalkyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; $R^3$ can be selected from hydrogen, halogen, a mono-substituted, a poly-substituted or an unsubstituted variant of the following residues: $C_{1-6}$ alkyl, $C_{3-6}$ cycloalkyl, $C_{2-6}$ alkenyl, $C_{3-6}$ cycloalkenyl, aryl, and arylalkyl; n can be 1, 2 or 3; $E^1$, $E^3$, $E^4$ and $E^5$ can be each independently a substituted or unsubstituted heteroatom; $E^2$ can be a substituted or unsubstituted heteroatom (such as NH) or —$CH_2$— group; and provided that when $R^1$ is

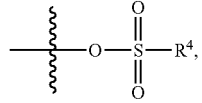

$R^4$ has a molecular weight equal to or greater than 92 g/mol; and provided that when $R^1$ is

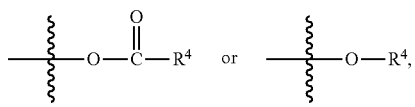

$R^4$ has a molecular weight equal to or greater than 77 g/mol.

In some embodiments, when $R^1$ is

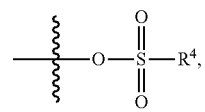

$R^4$ has a molecular weight equal to or greater than 107 g/mol. In other embodiments, when $R^1$ is

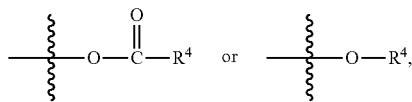

$R^4$ has a molecular weight equal to or greater than 92 g/mol. In an embodiment, when $R^1$ is

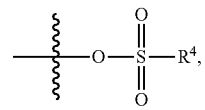

$R^4$ has a molecular weight equal to or greater than 122 g/mol. In another embodiment, when $R^1$ is

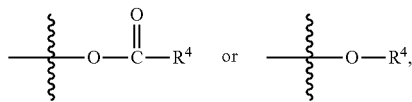

$R^4$ has a molecular weight equal to or greater than 107 g/mol.

In some embodiments, $R^1$ can have a structure selected from:

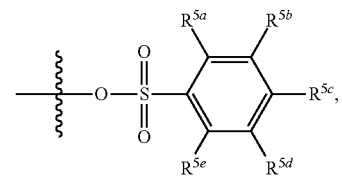

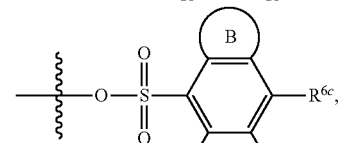

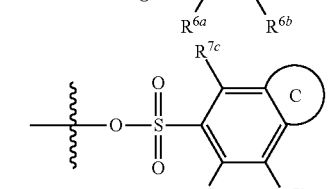

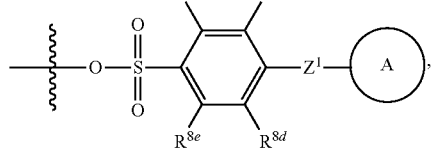

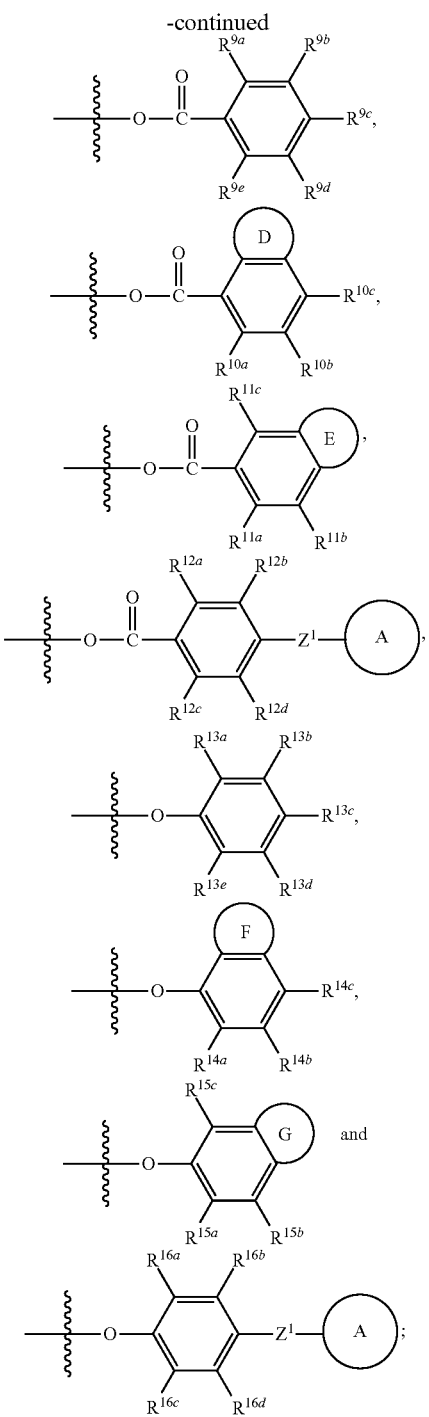

wherein: $R^{5a}$, $R^{5b}$, $R^{5c}$, $R^{5d}$, $R^{5e}$, $R^{9a}$, $R^{9b}$, $R^{9c}$, $R^{9d}$, $R^{9e}$, $R^{13a}$, $R^{13b}$, $R^{13c}$, $R^{13d}$ and $R^{13e}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, cycloalkyl, cycloalkenyl, cycloalkynyl, aryl, heteroaryl, heterocyclyl, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; $R^{6a}$, $R^{6b}$, $R^{6c}$, $R^{10a}$, $R^{10b}$, $R^{10c}$, $R^{14a}$, $R^{14b}$ and $R^{14c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; $R^{7b}$, $R^{7c}$, $R^{11a}$, $R^{11b}$, $R^{11c}$, $R^{15a}$, $R^{15b}$ and $R^{15c}$ can be each independently selected from: hydrogen, halo, a mono-substituted, a poly-substituted or an unsubstituted variant of the following residues: $C_{1-24}$ alkyl, $C_{2-24}$ alkenyl, $C_{2-24}$ alkynyl, nitro, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, cyano, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; $R^{8a}$, $R^{8b}$, $R^{8c}$, $R^{8d}$, $R^{12a}$, $R^{12b}$, $R^{12c}$, $R^{12d}$, $R^{16a}$, $R^{16b}$, $R^{16c}$ and $R^{16d}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphoryl alkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl and $—S(\!=\!O)_2O^-$; B, D and F can be each independently selected from: a mono-substituted, a poly-substituted or an unsubstituted variant of the following residues: heterocyclyl, aryl, heteroaryl, cycloalkyl and cycloalkenyl; C, E and G can be each independently selected from: a mono-substituted, a poly-substituted or an unsubstituted variant of the following residues: heterocyclyl, aryl, heteroaryl, cycloalkyl and cycloalkenyl; A can be selected from: a mono-substituted, a poly-substituted or an unsubstituted variant of the following residues: heterocyclyl, aryl, heteroaryl, cycloalkyl and cycloalkenyl; and $Z^1$ can be selected from: O, S, N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—C(=O)N($R^{17}$), CH=CH—C(=O), $O(CH_2)_{1-6}O$, $O(CH_2)_{1-6}$ and $N(R^{17a})C(=O)N(R^{17b})$, wherein $R^{17}$, $R^{17a}$ and $R^{17b}$ are independently selected from: H, $C_{1-4}$ alkyl, a substituted or unsubstituted benzyl, an allyl, and t-butoxycarbonyl (t-BOC).

In some embodiments, $R^1$ can have the structure:

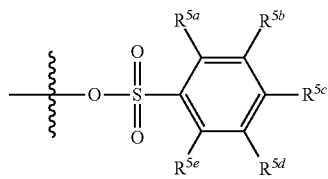

wherein: $R^{5a}$, $R^{5b}$, $R^{5c}$, $R^{5d}$, and $R^{5e}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, cycloalkyl, cycloalkenyl, cycloalkynyl, aryl, heteroaryl, heterocyclyl, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl.

In some embodiments, $R^{5a}$, $R^{5b}$, $R^{5c}$, $R^{5d}$, and $R^{5e}$ can be each independently selected from: hydrogen, halo, nitro, a mono-substituted, a poly-substituted or an unsubstituted variant of the following residues: $C_{1-24}$ alkyl, cycloalkyl, cycloalkenyl, aryl, heteroaryl, heterocyclyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, and carboxy. In another embodiment, $R^{5a}$, $R^{5b}$, $R^{5c}$, $R^{5d}$, and $R^{5e}$ are each independently selected from: hydrogen, halo, nitro, a mono-substituted, a poly-substituted or an unsubstituted $C_{1-24}$ alkyl, aryl, tri-haloalkyl, tri-haloalkoxy, mono-substituted amine, a mono-substituted, a poly-substituted or an unsubstituted alkoxy, and a mono-substituted, a poly-substituted or an unsubstituted carboxy.

In some embodiments, when $R^1$ has the structure:

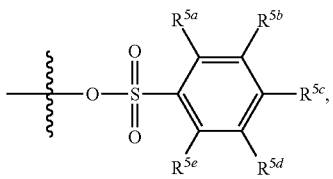

the phenyl ring of $R^1$ can be an unsubstituted phenyl ring, an ortho-substituted phenyl ring, a meta-substituted phenyl ring or a para-substituted phenyl ring. In some embodiments, at least one of $R^{5a}$, $R^{5b}$, $R^{5c}$, $R^{5d}$, and $R^{5e}$ is not hydrogen. In other embodiments, at least two of $R^{5a}$, $R^{5b}$, $R^{5c}$, $R^{5d}$, and $R^{5e}$ are not hydrogen. In still other embodiments, at least three of $R^{5a}$, $R^{5b}$, $R^{5c}$, $R^{5d}$, and $R^{5e}$ are not hydrogen. In yet sill other embodiments, at least four of $R^{5a}$, $R^{5b}$, $R^{5c}$, $R^{5d}$, and $R^{5e}$ are not hydrogen. In an embodiment, $R^{5c}$ is not hydrogen. For example, when $R^{5c}$ is not hydrogen, $R^{5c}$ can be selected from halogen, nitro, trihaloalkyl (e.g., $CF_3$), trihaloalkoxy (e.g., $OCF_3$), acyl (e.g., C(=O)OH) and $C_{1-6}$ alkyl. In some embodiments, at least one of $R^{5b}$ or $R^{5d}$ is not hydrogen. As an example, at least one of $R^{5b}$ or $R^{5d}$ can be an acyl group, such as C(=O)OH. In other embodiments, $R^{5c}$ is not hydrogen and at least one of $R^{5b}$ or $R^{5d}$ is not hydrogen. Thus, the phenyl ring is a para- and meta-substituted phenyl ring. In an embodiment, $R^{5b}$ or $R^{5d}$ can be a nitro group and $R^{5c}$ can be a mono-substituted amine. In other embodiments, $R^{5c}$ is not hydrogen and at least one of $R^{5a}$ or $R^{5e}$ is not hydrogen. Accordingly, the phenyl ring is a para- and ortho-substituted phenyl ring. As example, $R^{5c}$ can be a $C_{1-6}$ alkyl group and one or both of $R^{5a}$ and $R^{5e}$ can also be a $C_{1-6}$ alkyl group.

A non-limiting list of $R^1$ include the following:

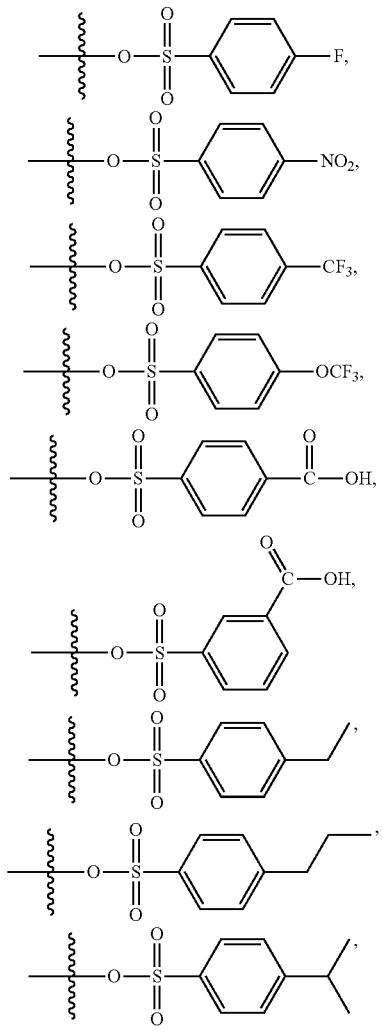

-continued

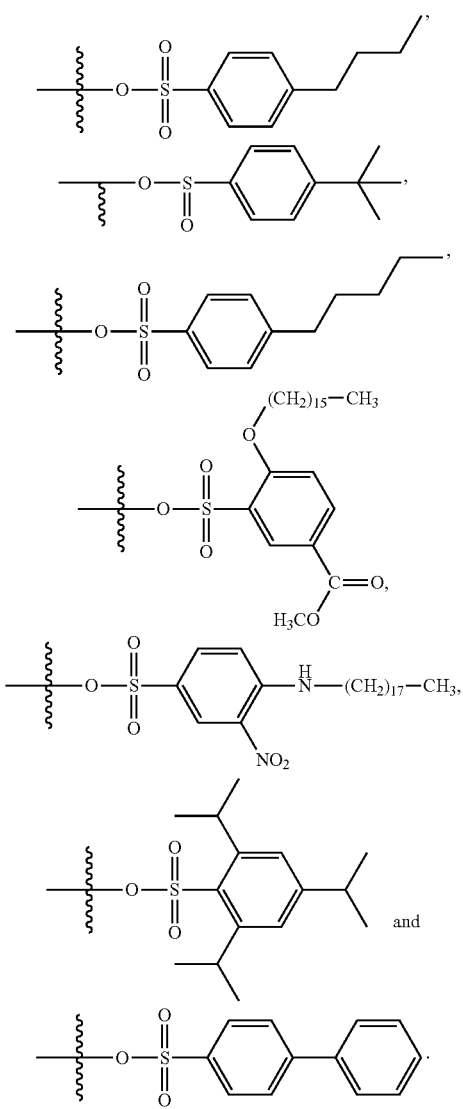

In some embodiments, $R^1$ can have the structure:

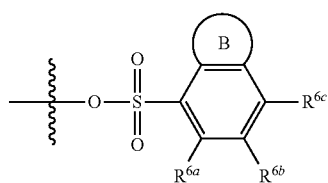

wherein: $R^{6a}$, $R^{6b}$ and $R^{6c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; and B can be selected from: a mono-substituted, a poly-substituted or an unsubstituted variant of the following residues: heterocyclyl, aryl, heteroaryl, cycloalkyl and cycloalkenyl.

In an embodiment, B can be a mono-substituted, a poly-substituted or an unsubstituted aryl ring. For example, B can be a mono-substituted, a poly-substituted or an unsubstituted phenyl. In some embodiments, B can be a mono-substituted phenyl. In other embodiments, B can be an unsubstituted phenyl. In another embodiment, B can be a mono-substituted, a poly-substituted or an unsubstituted heteroaryl ring. In still another embodiment, B can be a mono-substituted, a poly-substituted or an unsubstituted heterocyclyl ring. In yet still other embodiments, B can be a mono-substituted, a poly-substituted or an unsubstituted cycloalkyl ring. In some embodiments, B can be a mono-substituted, a poly-substituted or an unsubstituted cycloalkenyl ring. In some embodiments, $R^{6a}$, $R^{6b}$ and $R^{6c}$ can be each hydrogen. In an embodiment, $R^{6a}$, $R^{6b}$ and $R^{6c}$ can be each hydrogen and B can be a mono-substituted, a poly-substituted or an unsubstituted phenyl ring. In some embodiments, B can be a substituted phenyl ring substituted with amino, mono-substituted amino, or di-substituted amino.

Examples of $R^1$ include the following:

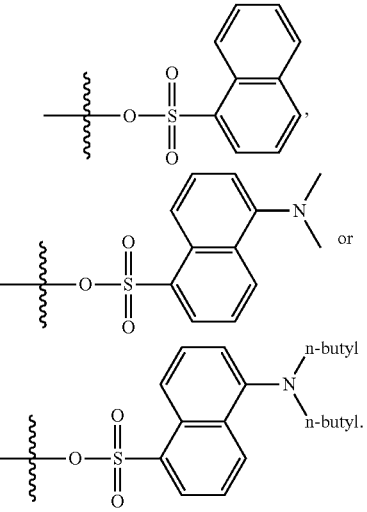

In some embodiments, $R^1$ can have the structure:

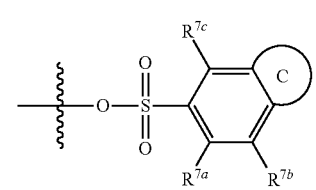

wherein: $R^{7a}$, $R^{7b}$ and $R^{7c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy) alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidine and guanidinoalkyl; and C can be selected from: a mono-substituted, a poly-substituted or an unsubstituted variant of the following residues: heterocyclyl, aryl, heteroaryl, cycloalkyl and cycloalkenyl.

In some embodiments, C can be a mono-substituted, a poly-substituted or an unsubstituted heterocyclyl ring. In an embodiment, C can be a poly-substituted heterocyclyl ring. In some embodiments, including those of this paragraph, $R^{7a}$, $R^{7b}$ and $R^{7c}$ can each be a $C_{1-24}$ alkyl (for example, $C_{1-6}$ alkyl such as methyl). In other embodiments, including those of this paragraph, $R^{7a}$, $R^{7b}$ and $R^{7c}$ can each be hydrogen.

An example of $R^1$ with the structure

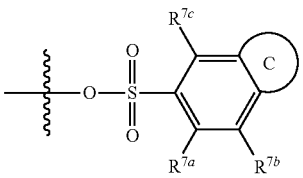

is

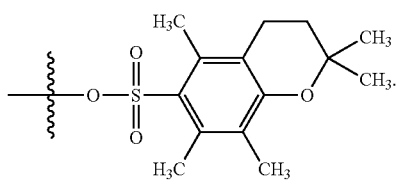

In other embodiments, C can be a mono-substituted, a poly-substituted or an unsubstituted aryl ring, such as a mono-substituted, a poly-substituted or an unsubstituted phenyl. In an embodiment, C can be an unsubstituted phenyl. In still other embodiments, C can be a mono-substituted, a poly-substituted or an unsubstituted heteroaryl ring. In yet still other embodiments, C can be a mono-substituted, a poly-substituted or an unsubstituted cycloalkyl ring. In some embodiments, C can be a mono-substituted, a poly-substituted or an unsubstituted cycloalkenyl ring. In some embodiments, including those of this paragraph, $R^{7a}$, $R^{7b}$ and $R^{7c}$ can be each hydrogen. As an example, when C is a mono-substituted, a poly-substituted or an unsubstituted aryl ring, $R^{7a}$, $R^{7b}$ and $R^{7c}$ can be each hydrogen.

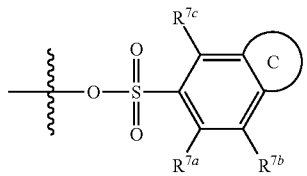

An example of $R^1$ of with the structure is

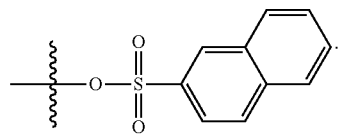 [SMILES: *OS(=O)(=O)c1ccc2ccccc2c1]

In some embodiments, $R^1$ can have the structure:

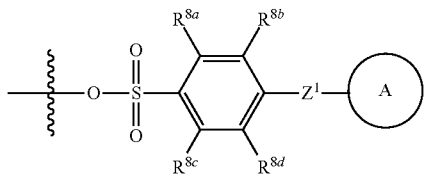

wherein: $R^{8a}$, $R^{8b}$, $R^{8c}$ and $R^{8d}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy) alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, guanidinoalkyl and $—S(=O)_2O^-$; A can be selected from: a mono-substituted, a poly-substituted or an unsubstituted variant of the following residues: heterocyclyl, aryl, heteroaryl, cycloalkyl and cycloalkenyl; and $Z^1$ can be selected from: O, S, N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—C$(=O)N(R^{17})$, CH=CH—C(=O), $O(CH_2)_{1-6}O$, $O(CH_2)_{1-6}$ and $N(R^{17a})C(=O)N(R^{17b})$, wherein $R^{17}$, $R^{17a}$ and $R^{17b}$ are independently selected from: H, $C_{1-4}$ alkyl, a substituted or unsubstituted benzyl, an allyl, and t-butoxycarbonyl (t-BOC). In an embodiment, $R^{17}$, $R^{17a}$ and $R^{17b}$ can be independently H or $C_{1-4}$ alkyl.

When $R^1$ is

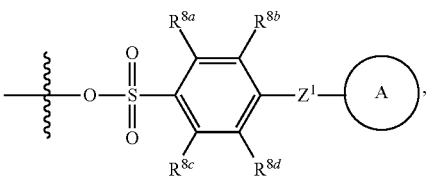

in some embodiments, A can be a mono-substituted, a poly-substituted or an unsubstituted aryl ring. For example, A can be a mono-substituted, a poly-substituted or an unsubstituted phenyl. In an embodiment, A can be an unsubstituted phenyl ring. In another embodiment, A can be a mono-substituted phenyl ring. In other embodiments, A can be a mono-substituted, a poly-substituted or an unsubstituted heteroaryl ring. In an embodiment, A can be an unsubstituted heteroaryl ring. In another embodiment, A can be a poly-substituted heteroaryl ring. In still other embodiments, A can be a mono-substituted, a poly-substituted or an unsubstituted heterocyclyl ring. In yet still other embodiments, A can be a mono-substituted, a poly-substituted or an unsubstituted cycloalkyl ring. In some embodiments, A can be a mono-substituted, a poly-substituted or an unsubstituted cycloalkenyl ring.

In some embodiments, $Z^1$ can be O (oxygen). In other embodiments, $Z^1$ can be N═N.

Examples of $R^1$ can have the structure:

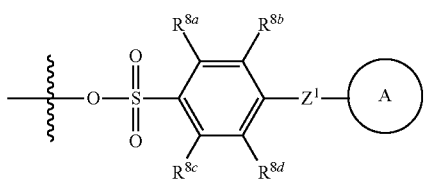

include, but are not limited to, the following:

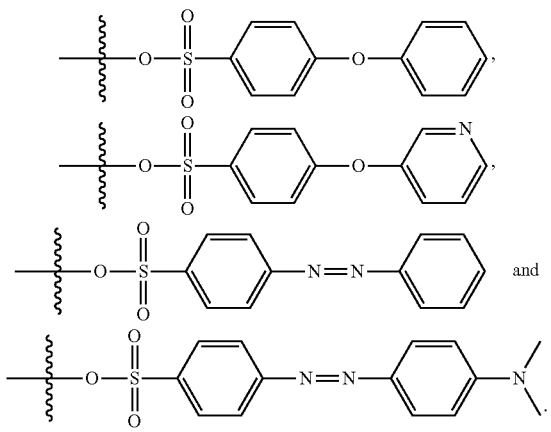

In any of the embodiments described with respect to $R^1$ having the structure:

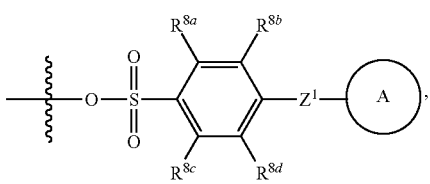

$R^{8a}$, $R^{8b}$, $R^{8b}$ and $R^{8d}$ can be each hydrogen.

In some embodiments, $R^1$ can have the structure

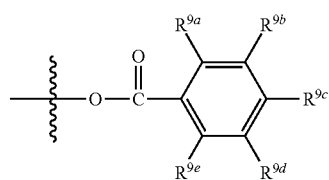

wherein: $R^{9a}$, $R^{9b}$, $R^{9c}$, $R^{9d}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, cycloalkyl, cycloalkenyl, cycloalkynyl, aryl, heteroaryl, heterocyclyl, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl.

In some embodiments, $R^{9a}$, $R^{9b}$, $R^{9c}$, $R^{9d}$, and $R^{9e}$ can be each independently selected from: hydrogen, halo, nitro, cyano, a mono-substituted, a poly-substituted or an unsubstituted variant of the following residues: $C_{1-24}$ alkyl, cycloalkyl, cycloalkenyl, aryl, heteroaryl, heterocyclyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, and hydroxy. In other embodiments, $R^{9a}$, $R^{9b}$, $R^{9c}$, $R^{9d}$, and $R^{9e}$ can be each independently selected from: hydrogen, halo, cyano, a mono-substituted, a poly-substituted or an unsubstituted $C_{1-24}$ alkyl, a mono-substituted, a poly-substituted or an unsubstituted aryl, amino, tri-haloalkyl, a mono-substituted, a poly-substituted or an unsubstituted alkoxy and hydroxy.

In some embodiments, when $R^1$ has the structure:

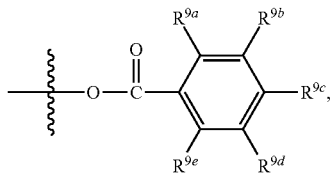

the phenyl ring of $R^1$ can be an unsubstituted phenyl ring, an ortho-substituted phenyl ring, a meta-substituted phenyl ring or a para-substituted phenyl ring. In some embodiments, at least one of $R^{9a}$, $R^{9b}$, $R^{9c}$, $R^{9d}$, and $R^{9e}$ is not hydrogen. In other embodiments, at least two of $R^{9a}$, $R^{9b}$, $R^{9c}$, $R^{9d}$, and $R^{9e}$ are not hydrogen. In still other embodiments, at least three of $R^{9a}$, $R^{9b}$, $R^{9c}$, $R^{9d}$, and $R^{9e}$ are not hydrogen. In yet sill other embodiments, at least four of $R^{9a}$, $R^{9b}$, $R^{9c}$, $R^{9d}$, and $R^{9e}$ are not hydrogen. In an embodiment, $R^{9c}$ is not hydrogen. For example, when $R^{9c}$ is not hydrogen, $R^{9c}$ can be selected from halogen, alkoxy, trihalolalkyl (for example, $CF_3$), cyano, $C_{1-8}$ alkyl, amino, hydroxy, and aryl. In an embodiment, when $R^{9c}$ is an aryl ring, the aryl ring can be an optionally substituted phenyl ring. In another embodiment, when $R^{9c}$ is an aryl ring, the aryl ring can be an unsubstituted phenyl ring. In some embodiments, at least one of $R^{9b}$ or $R^{9d}$ is not hydrogen. As an example, at least one of $R^{9b}$ or $R^{9d}$ can be a halogen. In other embodiments, $R^{9c}$ is not hydrogen and at least one of $R^{9b}$ or $R^{9d}$ is not hydrogen. Thus, the phenyl ring is a para- and meta-substituted phenyl ring. In some embodiments, $R^{9c}$ is not hydrogen and at least one of $R^{9a}$ or $R^{9e}$ is not hydrogen. Accordingly, the phenyl ring is a para- and ortho-substituted phenyl ring. As example, $R^{9e}$ can be a $C_{1-8}$ alkyl group and one or both of $R^{9a}$ and $R^{9e}$ can also be a $C_{1-8}$ alkyl group.

Examples of $R^1$ having the structure

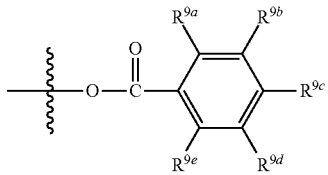

include, but are not limited to, the following:

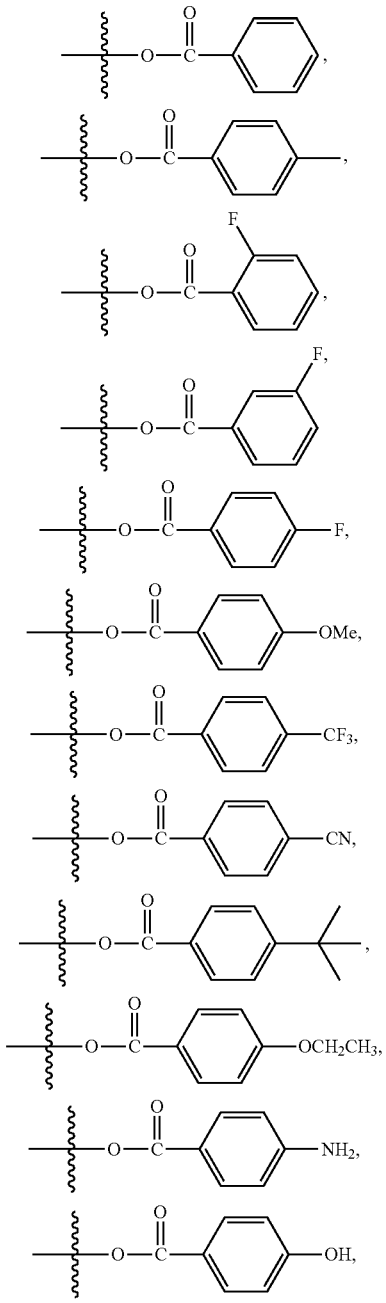

-continued

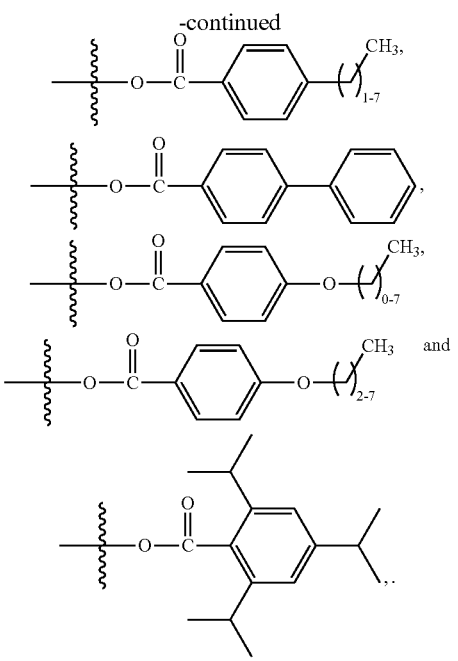

In some embodiments, $R^1$ can have the structure:

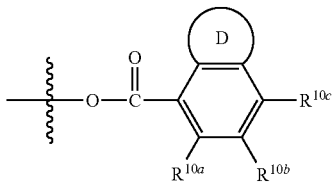

wherein: $R^{10a}$, $R^{10b}$ and $R^{10c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; and D can be selected from: a mono-substituted, a poly-substituted or an unsubstituted variant of the following residues: heterocyclyl, aryl, heteroaryl, cycloalkyl and cycloalkenyl.

In some embodiments, D can be a mono-substituted, a poly-substituted or an unsubstituted aryl ring, such as a mono-substituted, a poly-substituted or an unsubstituted phenyl. In an embodiment, D can be a mono-substituted phenyl. In another embodiment, D can be an unsubstituted phenyl. In other embodiments, D can be a mono-substituted, a poly-substituted or an unsubstituted heteroaryl ring. In still other embodiments, D can be a mono-substituted, a poly-substituted or an unsubstituted heterocyclyl ring. In yet still other embodiments, D can be a mono-substituted, a poly-substituted or an unsubstituted cycloalkyl ring. In some embodiments, D can be a mono-substituted, a poly-substituted or an unsubstituted cycloalkenyl ring. In some embodiments, including those of this paragraph, $R^{10a}$, $R^{10b}$ and $R^{10c}$ can be each hydrogen.

An example of $R^1$ is:

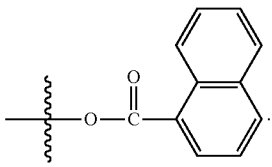

In some embodiments, $R^1$ can have the structure:

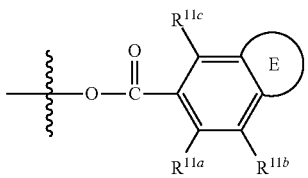

wherein: $R^{11a}$, $R^{11b}$ and $R^{11c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; and E can be selected from: a mono-substituted, a poly-substituted or an unsubstituted variant of the following residues: heterocyclyl, aryl, heteroaryl, cycloalkyl and cycloalkenyl.

In some embodiments, E can be a mono-substituted, a poly-substituted or an unsubstituted heteroaryl ring. In an embodiment, E can be a poly-substituted heteroaryl ring. In some embodiments, E can be a mono-substituted, a poly-substituted or an unsubstituted aryl ring. In an embodiment, E can be a mono-substituted, a poly-substituted or an unsubstituted phenyl ring. In still other embodiments, E can be a mono-substituted, a poly-substituted or an unsubstituted heterocyclyl ring. In yet still other embodiments, E can be a mono-substituted, a poly-substituted or an unsubstituted cycloalkyl ring. In some embodiments, E can be a mono-substituted, a poly-substituted or an unsubstituted cycloalkenyl ring. In some embodiments, including those described in the present paragraph, $R^{11a}$, $R^{11b}$ and $R^{11c}$ can be each hydrogen. In other embodiments, $R^{11a}$, $R^{11b}$ and $R^{11c}$ can be each $C_{1-4}$ alkyl.

A non-limiting list of examples where $R^1$ is

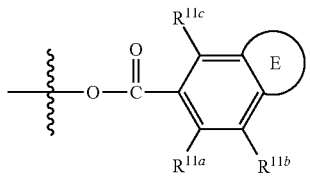

are:

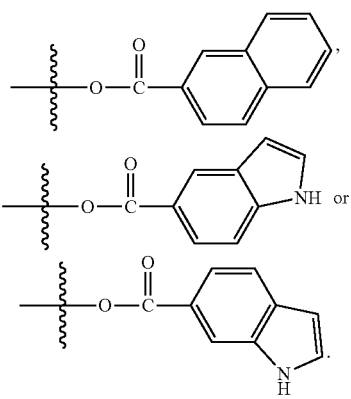

In some embodiments, $R^1$ can have the structure:

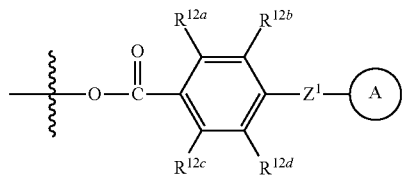

wherein: $R^{12a}$, $R^{12b}$, $R^{12c}$ and $R^{12d}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, guanidinoalkyl and —S(=O)$_2$O$^-$; A can be selected from: a mono-substituted, a poly-substituted or an unsubstituted variant of the following residues: heterocyclyl, aryl, heteroaryl, cycloalkyl and cycloalkenyl; and $Z^1$ can be selected from: O, S, N=N, O(CH$_2$)$_{1-6}$, S(O)$_2$N(R$^{17}$), S(O)$_2$N(R$^{17}$)(CH$_2$)$_{1-6}$, C(=O)N(R$^{17}$), N(R$^{17}$)C(=O), N(R$^{17}$)C(=O)(CH$_2$)$_{1-6}$, N(R$^{17}$)C(=O)O(CH$_2$)$_{1-6}$, S(O)$_2$, C(=O), (CH$_2$)$_{1-6}$C(=O), O(CH$_2$)$_{1-6}$C(=O), (CH$_2$)$_{1-6}$N(R$^{17}$)C(=O), CH=CH—C(=O)N(R$^{17}$), CH=CH—C(=O), O(CH$_2$)$_{1-6}$O, O(CH$_2$)$_{1-6}$ and N(R$^{17a}$)C(=O)N(R$^{17b}$), wherein R$^{17}$, R$^{17a}$ and R$^{17b}$ are independently selected from: H, C$_{1-4}$ alkyl, a substituted or unsubstituted benzyl, an allyl, and t-butoxycarbonyl (t-BOC). In some embodiments, R$^{17}$, R$^{17a}$ and R$^{17b}$ can be independently H or C$_{1-4}$ alkyl.

When R$^1$ is

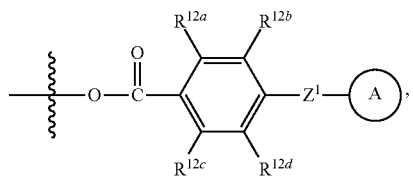

in some embodiments, A can be a mono-substituted, a poly-substituted or an unsubstituted aryl ring, for example, a mono-substituted, a poly-substituted or an unsubstituted phenyl. In an embodiment, A can be an unsubstituted phenyl. In another embodiment, A can be a mono-substituted phenyl. In some embodiments, A can be a mono-substituted, a poly-substituted or an unsubstituted heteroaryl ring. In an embodiment, A can be an unsubstituted heteroaryl ring. In another embodiment, A can be a poly-substituted heteroaryl ring. In other embodiments, A can be a mono-substituted, a poly-substituted or an unsubstituted heterocyclyl ring. In yet still other embodiments, A can be a mono-substituted, a poly-substituted or an unsubstituted cycloalkyl ring. In some embodiments, A can be a mono-substituted, a poly-substituted or an unsubstituted cycloalkenyl ring.

Likewise, when R$^1$ is

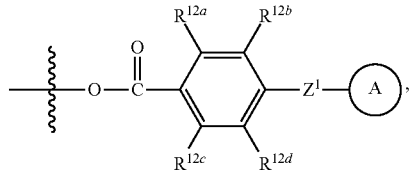

in an embodiment, Z$^1$ can be O (oxygen). In another embodiment, Z$^1$ can be O(CH$_2$)$_{1-6}$. In still another embodiment, Z$^1$ can be N=N.

In any of the embodiments described with respect to R$^1$ having the structure:

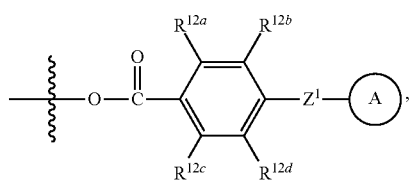

R$^{12a}$, R$^{12b}$, R$^{12c}$ and R$^{12d}$ can be each hydrogen.

Examples of

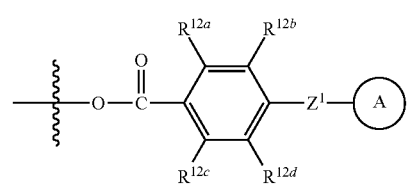

include, but are not limited to, the following:

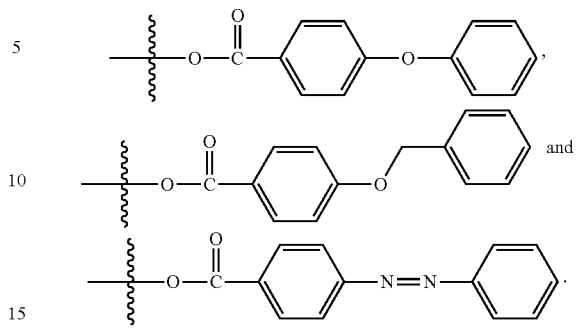

In some embodiments, R$^1$ can have the structure:

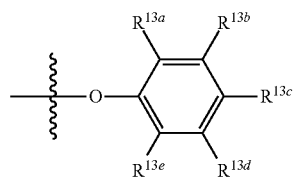

wherein R$^{13a}$, R$^{13b}$, R$^{13c}$, R$^{13d}$ and R$^{13e}$ can be each independently selected from: hydrogen, halo, nitro, cyano, a mono-substituted, a poly-substituted or an unsubstituted variant of the following residues: C$_{1-24}$ alkyl, C$_{2-24}$ alkenyl, C$_{2-24}$ alkynyl, mono-haloalkyl, di-haloalkyl, tri-haloalkyl, mono-haloalkoxy, di-haloalkoxy, tri-haloalkoxy, cycloalkyl, cycloalkenyl, cycloalkynyl, aryl, heteroaryl, heterocyclyl, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic ester-alkyl, sulfoalkyl, a salt of a sulfoalkyl, alkoxysulfonylalkyl, sulfooxyalkyl, a salt of a sulfooxyalkyl, alkoxysulfonyloxy-alkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl.

In some embodiments, R$^{13a}$, R$^{13b}$, R$^{13c}$, R$^{13d}$, and R$^{13e}$ can be each independently selected from: hydrogen, halo, nitro, cyano, a mono-substituted, a poly-substituted or an unsubstituted variant of the following residues: C$_{1-24}$ alkyl, cycloalkyl, cycloalkenyl, aryl, heteroaryl, heterocyclyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, carboxy and hydroxy.

In some embodiments, when R$^1$ has the structure:

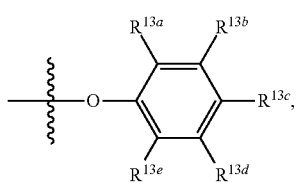

the phenyl ring of $R^1$ can be an unsubstituted phenyl ring, an ortho-substituted phenyl ring, a meta-substituted phenyl ring or a para-substituted phenyl ring. In some embodiments, at least one of $R^{13a}$, $R^{13b}$, $R^{13c}$, $R^{13d}$, and $R^{13e}$ is not hydrogen. In other embodiments, at least two of $R^{13a}$, $R^{13b}$, $R^{13c}$, $R^{13d}$, and $R^{13e}$ are not hydrogen. In still other embodiments, at least three of $R^{13a}$, $R^{13b}$, $R^{13c}$, $R^{13d}$, and $R^{13e}$ are not hydrogen. In yet sill other embodiments, at least four of $R^{13a}$, $R^{13b}$, $R^{13c}$, $R^{13d}$, and $R^{13e}$ are not hydrogen. In an embodiment, $R^{13c}$ is not hydrogen. In an embodiment, when $R^{13c}$ is an aryl ring, the aryl ring can be an optionally substituted phenyl ring. In another embodiment, when $R^{13c}$ is an aryl ring, the aryl ring can be an unsubstituted phenyl ring. In some embodiments, at least one of $R^{13b}$ or $R^{13d}$ is not hydrogen. In other embodiments, $R^{13c}$ is not hydrogen and at least one of $R^{13b}$ or $R^{13d}$ is not hydrogen. Accordingly, the phenyl ring is a para- and meta-substituted phenyl ring. In some embodiments, $R^{13c}$ is not hydrogen and at least one of $R^{13a}$ or $R^{13e}$ is not hydrogen. In an embodiment, the phenyl ring is a para- and ortho-substituted phenyl ring.

A non-limiting list of examples of $R^1$ when $R^1$ has the structure:

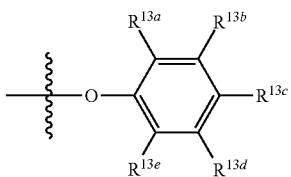

include the following:

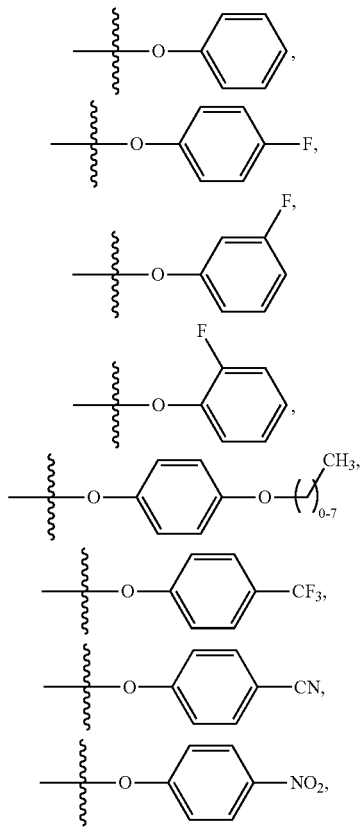

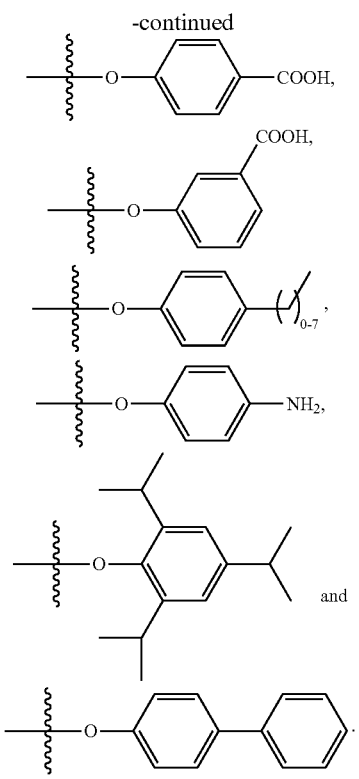

In some embodiments, $R^1$ can have the structure:

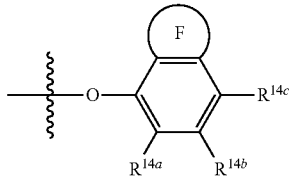

wherein: $R^{14a}$, $R^{14b}$ and $R^{14c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, salt of carboxyalkyl, alkylaminoalkyl, salt of an alkylaminoalkyl, dialkylaminoalkyl, salt of a dialkylaminoalkyl, alkylthioalkyl, arylthioalkyl, carboxy, alkylsulfonylalkyl, alkylsulfinylalkyl, alkoxysulfinylalkyl, thiocyanoalkyl, boronic acidalkyl, boronic esteralkyl, guanidinoalkyl, salt of a guanidinoalkyl, sulfoalkyl, salt of a sulfoalkyl, alkoxysulfonylalkyl, sulfooxyalkyl, salt of a sulfooxyalkyl, alkoxysulfonyloxyalkyl, phosphonooxyalkyl, salt of a phosphonooxyalkyl, (alkylphosphooxy)alkyl, phosphorylalkyl, salt of a phosphorylalkyl, (alkylphosphoryl)alkyl, pyridinylalkyl, salt of a pyridinylalkyl, salt of a heteroarylalkyl; and F can be selected from: a mono-substituted, a poly-substituted or an unsubstituted variant of the following residues: heterocyclyl, aryl, heteroaryl, cycloalkyl and cycloalkenyl.

In some embodiments, F can be a mono-substituted, a poly-substituted or an unsubstituted aryl ring such as a mono-substituted, a poly-substituted or an unsubstituted phenyl ring. In an embodiment, F can be a mono-substituted phenyl. In an other embodiment, F can be an unsubstituted phenyl. In other embodiments, F can be a mono-substituted, a poly-substituted or an unsubstituted heteroaryl ring. In still other embodiments, F can be a mono-substituted, a poly-substituted or an unsubstituted heterocyclyl ring. In yet still other embodiments, F can be a mono-substituted, a poly-substituted or an unsubstituted cycloalkyl ring. In some embodiments, F can be a mono-substituted, a poly-substituted or an unsubstituted cycloalkenyl ring. In some embodiment, including those of this paragraph, $R^{14a}$, $R^{14b}$ and $R^{14c}$ can be each hydrogen.

One example of

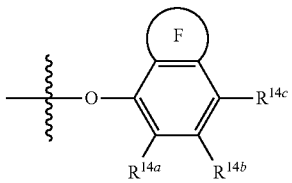

is

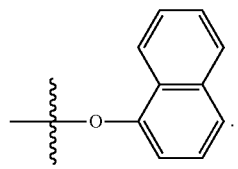 [SMILES: *Oc1cccc2ccccc12]

In some embodiments, $R^1$ can have the structure:

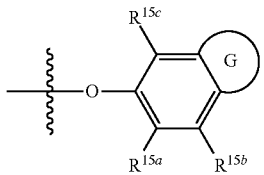

wherein: $R^{15a}$, $R^{15b}$ and $R^{15c}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphoryl alkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; and G can be selected from: a mono-substituted, a poly-substituted or an unsubstituted variant of the following residues: heterocyclyl, aryl, heteroaryl, cycloalkyl and cycloalkenyl.

In some embodiments, G can be a mono-substituted, a poly-substituted or an unsubstituted heterocyclyl ring. In other embodiments, G can be a mono-substituted, a poly-substituted or an unsubstituted heteroaryl ring. In still other embodiments, G can be a mono-substituted, a poly-substituted or an unsubstituted aryl ring (for example, a phenyl ring). In an embodiment, G can be an unsubstituted phenyl ring. In another embodiment, G can be a mono-substituted phenyl ring. In yet still other embodiments, G can be a mono-substituted, a poly-substituted or an unsubstituted cycloalkyl ring. In some embodiments, G can be a mono-substituted, a poly-substituted or an unsubstituted cycloalkenyl ring. In any embodiment, when $R^1$ is

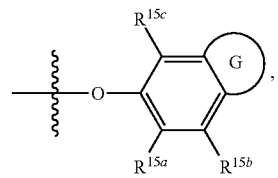

$R^{15a}$, $R^{15b}$ and $R^{15c}$ can be each hydrogen or a $C_{1-24}$ alkyl.

An example of

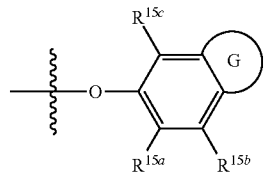

is

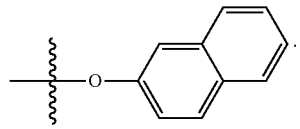

In some embodiments, $R^1$ can have the structure:

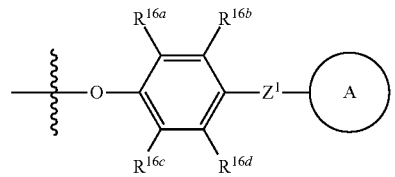

wherein: $R^{16a}$, $R^{16b}$, $R^{16c}$ and $R^{16d}$ can be each independently selected from: hydrogen, halo, nitro, cyano, a mono-substituted, a poly-substituted or an unsubstituted variant of the following residues: $C_{1-24}$ alkyl, $C_{2-24}$ alkenyl, $C_{2-24}$ alkynyl, mono-haloalkyl, di-haloalkyl, tri-haloalkyl, mono-haloalkoxy, di-haloalkoxy, tri-haloalkoxy, amino, mono-substituted amine, di-substituted amine, alkoxy, acyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy) alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, guanidinoalkyl and —S(=O)$_2$O$^-$; A can be selected from: a mono-substituted, a poly-substituted or an unsubstituted variant of the following residues: heterocyclyl, aryl, heteroaryl, cycloalkyl and cycloalkenyl; and $Z^1$ can be selected from: O, S, N=N, O(CH$_2$)$_{1-6}$, S(O)$_2$N(R$^{17}$), S(O)$_2$N(R$^{17}$)(CH$_2$)$_{1-6}$, C(=O)N(R$^{17}$), N(R$^{17}$)C(=O), N(R$^{17}$)C(=O)(CH$_2$)$_{1-6}$, N(R$^{17}$)C(=O)O(CH$_2$)$_{1-6}$, S(O)$_2$, C(=O), (CH$_2$)$_{1-6}$C(=O), O(CH$_2$)$_{1-6}$C(=O), (CH$_2$)$_{1-6}$ N(R$^{17}$)C(=O), CH=CH—C(=O)N(R$^{17}$), CH=CH—C(=O), O(CH$_2$)$_{1-6}$O, O(CH$_2$)$_{1-6}$ and N(R$^{17a}$)C(=O)N(R$^{17b}$), wherein R$^{17}$, R$^{17a}$ and R$^{17b}$ are independently selected from: H, $C_{1-4}$ alkyl, a substituted or unsubstituted benzyl, an allyl, and t-butoxycarbonyl (t-BOC). In an embodiment, R$^{17}$, R$^{17a}$ and R$^{17b}$ can be independently H or $C_{1-4}$ alkyl.

In some embodiments, when $R^1$ is

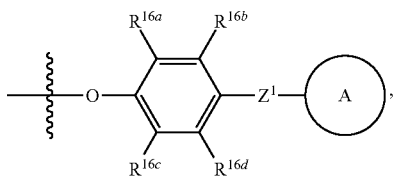

A can be a mono-substituted, a poly-substituted or an unsubstituted aryl ring, for example, a mono-substituted, a poly-substituted or an unsubstituted phenyl. In an embodiment, A can be an unsubstituted phenyl. In another embodiment, A can be a mono-substituted phenyl. In other embodiments, A can be a mono-substituted, a poly-substituted or an unsubstituted heteroaryl ring. In an embodiment, A can be an unsubstituted heteroaryl ring. In another embodiment, A can be a poly-substituted heteroaryl ring. In still other embodiments, A can be a mono-substituted, a poly-substituted or an unsubstituted heterocyclyl ring. In yet still other embodiments, A can be a mono-substituted, a poly-substituted or an unsubstituted cycloalkyl ring. In some embodiments, A can be a mono-substituted, a poly-substituted or an unsubstituted cycloalkenyl ring.

When $R^1$ is

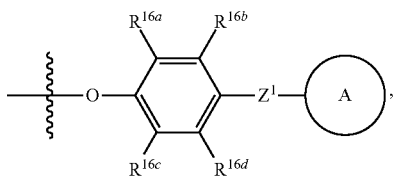

in some embodiments, $Z^1$ can be O. In other embodiments, $Z^1$ can be N=N. In any of the embodiments described with respect to $R^1$ having the structure:

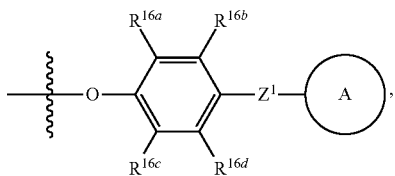

$R^{16a}$, $R^{16b}$, $R^{16c}$ and $R^{16d}$ can be each hydrogen.

In any embodiments described herein, $E^1$ and $E^3$ can be a substituted or unsubstituted heteroatom selected from O (oxygen) and S (sulfur); $E^2$ can be a substituted or unsubstituted N (nitrogen) or —CH$_2$—; $E^4$ can be a substituted or unsubstituted heteroatom selected from O, S, and N; and $E^5$ can be NH$_2$, SH or OH. In an embodiment, $E^5$ can be OH In some embodiments, including those described in the preceding paragraphs, $R^3$ can be selected from a mono-substituted, a poly-substituted or an unsubstituted variant of the following residues: $C_{1-6}$ alkyl, $C_{3-6}$ cycloalkyl, $C_{2-6}$ alkenyl, $C_{3-6}$ cycloalkenyl, aryl, and arylalkyl. In any of the embodiments described in this and any preceding paragraph, $R^2$ can be selected from a mono-substituted, a poly-substituted or an unsubstituted $C_1$-$C_{12}$ alkyl, a mono-substituted, a poly-substituted or an unsubstituted $C_3$-$C_{12}$ cycloalkyl, a mono-substituted, a poly-substituted or an unsubstituted $C_3$-$C_{12}$ cycloalkenyl and a mono-substituted, a poly-substituted or an unsubstituted aryl; and $R^3$ can be a mono-substituted, a poly-substituted or an unsubstituted $C_{1-6}$ alkyl. In an embodiment, $R^2$ can be an unsubstituted isopropyl or a cycloalkenyl; and $R^3$ can be methyl. In any of the embodiments described in this and any preceding paragraph, n can be 2.

Examples of

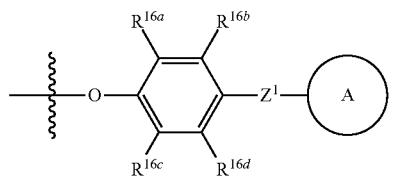

include, but are not limited to, the following:

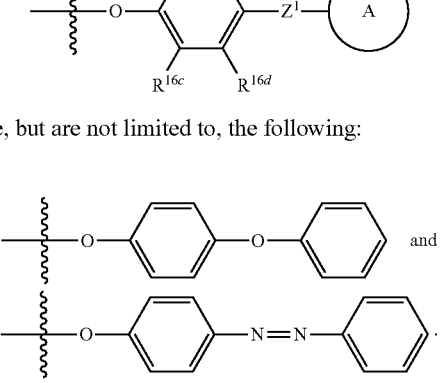

A non-limiting list of examples of compounds of Formula (I) are shown in the Table 1.

TABLE 1

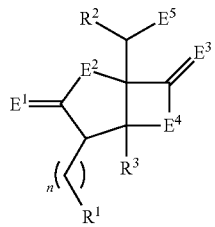

| $E^1/E^2/E^3/E^4/E^5$ | n | $R^1$ | $R^2$ | $R^3$ |
|---|---|---|---|---|
| O/NH/O/O/OH | 2 | 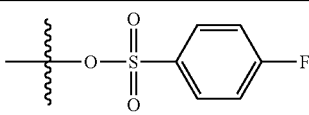 | 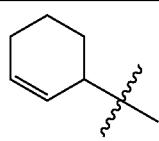 | CH$_3$ |

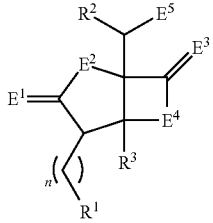

TABLE 1-continued

| E¹/E²/E³/E⁴/E⁵ | n | R¹ | R² | R³ |
|---|---|---|---|---|
| O/NH/O/O/OH | 2 | 4-tert-butylphenylsulfonate (–O–S(=O)₂–C₆H₄–C(CH₃)₃) | cyclohexenyl | CH₃ |
| O/NH/O/O/OH | 2 | 4-pentylphenylsulfonate | cyclohexenyl | CH₃ |
| O/NH/O/O/OH | 2 | 4-(hexadecyloxy)-3-(methoxycarbonyl)phenylsulfonate | cyclohexenyl | CH₃ |
| O/NH/O/O/OH | 2 | 4-(octadecylamino)-3-nitrophenylsulfonate | cyclohexenyl | CH₃ |
| O/NH/O/O/OH | 2 | 2,4,6-triisopropylphenylsulfonate | cyclohexenyl | CH₃ |
| O/NH/O/O/OH | 2 | naphthalene-1-sulfonate | cyclohexenyl | CH₃ |
| O/NH/O/O/OH | 2 | 5-(dimethylamino)naphthalene-1-sulfonate | cyclohexenyl | CH₃ |

TABLE 1-continued
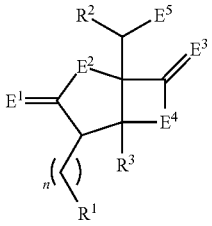
| $E^1/E^2/E^3/E^4/E^5$ | n | $R^1$ | $R^2$ | $R^3$ |
|---|---|---|---|---|
| O/NH/O/O/OH | 2 | 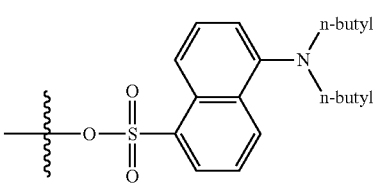 | 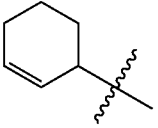 [SMILES: *C1C=CCCC1] | CH$_3$ |
| O/NH/O/O/OH | 2 | 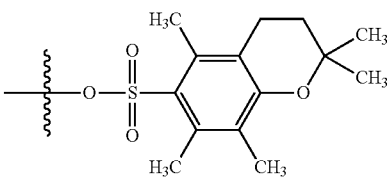 | 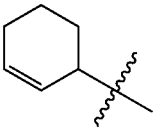 [SMILES: *C1C=CCCC1] | CH$_3$ |
| O/NH/O/O/OH | 2 | 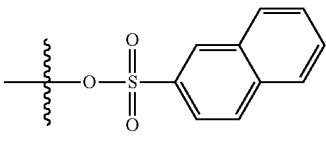 [SMILES: *OS(=O)(=O)c1ccc2ccccc2c1] | 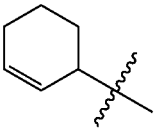 [SMILES: *C1C=CCCC1] | CH$_3$ |
| O/NH/O/O/OH | 2 | 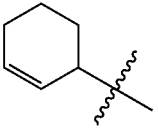 [SMILES: *C1C=CCCC1] | 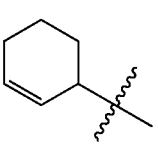 [SMILES: *C1C=CCCC1] | CH$_3$ |
| O/NH/O/O/OH | 2 | 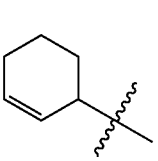 [SMILES: *C1C=CCCC1] | 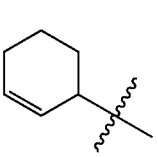 [SMILES: *C1C=CCCC1] | CH$_3$ |
| O/NH/O/O/OH | 2 | 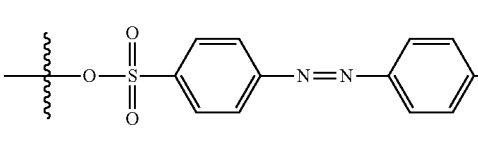 | 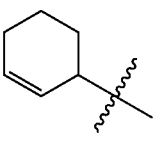 [SMILES: *C1C=CCCC1] | CH$_3$ |
| O/NH/O/O/OH | 2 | | | CH$_3$ |
| O/NH/O/O/OH | 2 | | | CH$_3$ |

TABLE 1-continued
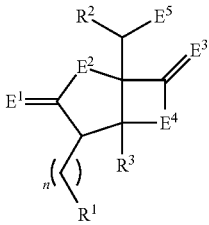

TABLE 1-continued
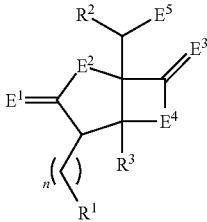
| E$^1$/E$^2$/E$^3$/E$^4$/E$^5$ | n | R$^1$ | R$^2$ | R$^3$ |
|---|---|---|---|---|
| O/NH/O/O/OH | 2 | 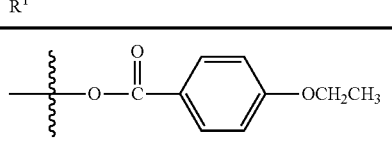 | 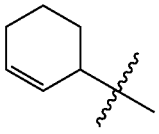 | CH$_3$ |
| O/NH/O/O/OH | 2 |  | 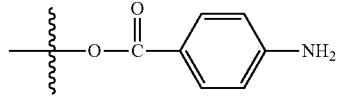 | CH$_3$ |
| O/NH/O/O/OH | 2 | 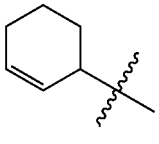 [SMILES: *C1C=CCCC1] |  | CH$_3$ |
| O/NH/O/O/OH | 2 | 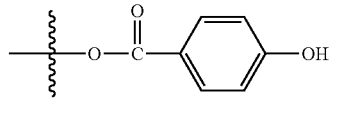 [SMILES: *OC(=O)c1ccc(C#N)cc1] | 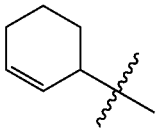 [SMILES: *C1C=CCCC1] | CH$_3$ |
| O/NH/O/O/OH | 2 |  | 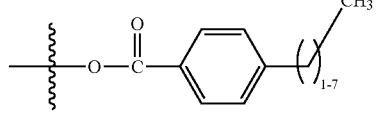 | CH$_3$ |
| O/NH/O/O/OH | 2 | 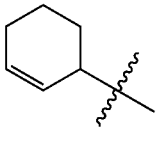 [SMILES: *C1C=CCCC1] |  | CH$_3$ |
| O/NH/O/O/OH | 2 | 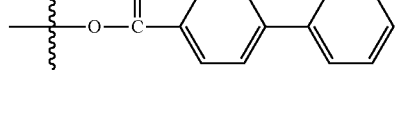 | 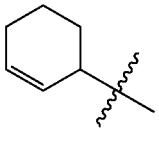 [SMILES: *C1C=CCCC1] | CH$_3$ |
| O/NH/O/O/OH | 2 |  | 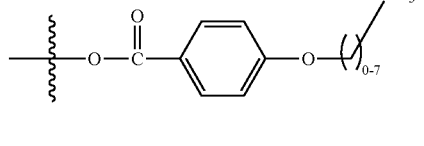 | CH$_3$ |

TABLE 1-continued
| $E^1/E^2/E^3/E^4/E^5$ | n | $R^1$ | $R^2$ | $R^3$ |
|---|---|---|---|---|
| O/NH/O/O/OH | 2 | 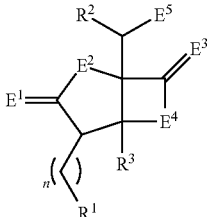 | 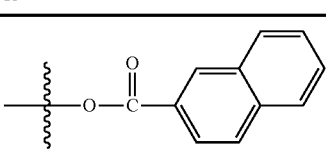 | CH₃ |
| O/NH/O/O/OH | 2 | 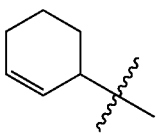 [SMILES: *C1C=CCCC1] | 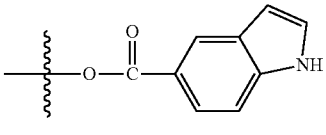 [SMILES: *OC(=O)c1ccc2[nH]ccc2c1] | CH₃ |
| O/NH/O/O/OH | 2 | 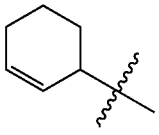 [SMILES: *C1C=CCCC1] | 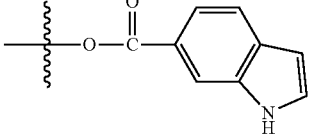 | CH₃ |
| O/NH/O/O/OH | 2 | 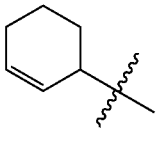 [SMILES: *C1C=CCCC1] | 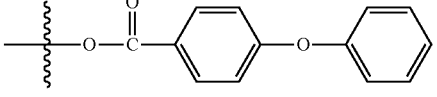 | CH₃ |
| O/NH/O/O/OH | 2 | 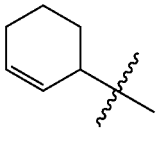 [SMILES: *C1C=CCCC1] | 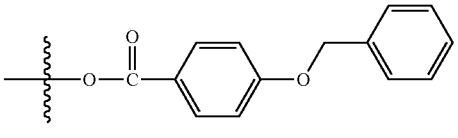 | CH₃ |
| O/NH/O/O/OH | 2 | 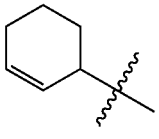 [SMILES: *C1C=CCCC1] | 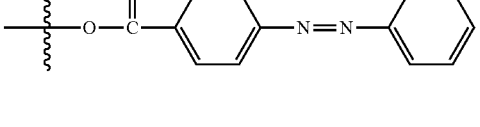 | CH₃ |
| O/NH/O/O/OH | 2 | 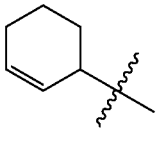 [SMILES: *C1C=CCCC1] | 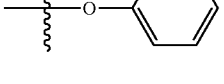 | CH₃ |
| O/NH/O/O/OH | 2 | 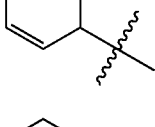 | 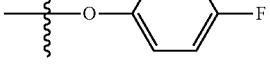 | CH₃ |
| O/NH/O/O/OH | 2 | 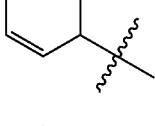 | 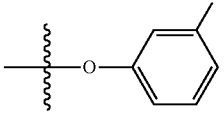 | CH₃ |

TABLE 1-continued

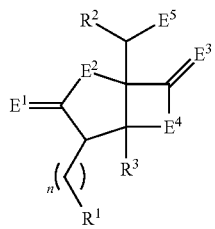

| E¹/E²/E³/E⁴/E⁵ | n | R¹ | R² | R³ |
|---|---|---|---|---|
| O/NH/O/O/OH | 2 | 2-fluorophenoxy | cyclohexenyl | CH₃ |
| O/NH/O/O/OH | 2 | 4-(alkyloxy)phenoxy, (CH₂)₀₋₇CH₃ | cyclohexenyl | CH₃ |
| O/NH/O/O/OH | 2 | 4-(trifluoromethyl)phenoxy | cyclohexenyl | CH₃ |
| O/NH/O/O/OH | 2 | 4-cyanophenoxy | cyclohexenyl | CH₃ |
| O/NH/O/O/OH | 2 | 4-nitrophenoxy | cyclohexenyl | CH₃ |
| O/NH/O/O/OH | 2 | 4-carboxyphenoxy | cyclohexenyl | CH₃ |
| O/NH/O/O/OH | 2 | 3-carboxyphenoxy | cyclohexenyl | CH₃ |
| O/NH/O/O/OH | 2 | 4-alkylphenoxy, (CH₂)₀₋₇CH₃ | cyclohexenyl | CH₃ |
| O/NH/O/O/OH | 2 | 4-aminophenoxy | cyclohexenyl | CH₃ |

TABLE 1-continued

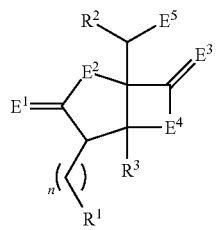

| $E^1/E^2/E^3/E^4/E^5$ | n | $R^1$ | $R^2$ | $R^3$ |
|---|---|---|---|---|
| O/NH/O/O/OH | 2 | 2,6-diisopropyl-4-isopropylphenoxy | cyclohexenyl | CH₃ |
| O/NH/O/O/OH | 2 | 1-naphthyloxy | cyclohexenyl | CH₃ |
| O/NH/O/O/OH | 2 | 2-naphthyloxy | cyclohexenyl | CH₃ |
| O/NH/O/O/OH | 2 | 4-phenylphenoxy | cyclohexenyl | CH₃ |
| O/NH/O/O/OH | 2 | 4-phenoxyphenoxy | cyclohexenyl | CH₃ |
| O/NH/O/O/OH | 2 | 4-(phenylazo)phenoxy | cyclohexenyl | CH₃ |
| O/NH/O/O/OH | 2 | 4-fluorophenylsulfonyloxy | cyclohexyl | CH₃ |
| O/NH/O/O/OH | 2 | 4-nitrophenylsulfonyloxy | cyclohexyl | CH₃ |

TABLE 1-continued

| E¹/E²/E³/E⁴/E⁵ | n | R¹ | R² | R³ |
|---|---|---|---|---|
| O/NH/O/O/OH | 2 | -O-SO₂-C₆H₄-CF₃ (para) | cyclohexyl | CH₃ |
| O/NH/O/O/OH | 2 | -O-SO₂-C₆H₄-OCF₃ (para) | cyclohexyl | CH₃ |
| O/NH/O/O/OH | 2 | -O-SO₂-C₆H₄-C(O)OH (para) | cyclohexyl | CH₃ |
| O/NH/O/O/OH | 2 | -O-SO₂-C₆H₄-C(O)OH (meta) | cyclohexyl | CH₃ |
| O/NH/O/O/OH | 2 | -O-SO₂-C₆H₄-Et (para) | cyclohexyl | CH₃ |
| O/NH/O/O/OH | 2 | -O-SO₂-C₆H₄-nPr (para) | cyclohexyl | CH₃ |
| O/NH/O/O/OH | 2 | -O-SO₂-C₆H₄-iPr (para) | cyclohexyl | CH₃ |
| O/NH/O/O/OH | 2 | -O-SO₂-C₆H₄-nBu (para) | cyclohexyl | CH₃ |
| O/NH/O/O/OH | 2 | -O-SO₂-C₆H₄-tBu (para) | cyclohexyl | CH₃ |

TABLE 1-continued
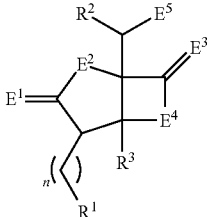
| $E^1/E^2/E^3/E^4/E^5$ | n | $R^1$ | $R^2$ | $R^3$ |
|---|---|---|---|---|
| O/NH/O/O/OH | 2 | 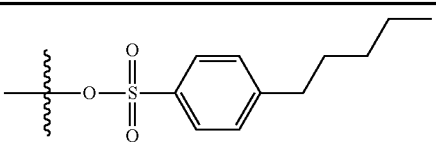 | 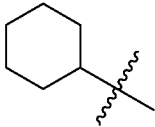 | $CH_3$ |
| O/NH/O/O/OH | 2 | 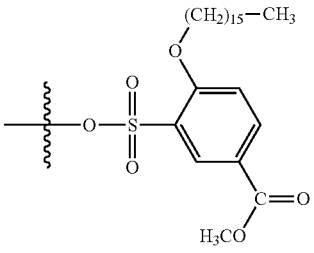 | 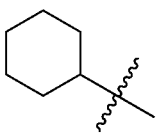 [SMILES: *C1CCCCC1] | $CH_3$ |
| O/NH/O/O/OH | 2 | 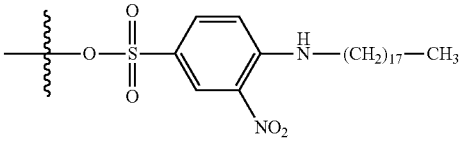 | 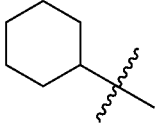 [SMILES: *C1CCCCC1] | $CH_3$ |
| O/NH/O/O/OH | 2 | 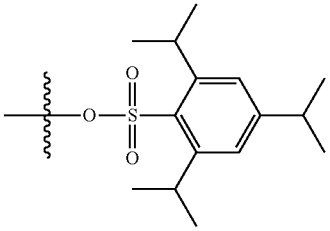 | 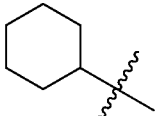 | $CH_3$ |
| O/NH/O/O/OH | 2 | 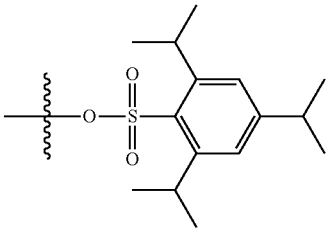 | 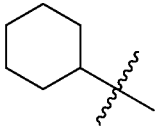 [SMILES: *C1CCCCC1] | $CH_3$ |
| O/NH/O/O/OH | 2 | 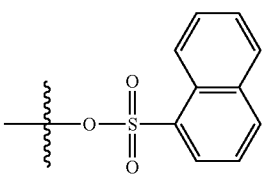 [SMILES: *OS(=O)(=O)c1cccc2ccccc12] | 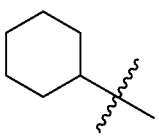 [SMILES: *C1CCCCC1] | $CH_3$ |
| O/NH/O/O/OH | 2 | 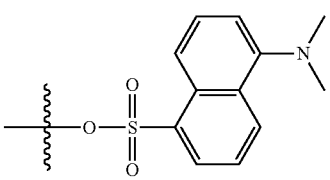 [SMILES: *OS(=O)(=O)c1cccc2c(N(C)C)cccc12] | 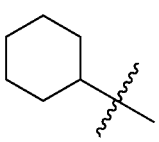 | $CH_3$ |

TABLE 1-continued
| E¹/E²/E³/E⁴/E⁵ | n | R¹ | R² | R³ |
|---|---|---|---|---|
| O/NH/O/O/OH | 2 | 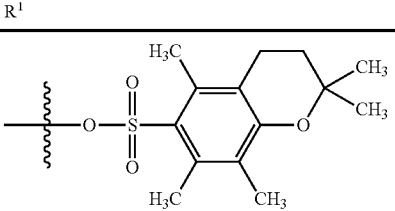 | 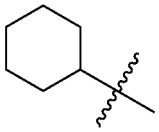 | CH₃ |
| O/NH/O/O/OH | 2 | 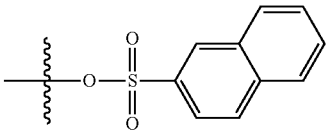 | 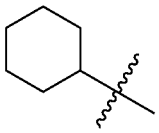 [SMILES: *C1CCCCC1] | CH₃ |
| O/NH/O/O/OH | 2 | 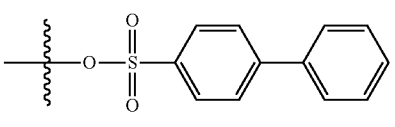 [SMILES: *OS(=O)(=O)c1ccc(-c2ccccc2)cc1] | 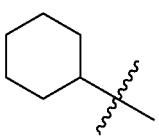 [SMILES: *C1CCCCC1] | CH₃ |
| O/NH/O/O/OH | 2 | 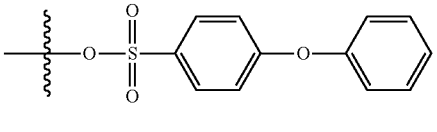 | 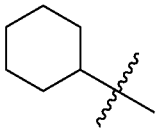 [SMILES: *C1CCCCC1] | CH₃ |
| O/NH/O/O/OH | 2 | 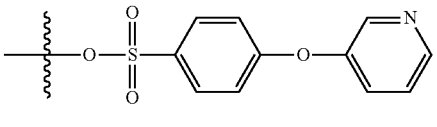 | 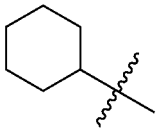 [SMILES: *C1CCCCC1] | CH₃ |
| O/NH/O/O/OH | 2 | 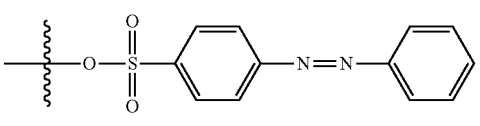 | 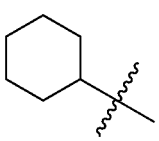 [SMILES: *C1CCCCC1] | CH₃ |
| O/NH/O/O/OH | 2 | 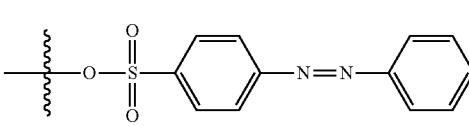 | 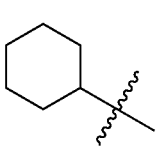 [SMILES: *C1CCCCC1] | CH₃ |
| O/NH/O/O/OH | 2 | 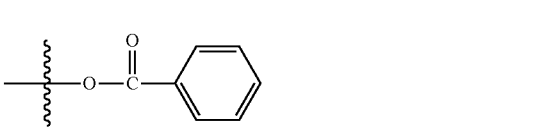 | 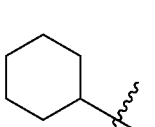 | CH₃ |
| O/NH/O/O/OH | 2 |  |  | CH₃ |

TABLE 1-continued
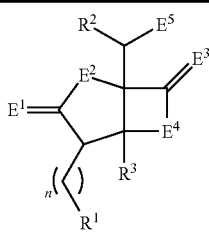
| E¹/E²/E³/E⁴/E⁵ | n | R¹ | R² | R³ |
|---|---|---|---|---|
| O/NH/O/O/OH | 2 | 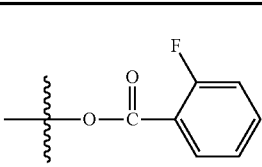 | 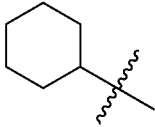 [SMILES: *C1CCCCC1] | CH₃ |
| O/NH/O/O/OH | 2 | 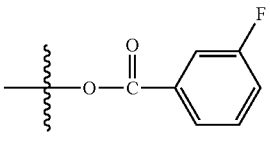 [SMILES: *OC(=O)c1cccc(F)c1] | 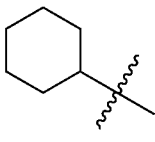 [SMILES: *C1CCCCC1] | CH₃ |
| O/NH/O/O/OH | 2 | 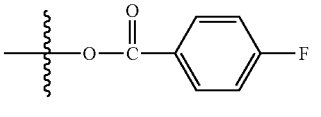 | 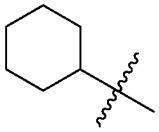 [SMILES: *C1CCCCC1] | CH₃ |
| O/NH/O/O/OH | 2 | 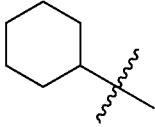 | 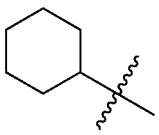 [SMILES: *C1CCCCC1] | CH₃ |
| O/NH/O/O/OH | 2 | 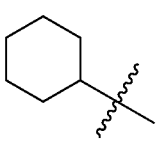 [SMILES: *C1CCCCC1] | 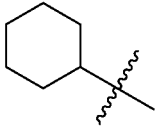 [SMILES: *C1CCCCC1] | CH₃ |
| O/NH/O/O/OH | 2 | 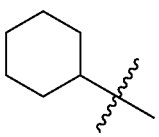 [SMILES: *C1CCCCC1] | 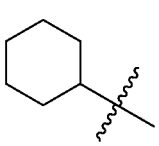 [SMILES: *C1CCCCC1] | CH₃ |
| O/NH/O/O/OH | 2 | | | CH₃ |
| O/NH/O/O/OH | 2 | | | CH₃ |
| O/NH/O/O/OH | 2 | | | CH₃ |

TABLE 1-continued
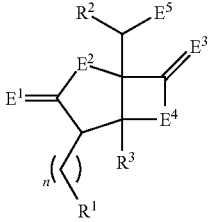
| E¹/E²/E³/E⁴/E⁵ | n | R¹ | R² | R³ |
|---|---|---|---|---|
| O/NH/O/O/OH | 2 | 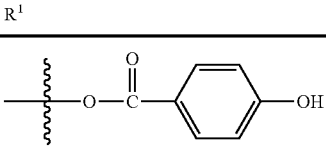 | 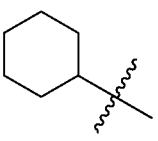 [SMILES: *C1CCCCC1] | CH₃ |
| O/NH/O/O/OH | 2 | 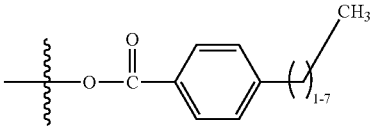 | 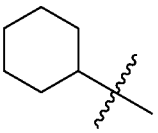 [SMILES: *C1CCCCC1] | CH₃ |
| O/NH/O/O/OH | 2 | 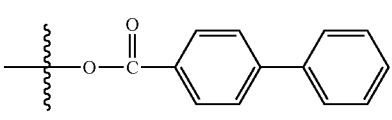 | 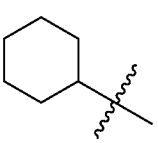 [SMILES: *C1CCCCC1] | CH₃ |
| O/NH/O/O/OH | 2 | 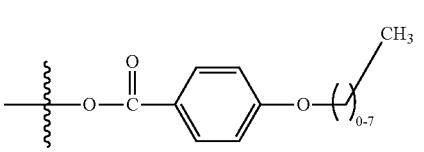 | 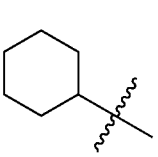 [SMILES: *C1CCCCC1] | CH₃ |
| O/NH/O/O/OH | 2 | 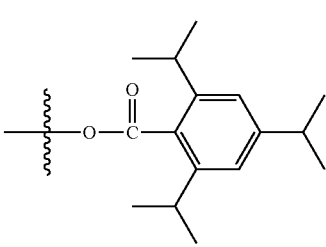 [SMILES: *OC(=O)c1c(C(C)C)cc(C(C)C)cc1C(C)C] | 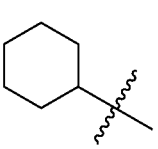 [SMILES: *C1CCCCC1] | CH₃ |
| O/NH/O/O/OH | 2 | 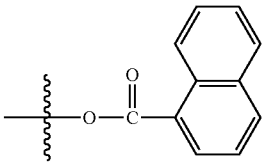 [SMILES: *OC(=O)c1cccc2ccccc12] | 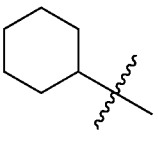 | CH₃ |
| O/NH/O/O/OH | 2 | 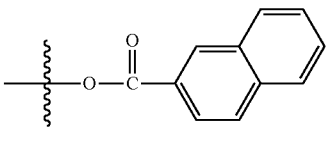 [SMILES: *OC(=O)c1ccc2ccccc2c1] | 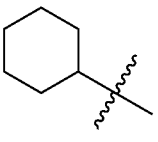 | CH₃ |
| O/NH/O/O/OH | 2 | 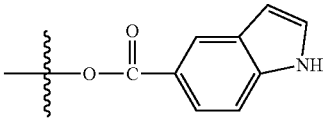 [SMILES: *OC(=O)c1ccc2[nH]ccc2c1] | 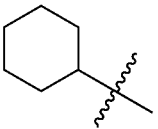 [SMILES: *C1CCCCC1] | CH₃ |

TABLE 1-continued

| $E^1/E^2/E^3/E^4/E^5$ | n | $R^1$ | $R^2$ | $R^3$ |
|---|---|---|---|---|
| O/NH/O/O/OH | 2 | indol-6-yl carboxylate (ester-linked to 1H-indole-6-carbonyl) | cyclohexyl | $CH_3$ |
| O/NH/O/O/OH | 2 | 4-phenoxybenzoate | cyclohexyl | $CH_3$ |
| O/NH/O/O/OH | 2 | 4-(benzyloxy)benzoate | cyclohexyl | $CH_3$ |
| O/NH/O/O/OH | 2 | 4-(phenyldiazenyl)benzoate | cyclohexyl | $CH_3$ |
| O/NH/O/O/OH | 2 | phenoxy | cyclohexyl | $CH_3$ |
| O/NH/O/O/OH | 2 | 4-fluorophenoxy | cyclohexyl | $CH_3$ |
| O/NH/O/O/OH | 2 | 3-fluorophenoxy | cyclohexyl | $CH_3$ |
| O/NH/O/O/OH | 2 | 2-fluoro-4-methylphenoxy | cyclohexyl | $CH_3$ |
| O/NH/O/O/OH | 2 | 4-(alkyl)phenoxy, $(CH_2)_{0-7}CH_3$ | cyclohexyl | $CH_3$ |

TABLE 1-continued

| $E^1/E^2/E^3/E^4/E^5$ | n | $R^1$ | $R^2$ | $R^3$ |
|---|---|---|---|---|
| O/NH/O/O/OH | 2 | -O-C₆H₄-CF₃ (para) | cyclohexyl | CH₃ |
| O/NH/O/O/OH | 2 | -O-C₆H₄-CN (para) | cyclohexyl | CH₃ |
| O/NH/O/O/OH | 2 | -O-C₆H₄-NO₂ (para) | cyclohexyl | CH₃ |
| O/NH/O/O/OH | 2 | -O-C₆H₄-COOH (para) | cyclohexyl | CH₃ |
| O/NH/O/O/OH | 2 | -O-C₆H₄-COOH (meta) | cyclohexyl | CH₃ |
| O/NH/O/O/OH | 2 | -O-C₆H₄-(CH₂)₀₋₇-CH₃ (para) | cyclohexyl | CH₃ |
| O/NH/O/O/OH | 2 | -O-C₆H₄-NH₂ (para) | cyclohexyl | CH₃ |
| O/NH/O/O/OH | 2 | -O-C₆H₂-(iPr)₃ (2,4,6-triisopropylphenoxy) | cyclohexyl | CH₃ |

TABLE 1-continued

| E¹/E²/E³/E⁴/E⁵ | n | R¹ | R² | R³ |
|---|---|---|---|---|
| O/NH/O/O/OH | 2 | –O–(1-naphthyl) | cyclohexyl | CH₃ |
| O/NH/O/O/OH | 2 | –O–(2-naphthyl) | cyclohexyl | CH₃ |
| O/NH/O/O/OH | 2 | –O–C₆H₄–C₆H₅ (4-biphenyl) | cyclohexyl | CH₃ |
| O/NH/O/O/OH | 2 | –O–C₆H₄–O–C₆H₅ | cyclohexyl | CH₃ |
| O/NH/O/O/OH | 2 | –O–C₆H₄–N=N–C₆H₅ | cyclohexyl | CH₃ |
| O/NH/O/O/OH | 2 | –O–SO₂–C₆H₄–F | isopropyl (CH(CH₃)₂-like) | CH₃ |
| O/NH/O/O/OH | 2 | –O–SO₂–C₆H₄–NO₂ | isopropyl | CH₃ |
| O/NH/O/O/OH | 2 | –O–SO₂–C₆H₄–CF₃ | isopropyl | CH₃ |
| O/NH/O/O/OH | 2 | –O–SO₂–C₆H₄–OCF₃ | isopropyl | CH₃ |

TABLE 1-continued
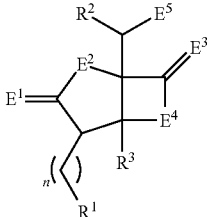
| E¹/E²/E³/E⁴/E⁵ | n | R¹ | R² | R³ |
|---|---|---|---|---|
| O/NH/O/O/OH | 2 | 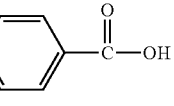 | 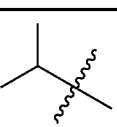 | CH₃ |
| O/NH/O/O/OH | 2 | 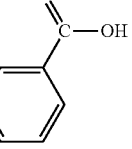 | 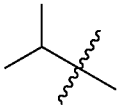 [SMILES: *C(C)C] | CH₃ |
| O/NH/O/O/OH | 2 | 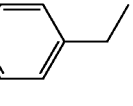 | 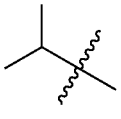 [SMILES: *C(C)C] | CH₃ |
| O/NH/O/O/OH | 2 | 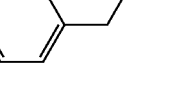 | 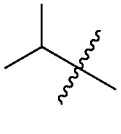 [SMILES: *C(C)C] | CH₃ |
| O/NH/O/O/OH | 2 | 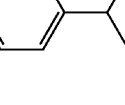 | 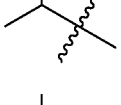 | CH₃ |
| O/NH/O/O/OH | 2 | 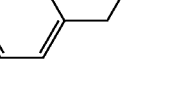 |  | CH₃ |
| O/NH/O/O/OH | 2 | 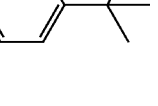 | 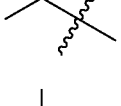 | CH₃ |
| O/NH/O/O/OH | 2 | 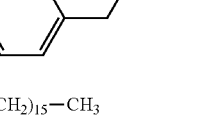 |  | CH₃ |
| O/NH/O/O/OH | 2 | 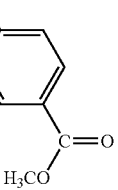 |  | CH₃ |

TABLE 1-continued
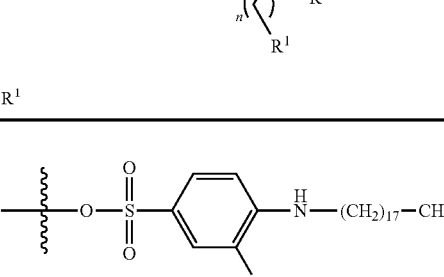
| E¹/E²/E³/E⁴/E⁵ | n | R¹ | R² | R³ |
|---|---|---|---|---|
| O/NH/O/O/OH | 2 | 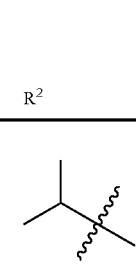 | 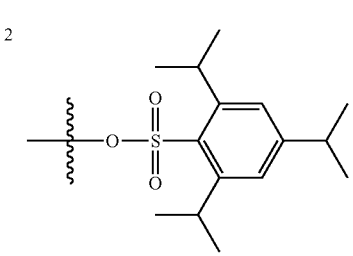 | CH₃ |
| O/NH/O/O/OH | 2 | 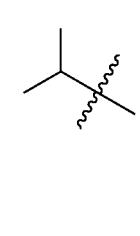 [SMILES: *C(C)C] | 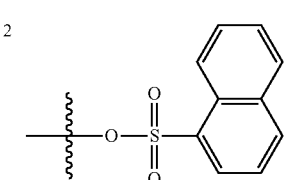 | CH₃ |
| O/NH/O/O/OH | 2 | 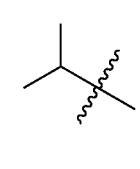 | 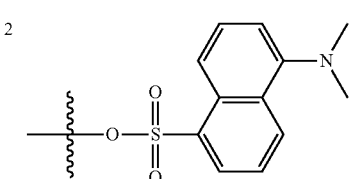 | CH₃ |
| O/NH/O/O/OH | 2 | 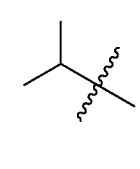 [SMILES: *C(C)C] | 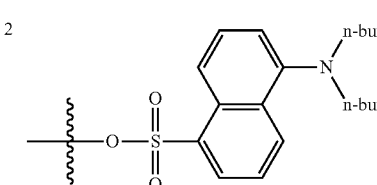 | CH₃ |
| O/NH/O/O/OH | 2 | 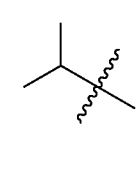 | 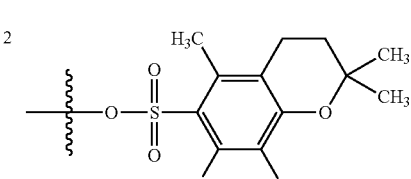 | CH₃ |
| O/NH/O/O/OH | 2 | 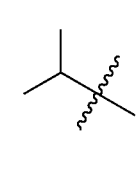 | 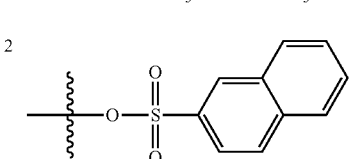 | CH₃ |
| O/NH/O/O/OH | 2 | 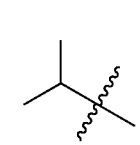 [SMILES: *C(C)C] | | CH₃ |

TABLE 1-continued
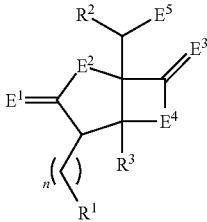
| E¹/E²/E³/E⁴/E⁵ | n | R¹ | R² | R³ |
|---|---|---|---|---|
| O/NH/O/O/OH | 2 |  | 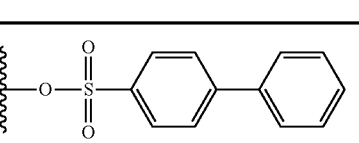 | CH₃ |
| O/NH/O/O/OH | 2 | 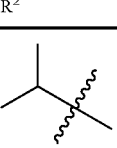 | 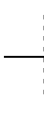 | CH₃ |
| O/NH/O/O/OH | 2 | 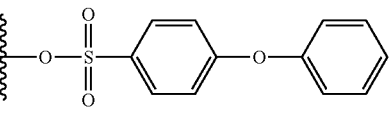 | 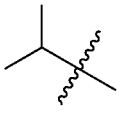 [SMILES: *C(C)C] | CH₃ |
| O/NH/O/O/OH | 2 |  | 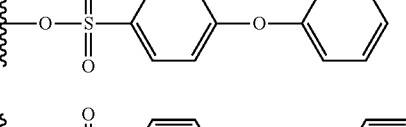 | CH₃ |
| O/NH/O/O/OH | 2 | 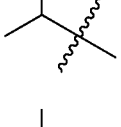 |  | CH₃ |
| O/NH/O/O/OH | 2 | 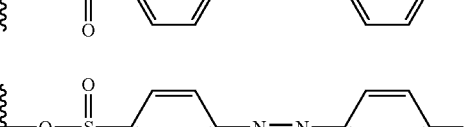 | 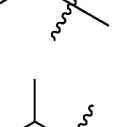 | CH₃ |
| O/NH/O/O/OH | 2 |  | 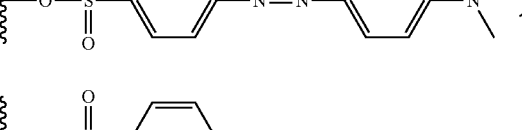 | CH₃ |
| O/NH/O/O/OH | 2 | 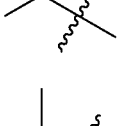 |  | CH₃ |
| O/NH/O/O/OH | 2 | 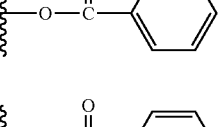 | 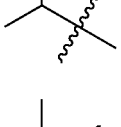 | CH₃ |
| O/NH/O/O/OH | 2 |  | 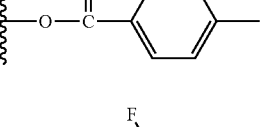 | CH₃ |

TABLE 1-continued
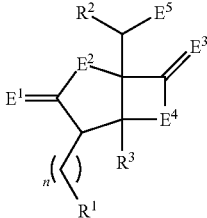
| E¹/E²/E³/E⁴/E⁵ | n | R¹ | R² | R³ |
|---|---|---|---|---|
| O/NH/O/O/OH | 2 | 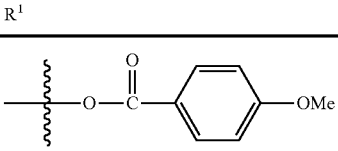 | 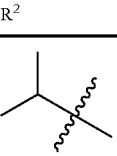 | CH₃ |
| O/NH/O/O/OH | 2 | 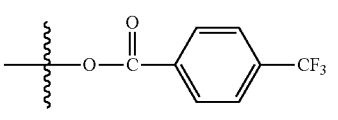 | 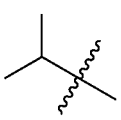 [SMILES: *C(C)C] | CH₃ |
| O/NH/O/O/OH | 2 | 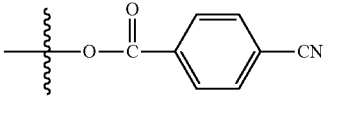 | 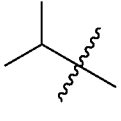 | CH₃ |
| O/NH/O/O/OH | 2 | 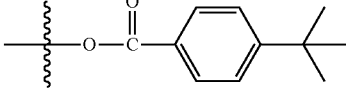 | 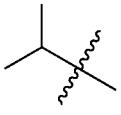 [SMILES: *C(C)C] | CH₃ |
| O/NH/O/O/OH | 2 | 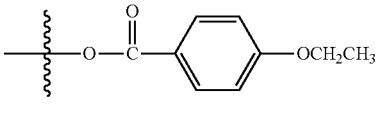 | 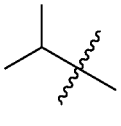 [SMILES: *C(C)C] | CH₃ |
| O/NH/O/O/OH | 2 | 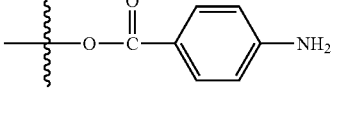 | 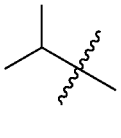 [SMILES: *C(C)C] | CH₃ |
| O/NH/O/O/OH | 2 | 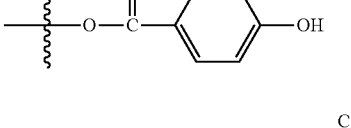 | 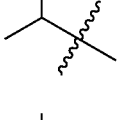 | CH₃ |
| O/NH/O/O/OH | 2 | 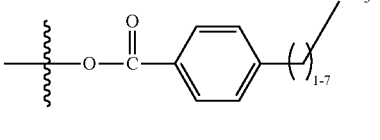 | 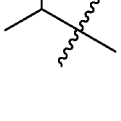 | CH₃ |
| O/NH/O/O/OH | 2 | 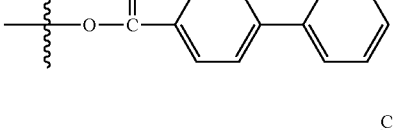 | 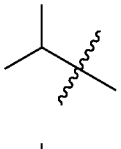 | CH₃ |
| O/NH/O/O/OH | 2 | 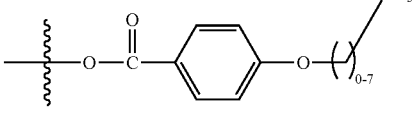 | 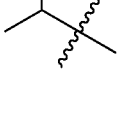 | CH₃ |

TABLE 1-continued
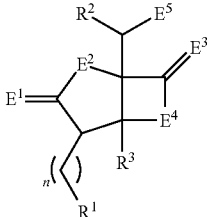
| E¹/E²/E³/E⁴/E⁵ | n | R¹ | R² | R³ |
|---|---|---|---|---|
| O/NH/O/O/OH | 2 | 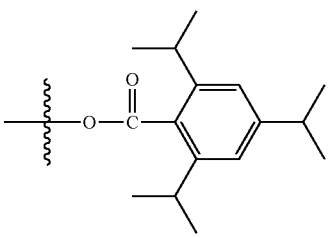 | 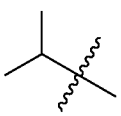 [SMILES: *C(C)C] | CH₃ |
| O/NH/O/O/OH | 2 | 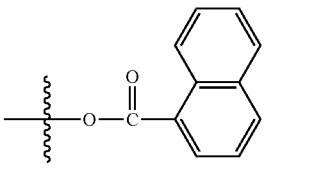 | 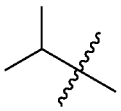 [SMILES: *C(C)C] | CH₃ |
| O/NH/O/O/OH | 2 | 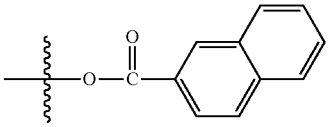 | 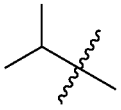 [SMILES: *C(C)C] | CH₃ |
| O/NH/O/O/OH | 2 | 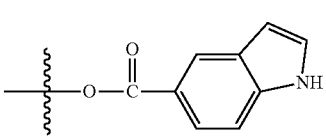 | 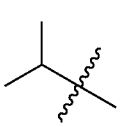 [SMILES: *C(C)C] | CH₃ |
| O/NH/O/O/OH | 2 | 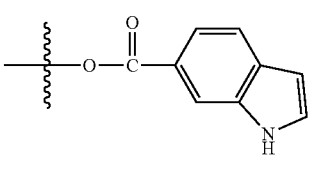 | 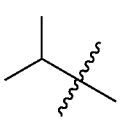 | CH₃ |
| O/NH/O/O/OH | 2 | 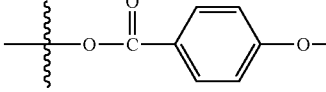 | 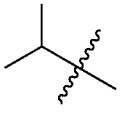 [SMILES: *C(C)C] | CH₃ |
| O/NH/O/O/OH | 2 | 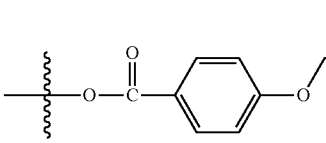 | 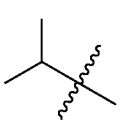 [SMILES: *C(C)C] | CH₃ |
| O/NH/O/O/OH | 2 | 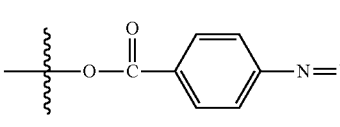 | 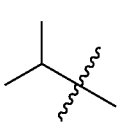 [SMILES: *C(C)C] | CH₃ |
| O/NH/O/O/OH | 2 | 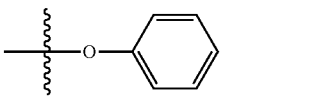 | 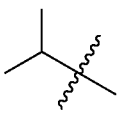 [SMILES: *C(C)C] | CH₃ |

TABLE 1-continued
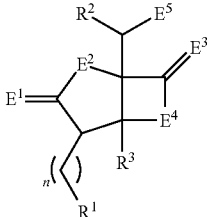
| E¹/E²/E³/E⁴/E⁵ | n | R¹ | R² | R³ |
|---|---|---|---|---|
| O/NH/O/O/OH | 2 | 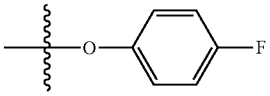 | 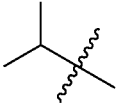 [SMILES: *C(C)C] | CH₃ |
| O/NH/O/O/OH | 2 | 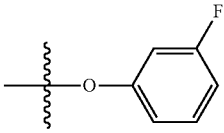 | 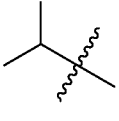 [SMILES: *C(C)C] | CH₃ |
| O/NH/O/O/OH | 2 | 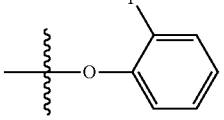 | 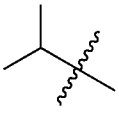 [SMILES: *C(C)C] | CH₃ |
| O/NH/O/O/OH | 2 | 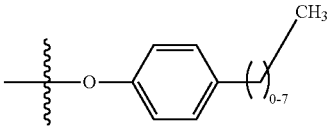 | 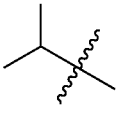 [SMILES: *C(C)C] | CH₃ |
| O/NH/O/O/OH | 2 | 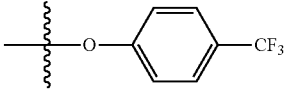 | 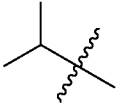 [SMILES: *C(C)C] | CH₃ |
| O/NH/O/O/OH | 2 | 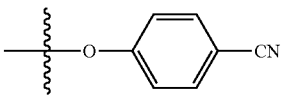 | 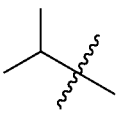 | CH₃ |
| O/NH/O/O/OH | 2 | 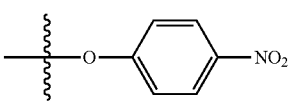 | 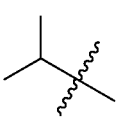 [SMILES: *C(C)C] | CH₃ |
| O/NH/O/O/OH | 2 | 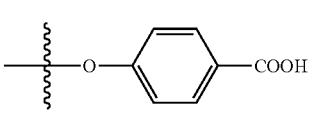 | 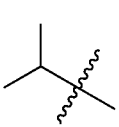 [SMILES: *C(C)C] | CH₃ |
| O/NH/O/O/OH | 2 | 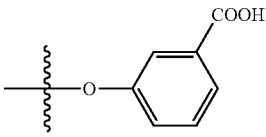 [SMILES: *Oc1cccc(C(=O)O)c1] | 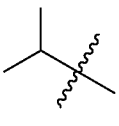 | CH₃ |
| O/NH/O/O/OH | 2 | 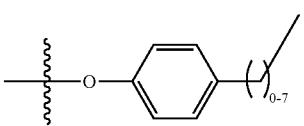 | 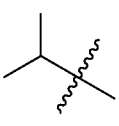 [SMILES: *C(C)C] | CH₃ |

TABLE 1-continued
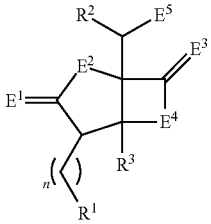
| E¹/E²/E³/E⁴/E⁵ | n | R¹ | R² | R³ |
|---|---|---|---|---|
| O/NH/O/O/OH | 2 | 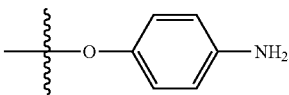 [SMILES: *Oc1ccc(N)cc1] | 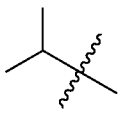 | CH₃ |
| O/NH/O/O/OH | 2 | 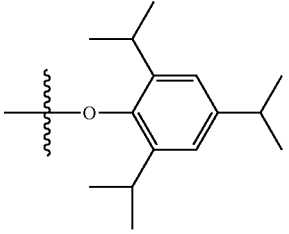 | 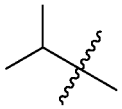 [SMILES: *C(C)C] | CH₃ |
| O/NH/O/O/OH | 2 | 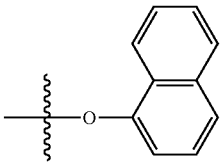 [SMILES: *Oc1cccc2ccccc12] | 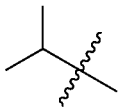 | CH₃ |
| O/NH/O/O/OH | 2 | 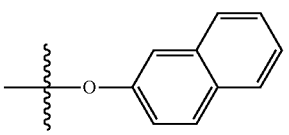 [SMILES: *Oc1ccc2ccccc2c1] | 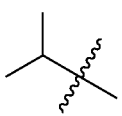 | CH₃ |
| O/NH/O/O/OH | 2 | 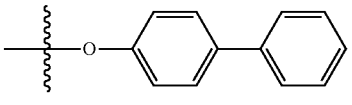 | 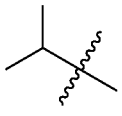 [SMILES: *C(C)C] | CH₃ |
| O/NH/O/O/OH | 2 | 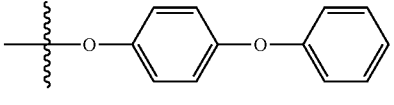 [SMILES: *Oc1ccc(Oc2ccccc2)cc1] | 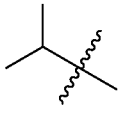 [SMILES: *C(C)C] | CH₃ |
| O/NH/O/O/OH | 2 | 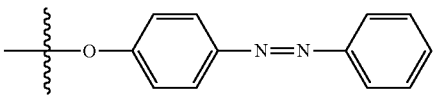 | 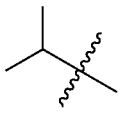 | CH₃ |
| O/NH/O/O/OH | 2 | 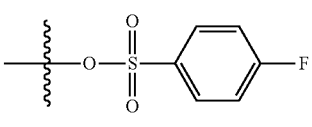 [SMILES: *OS(=O)(=O)c1ccc(F)cc1] | 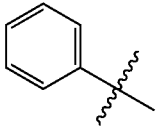 | CH₃ |

TABLE 1-continued
| E¹/E²/E³/E⁴/E⁵ | n | R¹ | R² | R³ |
|---|---|---|---|---|
| O/NH/O/O/OH | 2 | 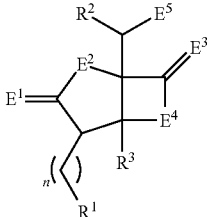 | 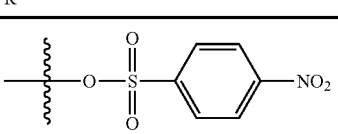 | CH₃ |
| O/NH/O/O/OH | 2 | 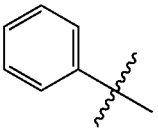 [SMILES: *c1ccccc1] | 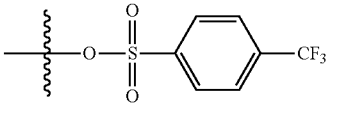 [SMILES: *OS(=O)(=O)c1ccc(C(F)(F)F)cc1] | CH₃ |
| O/NH/O/O/OH | 2 | 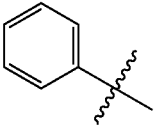 [SMILES: *c1ccccc1] | 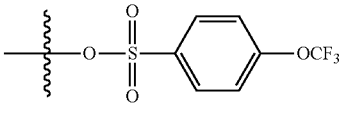 [SMILES: *OS(=O)(=O)c1ccc(OC(F)(F)F)cc1] | CH₃ |
| O/NH/O/O/OH | 2 | 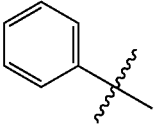 [SMILES: *c1ccccc1] | 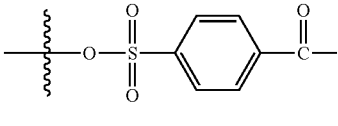 | CH₃ |
| O/NH/O/O/OH | 2 | 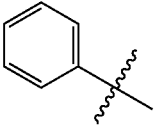 [SMILES: *c1ccccc1] | 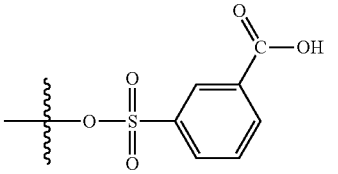 [SMILES: *OS(=O)(=O)c1cccc(C(=O)O)c1] | CH₃ |
| O/NH/O/O/OH | 2 | 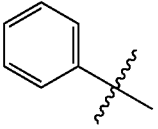 [SMILES: *c1ccccc1] | 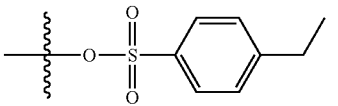 | CH₃ |
| O/NH/O/O/OH | 2 | 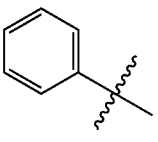 [SMILES: *c1ccccc1] | 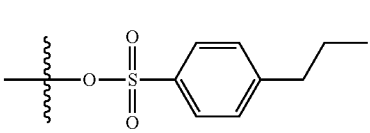 | CH₃ |
| O/NH/O/O/OH | 2 | 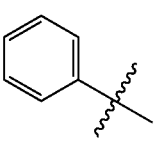 [SMILES: *c1ccccc1] | 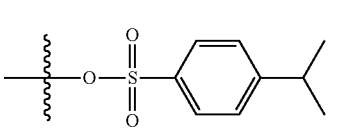 | CH₃ |
| O/NH/O/O/OH | 2 | 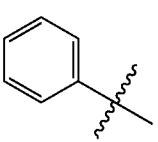 [SMILES: *c1ccccc1] | 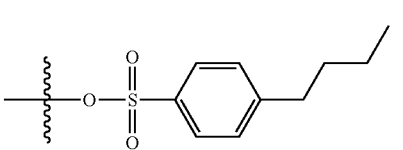 [SMILES: *OS(=O)(=O)c1ccc(CCCC)cc1] | CH₃ |

TABLE 1-continued

| E¹/E²/E³/E⁴/E⁵ | n | R¹ | R² | R³ |
|---|---|---|---|---|
| O/NH/O/O/OH | 2 | -O-S(O)₂-C₆H₄-C(CH₃)₃ (para-tert-butylphenyl sulfonate) | phenyl | CH₃ |
| O/NH/O/O/OH | 2 | -O-S(O)₂-C₆H₄-(CH₂)₄CH₃ (para-pentylphenyl sulfonate) | phenyl | CH₃ |
| O/NH/O/O/OH | 2 | -O-S(O)₂-aryl with 4-O(CH₂)₁₅CH₃ and CO₂CH₃ substituents | phenyl | CH₃ |
| O/NH/O/O/OH | 2 | -O-S(O)₂-C₆H₃(NO₂)(NH(CH₂)₁₇CH₃) | phenyl | CH₃ |
| O/NH/O/O/OH | 2 | -O-S(O)₂-2,4,6-triisopropylphenyl | phenyl | CH₃ |
| O/NH/O/O/OH | 2 | -O-S(O)₂-(naphthalen-1-yl) | phenyl | CH₃ |
| O/NH/O/O/OH | 2 | -O-S(O)₂-(5-(dimethylamino)naphthalen-1-yl) | phenyl | CH₃ |

TABLE 1-continued
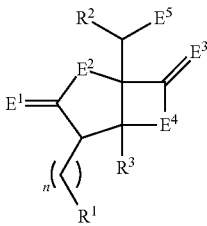
| $E^1/E^2/E^3/E^4/E^5$ | n | $R^1$ | $R^2$ | $R^3$ |
|---|---|---|---|---|
| O/NH/O/O/OH | 2 | 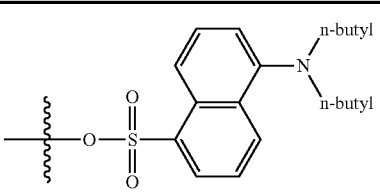 | 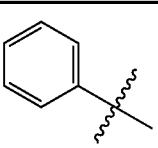 | $CH_3$ |
| O/NH/O/O/OH | 2 | 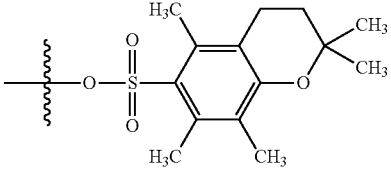 [SMILES: *OS(=O)(=O)c1c(C)c(C)c2c(c1C)CCC(C)(C)O2] | 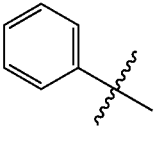 [SMILES: *c1ccccc1] | $CH_3$ |
| O/NH/O/O/OH | 2 | 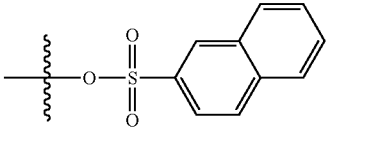 [SMILES: *OS(=O)(=O)c1ccc2ccccc2c1] | 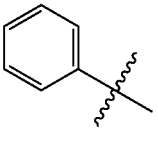 [SMILES: *c1ccccc1] | $CH_3$ |
| O/NH/O/O/OH | 2 | 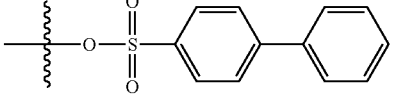 | 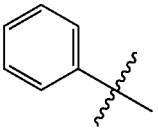 [SMILES: *c1ccccc1] | $CH_3$ |
| O/NH/O/O/OH | 2 | 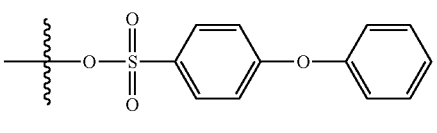 | 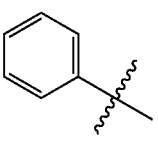 [SMILES: *c1ccccc1] | $CH_3$ |
| O/NH/O/O/OH | 2 | 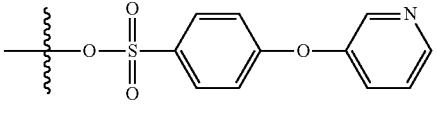 | 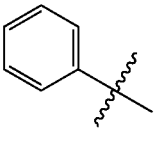 [SMILES: *c1ccccc1] | $CH_3$ |
| O/NH/O/O/OH | 2 | 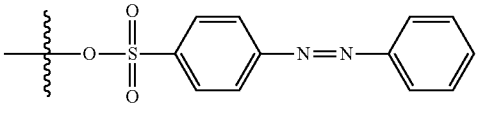 | 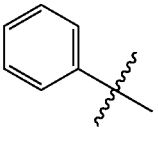 [SMILES: *c1ccccc1] | $CH_3$ |
| O/NH/O/O/OH | 2 | 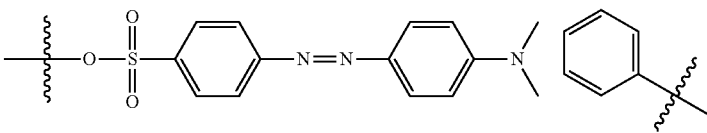 | 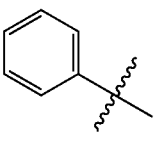 [SMILES: *c1ccccc1] | $CH_3$ |

TABLE 1-continued
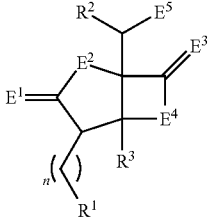
| E¹/E²/E³/E⁴/E⁵ | n | R¹ | R² | R³ |
|---|---|---|---|---|
| O/NH/O/O/OH | 2 | 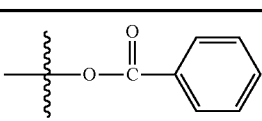 | 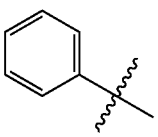 | CH₃ |
| O/NH/O/O/OH | 2 | 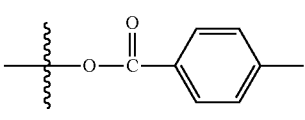 | 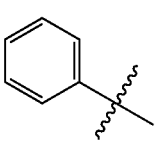 [SMILES: *c1ccccc1] | CH₃ |
| O/NH/O/O/OH | 2 | 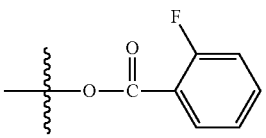 [SMILES: *OC(=O)c1ccccc1F] | 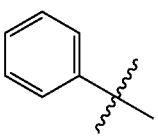 [SMILES: *c1ccccc1] | CH₃ |
| O/NH/O/O/OH | 2 | 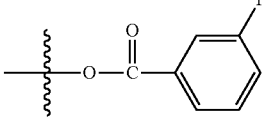 | 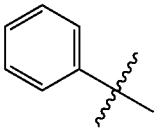 [SMILES: *c1ccccc1] | CH₃ |
| O/NH/O/O/OH | 2 | 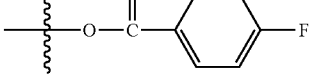 | 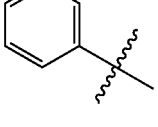 | CH₃ |
| O/NH/O/O/OH | 2 | 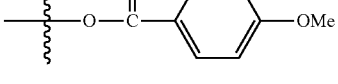 | 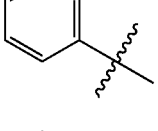 | CH₃ |
| O/NH/O/O/OH | 2 | 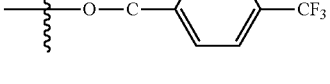 | 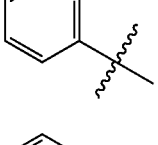 | CH₃ |
| O/NH/O/O/OH | 2 | 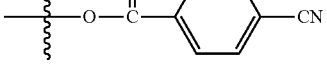 | 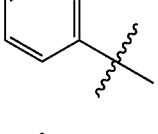 | CH₃ |
| O/NH/O/O/OH | 2 | 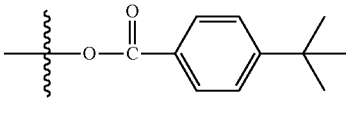 | 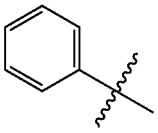 [SMILES: *c1ccccc1] | CH₃ |

TABLE 1-continued
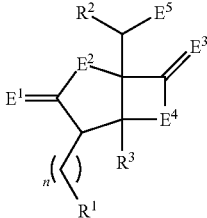
| E$^1$/E$^2$/E$^3$/E$^4$/E$^5$ | n | R$^1$ | R$^2$ | R$^3$ |
|---|---|---|---|---|
| O/NH/O/O/OH | 2 | 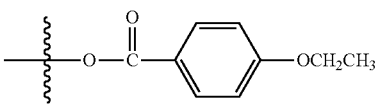 [SMILES: *OC(=O)c1ccc(OCC)cc1] | 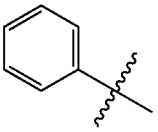 [SMILES: *c1ccccc1] | CH$_3$ |
| O/NH/O/O/OH | 2 | 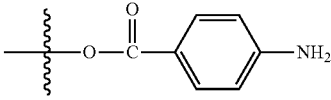 [SMILES: *OC(=O)c1ccc(N)cc1] | 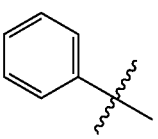 [SMILES: *c1ccccc1] | CH$_3$ |
| O/NH/O/O/OH | 2 | 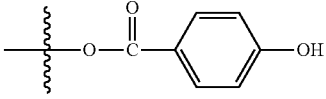 [SMILES: *OC(=O)c1ccc(O)cc1] | 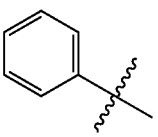 [SMILES: *c1ccccc1] | CH$_3$ |
| O/NH/O/O/OH | 2 | 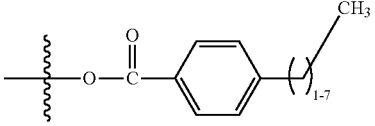 | 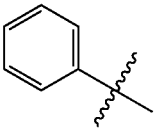 [SMILES: *c1ccccc1] | CH$_3$ |
| O/NH/O/O/OH | 2 | 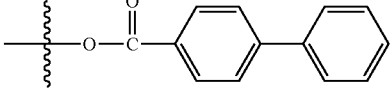 | 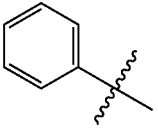 [SMILES: *c1ccccc1] | CH$_3$ |
| O/NH/O/O/OH | 2 | 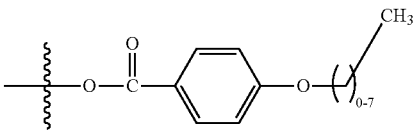 | 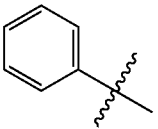 | CH$_3$ |
| O/NH/O/O/OH | 2 | 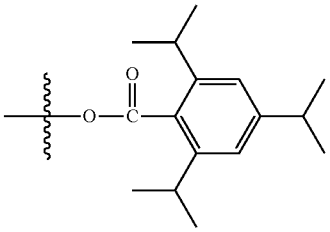 [SMILES: *OC(=O)c1c(C(C)C)cc(C(C)C)cc1C(C)C] | 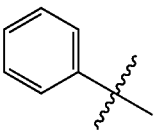 [SMILES: *c1ccccc1] | CH$_3$ |
| O/NH/O/O/OH | 2 | 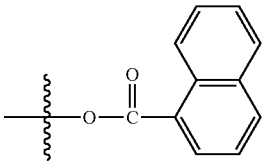 [SMILES: *OC(=O)c1cccc2ccccc12] | 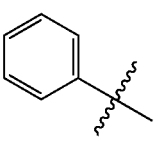 [SMILES: *c1ccccc1] | CH$_3$ |

TABLE 1-continued
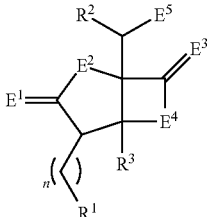
| E¹/E²/E³/E⁴/E⁵ | n | R¹ | R² | R³ |
|---|---|---|---|---|
| O/NH/O/O/OH | 2 | 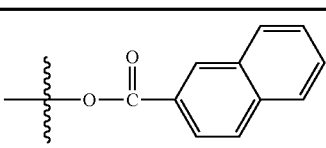 | 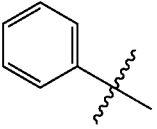 [SMILES: *c1ccccc1] | CH₃ |
| O/NH/O/O/OH | 2 | 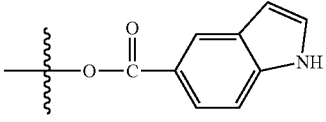 [SMILES: *OC(=O)c1ccc2[nH]ccc2c1] | 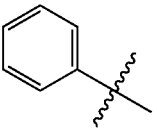 [SMILES: *c1ccccc1] | CH₃ |
| O/NH/O/O/OH | 2 | 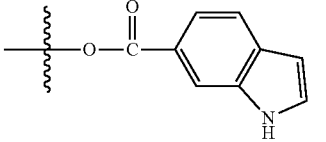 | 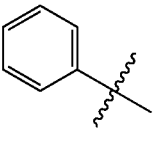 [SMILES: *c1ccccc1] | CH₃ |
| O/NH/O/O/OH | 2 | 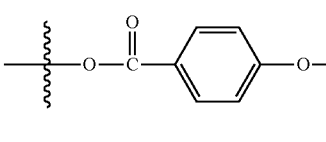 | 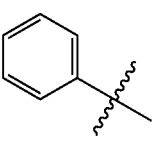 [SMILES: *c1ccccc1] | CH₃ |
| O/NH/O/O/OH | 2 | 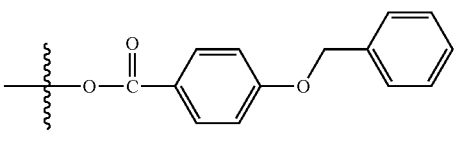 | 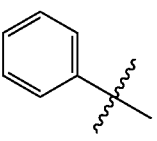 | CH₃ |
| O/NH/O/O/OH | 2 | 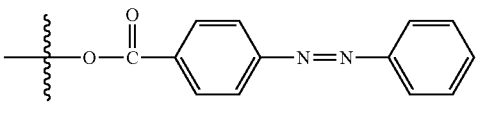 | 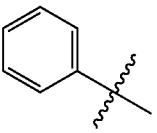 [SMILES: *c1ccccc1] | CH₃ |
| O/NH/O/O/OH | 2 | 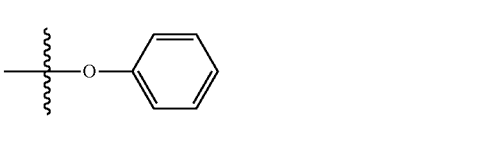 [SMILES: *Oc1ccccc1] | 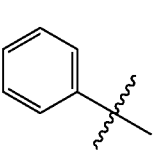 [SMILES: *c1ccccc1] | CH₃ |
| O/NH/O/O/OH | 2 |  |  | CH₃ |
| O/NH/O/O/OH | 2 | 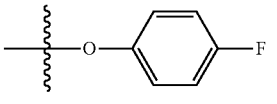 | 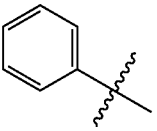 [SMILES: *c1ccccc1] | CH₃ |

TABLE 1-continued
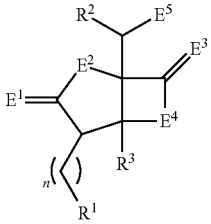
| E¹/E²/E³/E⁴/E⁵ | n | R¹ | R² | R³ |
|---|---|---|---|---|
| O/NH/O/O/OH | 2 | 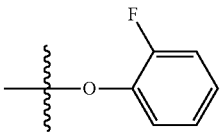 [SMILES: *Oc1ccccc1F] | 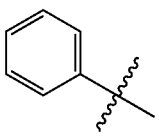 [SMILES: *c1ccccc1] | $CH_3$ |
| O/NH/O/O/OH | 2 | 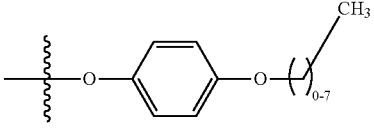 | 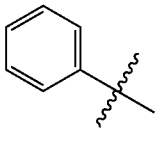 [SMILES: *c1ccccc1] | $CH_3$ |
| O/NH/O/O/OH | 2 | 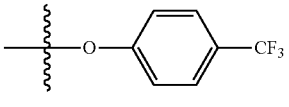 | 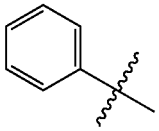 [SMILES: *c1ccccc1] | $CH_3$ |
| O/NH/O/O/OH | 2 | 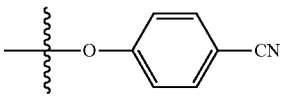 [SMILES: *Oc1ccc(C#N)cc1] | 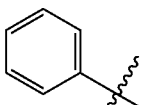 | $CH_3$ |
| O/NH/O/O/OH | 2 | 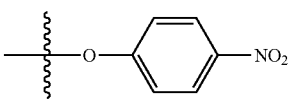 | 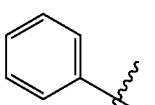 | $CH_3$ |
| O/NH/O/O/OH | 2 | 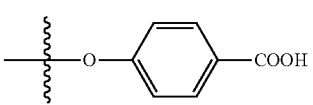 | 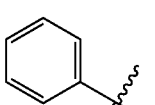 | $CH_3$ |
| O/NH/O/O/OH | 2 | 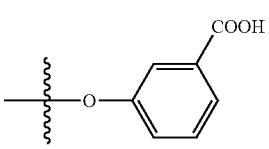 [SMILES: *Oc1cccc(C(=O)O)c1] | 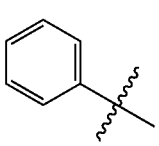 [SMILES: *c1ccccc1] | $CH_3$ |
| O/NH/O/O/OH | 2 | 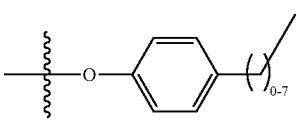 | 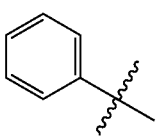 | $CH_3$ |

TABLE 1-continued

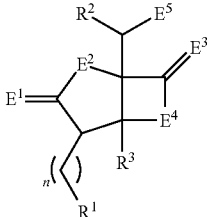

| $E^1/E^2/E^3/E^4/E^5$ | n | $R^1$ | $R^2$ | $R^3$ |
|---|---|---|---|---|
| O/NH/O/O/OH | 2 | 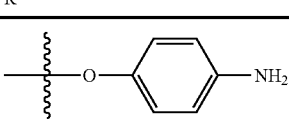 | 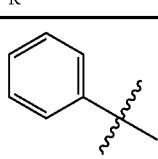 | $CH_3$ |
| O/NH/O/O/OH | 2 | 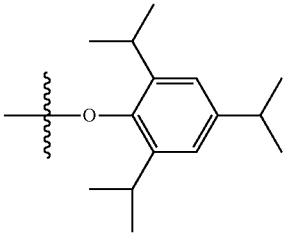 [SMILES: *Oc1c(C(C)C)cc(C(C)C)cc1C(C)C] | 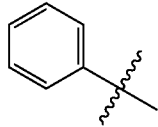 [SMILES: *c1ccccc1] | $CH_3$ |
| O/NH/O/O/OH | 2 | 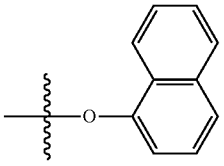 [SMILES: *Oc1cccc2ccccc12] | 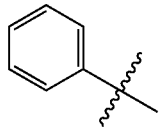 [SMILES: *c1ccccc1] | $CH_3$ |
| O/NH/O/O/OH | 2 | 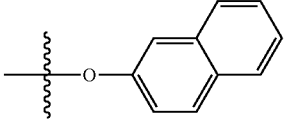 [SMILES: *Oc1ccc2ccccc2c1] | 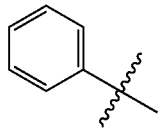 [SMILES: *c1ccccc1] | $CH_3$ |
| O/NH/O/O/OH | 2 | 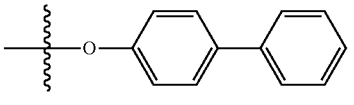 | 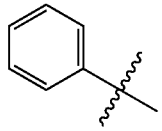 [SMILES: *c1ccccc1] | $CH_3$ |
| O/NH/O/O/OH | 2 | 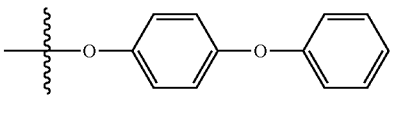 | 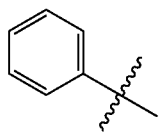 [SMILES: *c1ccccc1] | $CH_3$ |
| O/NH/O/O/OH | 2 | 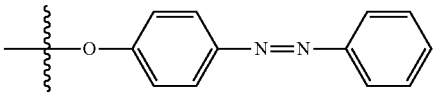 | 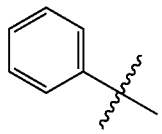 | $CH_3$ |

Synthesis

Compounds of Formula (I), and those described herein may be prepared in various ways. General synthetic routes to the compounds of Formula (I), and examples of starting materials that can be used to synthesize the compounds of Formula (I) are shown in Schemes 2, 3 and 4. The routes shown are illustrative only and are not intended, nor are they to be construed, to limit the scope of the claims in any manner whatsoever. Those skilled in the art will be able to recognize modifications of the disclosed synthesis and to devise alternate routes based on the disclosures herein; all such modifications and alternate routes are within the scope of the claims.

Scheme 2

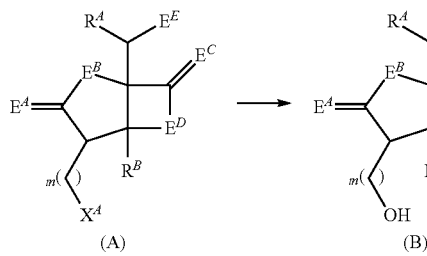

(A)        (B)

Scheme 3

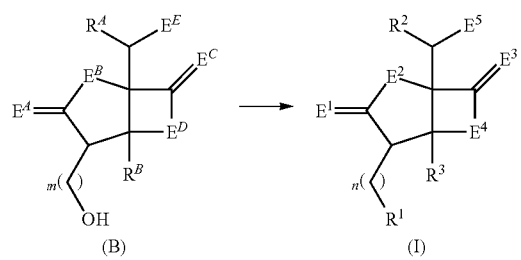

(B)        (I)

The halogen of a compound of Formula (A), denoted by $X^A$, can be replaced with a hydroxy group to form a compound of Formula (B) using one or more synthetic routes, such as the routes disclosed in U.S. Pat. No. 7,276,430; U.S. Publication Nos. 2005-0049294, 2007-0249693, 2005-0228186 and 2006-0287520; and PCT Publication Nos. WO 2006/060809, WO 2007/117591 and WO 2005/099687. A compound of Formula (A) can be obtained made using methods described in U.S. Pat. No. 7,276,430; U.S. Publication Nos. 2005-0049294, 2007-0249693, 2005-0228186 and 2006-0287520; and PCT Publication Nos. WO 2006/060809, WO 2007/117591 and WO 2005/099687. Alternatively, a compound of Formula (B) can be synthesized by treating a compound of Formula (A) with a silver reagent to form a compound of Formula (B). In an embodiment, $X^A$ can be iodo. Suitable silver reagents that can be used include, but are not limited to, silver fluoride (Ag—F) and AgF—$CaF_2$. Treatment of a compound of Formula (A) with a silver reagent provides a method for obtaining a compound of Formula (B) with good yields.

In some embodiments, for compounds of Formulae (A) and (B), $R^A$ can be selected from: a hydrogen, a halogen, cyano, a mono-substituted, a poly-substituted or an unsubstituted variant of the following residues: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, acyl, acylalkyl, alkyloxycarbonyloxy, carbonylacyl, aminocarbonyl, azido, azidoalkyl, mono-haloalkyl, di-haloakyl, tri-haloalkyl, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl)alkyl, pyridinylalkyl, a salt of a pyridinylalkyl, a salt of a heteroarylalkyl guanidino, a salt of a guanidino, and guanidinoalkyl; $R^B$ can be selected from hydrogen, halogen, a mono-substituted, a poly-substituted or an unsubstituted variant of the following residues: $C_{1-6}$ alkyl, $C_{3-6}$ cycloalkyl, $C_{2-6}$ alkenyl, $C_{3-6}$ cycloalkenyl, aryl, and arylalkyl; m can be 1, 2 or 3; $E^A$, $E^C$, $E^D$ and $E^E$ can be each independently a substituted or unsubstituted heteroatom; $E^B$ can be a substituted or unsubstituted heteroatom (such as NH) or —$CH_2$— group; and $X^A$ can be halogen. In some embodiments, $E^E$ can be $NH_2$, OH or SH. In an embodiment, $E^E$ can be OH.

A compound of Formula (B) can then be reacted with a compound that contains a sulfonyl moiety, for example,

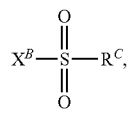

to form a compound of Formula (I), wherein $R^1$ is

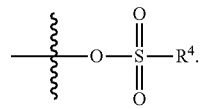

Similarly, a compound of Formula (B) can be reacted with a compound that contains a carboxylic acid or acid chloride moiety, such as

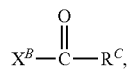

to form a compound of Formula (I), wherein $R^1$ is

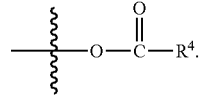

For compounds having the structure:

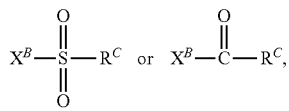

$R^C$ can be selected from a mono-substituted, a poly-substituted or an unsubstituted variant of the following residues: aryl, aryl($C_{1-6}$ alkyl), heteroaryl, heteroaryl($C_{1-6}$ alkyl), heterocyclyl, and heterocyclyl($C_{1-6}$ alkyl), wherein $R^C$ can be optionally substituted with can be optionally substituted with

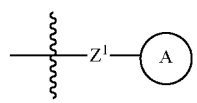

wherein A can be selected from a mono-substituted, a poly-substituted or an unsubstituted variant of the following residues: heterocyclyl, aryl and heteroaryl; and $Z^1$ can be selected from O (oxygen), S (sulfur), N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—$C(=O)N(R^{17})$, CH=CH—C(=O), $O(CH_2)_{1-6}O$, $O(CH_2)_{1-6}$ and $N(R^{17a})C(=O)N(R^{17b})$, wherein $R^{17}$, $R^{17a}$ and $R^{17b}$ can be independently selected from: H, $C_{1-4}$ alkyl, a substituted or unsubstituted benzyl, an allyl, and t-butoxycarbonyl (t-BOC); and $X^B$ can be a leaving group or hydroxy. In an embodiment, $X^B$ can be a halogen. In some embodiments, a base can be used to facilitate the reaction. Suitable bases are known to those skilled in the art, and include, but are not limited to, amine-based bases, such as diethylamide and pyridine, or pyridine based bases, such as 4-(dimethylamino)pyridine (DMAP). In some embodiments, a dehydrating agent such as N,N'-dicyclohexylcarbodiimide (DCC) or 1-ethyl-3-(3-dimethylaminopropyl) carbodiimide (EDC) can be used along with one or more of the aforementioned bases to facilitate the formation of the carboxylic esters from carboxylic acids.

Scheme 4

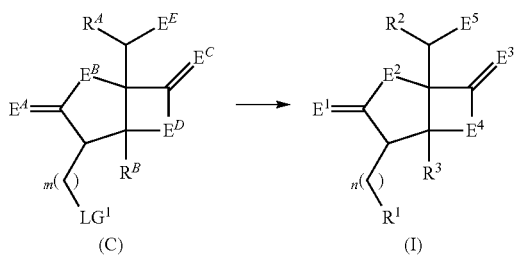

A compound of Formula (I) with $R^1$ having the structure

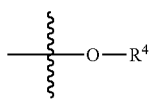

can be obtained starting with a compound of Formula (C) that has a leaving group, such as a sulfonate ester or halogen, at the equivalent position of $R^1$ for a compound of Formula (I). As shown in Scheme 4, a compound of Formula (C) can be reacted with a base and a compound having the structure $X^B$—$R^C$, wherein $R^C$ can be selected from a mono-substituted, a poly-substituted or an unsubstituted variant of the following residues: aryl, aryl($C_{1-6}$ alkyl), heteroaryl, heteroaryl($C_{1-6}$ alkyl), heterocyclyl, and heterocyclyl($C_{1-6}$ alkyl), wherein $R^C$ can be optionally substituted with

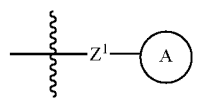

wherein A can be selected from a mono-substituted, a poly-substituted or an unsubstituted variant of the following residues: heterocyclyl, aryl and heteroaryl; and $Z^1$ can be selected from O (oxygen), S (sulfur), N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—$C(=O)N(R^{17})$, CH=CH—C(=O), $O(CH_2)_{1-6}O$, $O(CH_2)_{1-6}$ and $N(R^{17a})C(=O)N(R^{17b})$, wherein $R^{17}$, $R^{17a}$ and $R^{17b}$ can be independently selected from: H, $C_{1-4}$ alkyl, a substituted or unsubstituted benzyl, an allyl, and t-butoxycarbonyl (t-BOC); and $X^B$ can be a leaving group or hydroxy, to form a compound of Formula (I) that has a

moiety at $R^1$. Examples of suitable bases include, but are not limited to, sodium hydride, potassium hydride, lithium hydride, potassium tert-butoxide lithium diisopropylamide (LDA), butyl lithium and calcium hydride. In some embodiments, a compound of Formula (I) where $R^1$ is

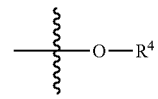

can be obtained starting with a compound of Formula (A), synthesizing a compound of Formula (B) as described herein, obtaining a compound of Formula (I) where $R^1$ is

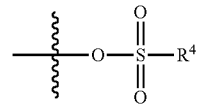

using one of the procedures described herein, and then reacting the compound of Formula (I) where $R^1$ is

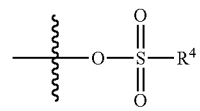

with a compound having the structure $X^B$—$R^C$ wherein $R^C$ can be selected from a mono-substituted, a poly-substituted or an unsubstituted variant of the following residues: aryl, aryl($C_{1-6}$ alkyl), heteroaryl, heteroaryl($C_{1-6}$ alkyl), heterocyclyl, and heterocyclyl($C_{1-6}$ alkyl), wherein $R^C$ can be optionally substituted with

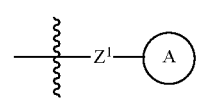

wherein A can be selected from a mono-substituted, a poly-substituted or an unsubstituted variant of the following residues: heterocyclyl, aryl and heteroaryl; and $Z^1$ can be selected from O (oxygen), S (sulfur), N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)(CH_2)_{1-6}$, $N(R^{17})C(=O)O(CH_2)_{1-6}$, $S(O)_2$, $C(=O)$, $(CH_2)_{1-6}C(=O)$, $O(CH_2)_{1-6}C(=O)$, $(CH_2)_{1-6}N(R^{17})C(=O)$, CH=CH—C(=O)N(R^{17})$, CH=CH—C(=O), $O(CH_2)_{1-6}O$, $O(CH_2)_{1-6}$ and $N(R^{17a})C(=O)N(R^{17b})$, wherein $R^{17}$, $R^{17a}$ and $R^{17b}$ can be independently selected from: H, $C_{1-4}$ alkyl, a substituted or unsubstituted benzyl, an allyl, and t-butoxycarbonyl (t-BOC); and $X^B$ can be a leaving group or hydroxy. A compound of Formula (I), where $R^1$ is

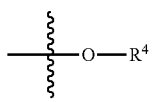

can also be obtained by reacting a compound of Formula (A) with $X^B$—$R^C$.

Pharmaceutical Compositions

An embodiment described herein relates to a pharmaceutical composition, that can include a therapeutically effective amount of one or more compounds described herein (e.g., a compound of Formula (I)), and a pharmaceutically acceptable carrier, diluent, excipient or combination thereof.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, intramuscular, intraocular, intranasal, intravenous, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutical compositions will generally be tailored to the specific intended route of administration.

The term "physiologically acceptable" defines a carrier, diluent or excipient that does not abrogate the biological activity and properties of the compound.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Suitable routes of administration may, for example, include oral, rectal, topical transmucosal, or intestinal administration; parenteral delivery, including intramuscular, subcutaneous, intravenous, intramedullary injections, as well as intrathecal, direct intraventricular, intraperitoneal, intranasal, intraocular injections or as an aerosol inhalant.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes will be targeted to and taken up selectively by the organ.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that include a compound disclosed herein formulated in a compatible pharmaceutical carrier may also be prepared, placed in an appropriate container, and labeled for treatment of an indicated condition.

Methods of Use

One embodiment disclosed herein relates to a method of treating and/or ameliorating a disease or condition that can include administering to a subject a therapeutically effective amount of one or more compounds described herein, such as a compound of Formula (I), or a pharmaceutical composition that includes a compound described herein (for example, a compound of Formula (I)).

Some embodiments disclosed herein relate to a method of ameliorating or treating a neoplastic disease that can include administering to a subject suffering from the neoplastic disease a therapeutically effective amount of one or more compounds described herein (e.g., a compound of Formula (I)), a pharmaceutically acceptable salt, prodrug and/or a pro-drug ester thereof, or a pharmaceutical composition that includes one or more compounds described herein. In an embodiment, the neoplastic disease can be cancer. Examples of some types of cancer that can be treated and/or ameliorated with a therapeutically effective amount of one or more compounds described herein, such as a compound of Formula (I) include, but are not limited to, breast cancer, sarcoma, leukemia, ovarian cancer, bladder cancer, prostate cancer, colon cancer, rectal cancer, stomach cancer, lung cancer, lymphoma (such as Hodgkin's lymphoma, non-Hodgkin's lymphoma), multiple myeloma, pancreatic cancer, kidney cancer, endocrine cancer, melanoma, skin cancer, angio sarcoma, sinus cancer, esophageal cancer, uretal cancer, liver cancer, angioma, central nervous system (CNS) cancer (including brain cancer), Mantle cell lymphoma, low IgM secreting lymphoma, Burkitt's lymphoma, B-NHL and Waldenstrom's Macroglobulinemia. In some embodiments, the cancer can be selected from multiple myeloma, a colorectal carcinoma, a prostate carcinoma, a breast adenocarcinoma, a non-small cell lung carcinoma, an ovarian carcinoma, and a melanoma. In an embodiment, the cancer can be multiple myeloma.

The cancer also can be a drug-resistant cancer. In some instances, the drug-resistant cancer may display at least one of the following: elevated levels of the P-glycoprotein efflux pump, increased expression of the multidrug-resistance associated protein 1 encoded by MRP1, reduced drug uptake, alteration of the drug's target or increasing repair of drug-induced DNA damage, alteration of the apoptotic pathway or the activation of cytochrome P450 enzymes. In an embodiment, the drug resistant cancer can be a sarcoma and/or leukemia.

Still further embodiments relate to methods of inhibiting the growth of a cancer cell. The methods can include, for example, contacting a cancer cell with a compound a pharmaceutically acceptable salt, prodrug and/or a pro-drug ester thereof, or a pharmaceutical composition described herein. A non-limiting list of cancer cells include a breast cancer cell, a sarcoma cell, a leukemia cell, an ovarian cancer cell, a bladder cancer cell, a prostate cancer cell, a colon cancer cell, a rectal cancer cell, a stomach cancer cell, a lung cancer cell, a lymphoma cell, a multiple myeloma cell, a pancreatic cancer cell, a kidney cancer cell, an endocrine cancer cell, a melanoma cell, a skin cancer cell, an angiosarcoma cell, a sinus cancer cell, an esophageal cancer cell, an uretal cancer cell, a liver cancer cell, an angioma cell, a central nervous system (CNS) cancer cell (including a brain cancer cell). In an embodiment, the cancer cell may be, for example, a multiple myeloma cell, a colorectal carcinoma cell, a prostate carcinoma cell, a breast adenocarcinoma cell, a non-small cell lung carcinoma cell, an ovarian carcinoma cell, a melanoma cell, and the like.

Other embodiments relate to methods of inhibiting proteasome activity comprising the step contacting a cell with one or more compounds described herein (e.g., a compound of Formula (I)), a pharmaceutically acceptable salt, prodrug and/or a pro-drug ester thereof, or a pharmaceutical composition that includes one or more compounds described herein.

Further embodiments relate to methods of inhibiting NF-κB activation. The methods can include, for example, the step contacting a cell with one or more compounds described herein (e.g., a compound of Formula (I)), a pharmaceutically acceptable salt, prodrug and/or a pro-drug ester thereof, or a pharmaceutical composition that includes one or more compounds described herein.

Still other embodiments relate to methods for treating an inflammatory condition. The methods may include, for example, administering an effective amount of one or more compounds described herein (e.g., a compound of Formula (I)), a pharmaceutically acceptable salt, prodrug and/or a pro-drug ester thereof, or a pharmaceutical composition that includes one or more compounds described herein to a subject suffering from an inflammatory condition. An "inflammatory condition" includes, for example, conditions such as ischemia, septic shock, autoimmune diseases, rheumatoid arthritis, inflammatory bowel disease, systemic lupus eythematosus, multiple sclerosis, asthma, osteoarthritis, osteoporosis, fibrotic diseases, dermatosis, including psoriasis, atopic dermatitis and ultraviolet radiation (UV)-induced skin damage, psoriatic arthritis, alkylosing spondylitis, tissue and organ rejection, Alzheimer's disease, stroke, atherosclerosis, restenosis, diabetes, glomerulonephritis, cancer, Hodgkins disease, cachexia, inflammation associated with infection and certain viral infections, including acquired immune deficiency syndrome (AIDS), adult respiratory distress syndrome and Ataxia Telangiestasia. In some embodiments, the inflammatory condition can be selected from rheumatoid arthritis, asthma, multiple sclerosis, psoriasis, stroke, myocardial infarction, and the like.

Some embodiments relate to methods for treating a microbial illness which can include administering an effective amount of one or more compounds described herein (e.g., a compound of Formula (I)), a pharmaceutically acceptable salt, prodrug and/or a pro-drug ester thereof, or a pharmaceutical composition that includes one or more compounds described herein to a subject suffering from a microbial illness. The microbial illness maybe caused, for example by *B. anthracis, Plasmodium, Leishmania, Trypanosoma, Mycobacterium bovis, Mycobacterium africanum* and *Mycobacterium microti*. Examples of microbial illness include, but are not limited to the following: Bacteremia, Botulism, Brucellosis, *Clostridium Difficile, Campylobacter* Infection, Cat Scratch Disease, Chancroid, *Chlamydia, Cholera, Clostridium Perfringens*, Bacterial Conjunctivitis, Diphtheria, *E. Coli* Infections, Ehrlichiosis, Epididymitis, *Gardnerella*, Gas Gangrene, Gonorrhea, *Helicobacter Pylori*, Haemophilus, Influenzae B, Impetigo, Intertrigo, Leprosy, Listeriosis, Lyme Disease, Methicillin Resistant *Staphylococcus Aureus*, Orchitis, Osteomyelitis, Otitis, Media Pertussis, Plague, Pneumonia, Prostatitis Pyelonephritis, Q Fever, Rocky Mountain Spotted Fever, Salmonellosis, Scarlet Fever, Sepsis, Shigellosis, Staphylococcal Infections, Streptococcal Infections, Syphilis, Tetanus, Toxic Shock Syndrome, Trachoma, Traveller's Diarrhea, Tuberculosis, Tularemia, Typhoid Fever, Typhus Fever, Urinary Tract Infections, Bacterial Vaginosis, Pertussis, Yersiniosis, malaria, African trypanosomiasis, candidiasis, histoplasmosis, blastomycosis, coccidioidomycosis, aspergillisis, and mucormycosis.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance.

The term "therapeutically effective amount" is used to indicate an amount of an active compound, or pharmaceutical agent, that elicits the biological or medicinal response indicated. For example, a therapeutically effective amount of compound can be the amount need to prevent, alleviate or ameliorate symptoms of disease or prolong the survival of the subject being treated This response may occur in a tissue, system, animal or human and includes alleviation of the symptoms of the disease being treated. Determination of a therapeutically effective amount is well within the capability of those skilled in the art, especially in light of the detailed disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. (See e.g., Fingl et al. 1975, in "The Pharmacological Basis of Therapeutics", which is hereby incorporated herein by reference in its entirety, with particular reference to Ch. 1, p. 1). The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

Although the exact dosage will be determined on a drug-by-drug basis, in most cases, some generalizations regarding the dosage can be made. The daily dosage regimen for an adult human patient may be, for example, an oral dose of between 0.01 mg and 3000 mg of each active ingredient, preferably between 1 mg and 700 mg, e.g. 5 to 200 mg. The dosage may be a single one or a series of two or more given in the course of one or more days, as is needed by the patient. In some embodiments, the compounds will be administered for a period of continuous therapy, for example for a week or more, or for months or years.

In instances where human dosages for compounds have been established for at least some condition, those same dosages, or dosages that are between about 0.1% and 500%, more preferably between about 25% and 250% of the established human dosage will be used. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Alternatively dosages may be based and calculated upon the surface area of the patient, as understood by those of skill in the art.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

EXAMPLES

Embodiments are disclosed in further detail in the following examples, which are not in any way intended to limit the scope of the claims.

General Experimental Procedures.

NMR spectra were collected using a 500 MHz Bruker Avance spectrometer using an inverse probe equipped with x, y, z-gradients, except for the $^{13}C$ NMR spectra, which were acquired with a broad-band observe probe. Data were acquired at 298K in $CDCl_3$ referencing 7.24 ppm and 77.00 ppm or DMSO-d6 referencing 2.49 ppm and 39.00 ppm for $^1$H and $^{13}$C-NMR respectively. The LC-MS data were obtained from an Agilent HP1100 HPLC equipped with an Agilent PDA detector (the mobile phase was a mixture of CH$_3$CN and H$_2$O) and MSD system. Semi-preparative HPLC was performed on a Gilson HPLC equipped with a Gilson 215 fraction collector, Agilent PDA detector and/or ELSD (Sedere) detector. HPLC solvents were obtained from Fisher Scientific and VWR. Deuterated solvents were obtained from Cambridge Isotope Laboratories, Inc. All other chemical reagents were obtained from Sigma-Aldrich, Example 1

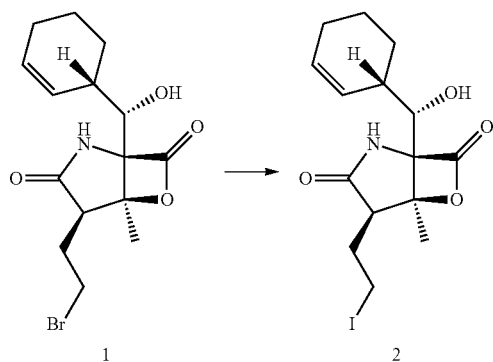

Sodium iodide (325 mg, 2.2 mmol) was added to a solution of 1 (78 mg, 0.22 mmol) in acetone and stirred at room temperature for 48 hours. The solution was then concentrated under a stream of nitrogen and this concentrated solution was run on a silica plug, in order to remove excess salts. A composition of 25% EtOAc/hexanes (25 mL) followed by 50% EtOAc/hexanes (200 mL) was used to elute 2 (74.9 mg, 84%).

Example 2

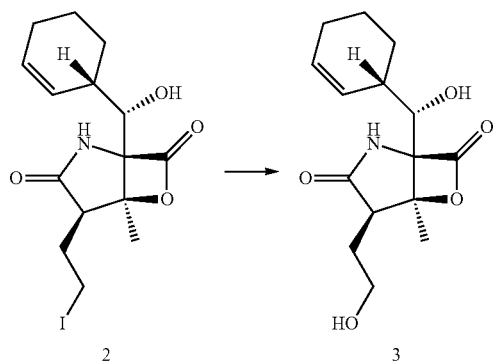

To a solution of compound 2 (40 mg, 0.099 mmol) in dry THF (4 mL) in the 20 mL amber vial was added AgF (18.8 mg, 0.15 mmol). The reaction mixture was stirred at room temperature for 16 hours, then filtered through a 0.45 micron syringe filter and concentrated. The reaction mixture was purified on reversed phase HPLC using an ACE 5μ C18 HPLC column of dimensions 22 mm id by 150 mm length at a flow rate of 14.5 mL/min. Solvent A consisted of water with 0.05% TFA and solvent B consisted of acetonitrile with 0.05% TFA and were used as follows: An initial gradient of 95% solvent A/5% solvent B increased linearly to 60% solvent A/40% solvent B over 18 minutes; this composition was then held for 8 minutes followed by a one minute ramp to 100% solvent B, which was held for 6 minutes before returning to the initial conditions. The purification was monitored by diode array detection (DAD), and 3 eluted at 16 min. Compound 3 was concentrated under reduced pressure (bath temperature<40° C.) after each injection in order to minimize hydrolysis. Compound 3 (11 mg, 15%) was obtained as a pure compound and confirmed by spectroscopic data that was identical to those of material synthesized by alternative methods, including those described herein.

Example 3

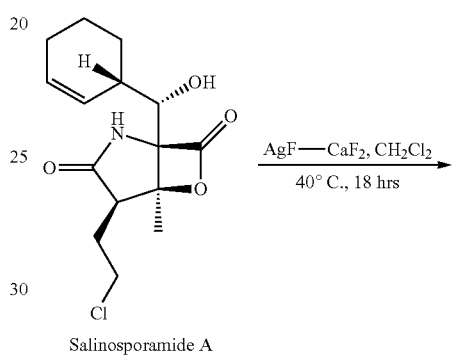

Salinosporamide A

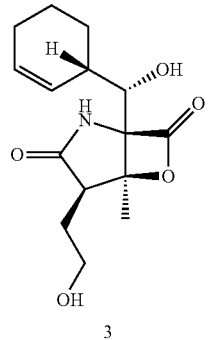

3

Preparation of AgF supported on CaF$_2$ (AgF—CaF$_2$): Silver fluoride was supported on calcium fluoride by slowly evaporating a mixture of silver carbonate (3.75 g) dissolved in water (5 mL), 48% aqueous HF (1.2 g, 1.2 mL) and calcium fluoride (15 g) to dryness in a 45 mL plastic vial at 50° C. in the dark for 2 hours. The reagent was further dried on freeze dryer for 15 hours to remove any traces of water. The final reagent was a brown free-flow granular powder, highly hygroscopic and light sensitive.

1 g of AgF—CaF$_2$ was activated by heating at 40° C. under vacuum in a round bottom flask with a magnetic stir bar for 30 minutes, to which a solution of Salinosporamide A (250 mg, 0.8 mmol dissolved in 25 mL of dry CH$_2$Cl$_2$) was added and stirred at the same temperature for 18 hours. The solvent was removed under reduce pressure and the resulting residue was purified by silica flash using a solvent gradient of 50% EtOAc/hexanes, 75% EtOAc/Hexane, 100% EtOAc, 20% methanol/EtOAc and 40% methanol/EtOAc. Compound 3 was eluted in 20-40% methanol/EtOAc fractions as a pure compound (83 mg, 35% yield). ESIMS, m/z 296 [M+H]+.

Example 4

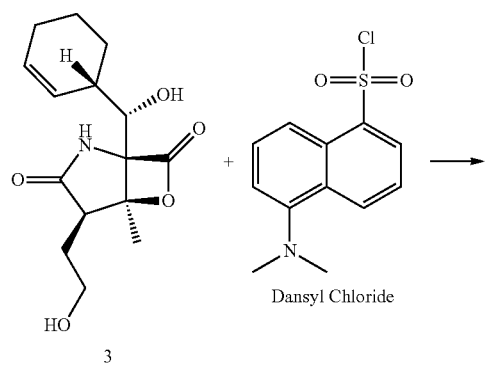

Dansyl Chloride

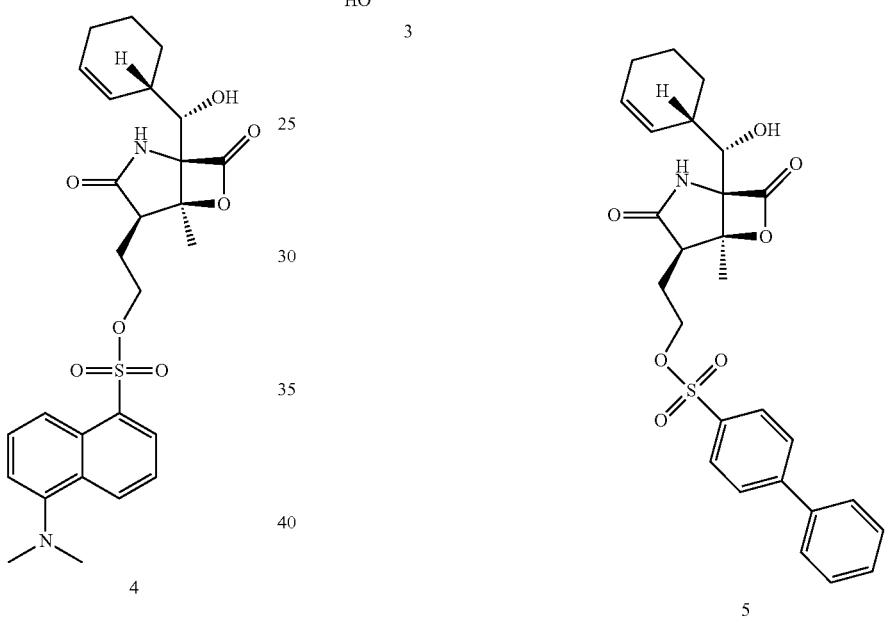

To a solution of compound 3 (17 mg, 0.058 mmol) in dry CH$_2$Cl$_2$ (5 mL) was added Et$_3$N (36 μL, 0.26 mmol) and dansyl chloride (78.5 mg, 0.29 mmol) and the solution was stirred at room temperature for 24 hours. Additional dansyl chloride (78.5 mg, 0.29 mmol) and Et$_3$N (36 μL, 0.26 mmol) were added and the reaction was stirred at room temperature overnight. At 42 hours, the reaction was concentrated under reduced pressure, redissolved in 5 mL of ACN and purified on reversed phase HPLC using an ACE 5μ C18 column (22 mm×150 mm) at a flow rate of 14.5 mL/min. A solvent gradient of 100% water to 35% acetonitrile/65% water over 8 minutes, holding at this solvent composition for 2 minutes and then linear gradient increasing to 100% acetonitrile over 5 min, which was then held at 100% acetonitrile for 6 min before returning to 100% water was used to purify 4. The purification was monitored by diode array detection (DAD) and 4 eluted as a pure compound at 15 minutes (17 mg, 0.032 mmol, 55.3%). HRESIMS m/z 529.1993 [M+H]+ (calcd for C$_{27}$H$_{33}$N$_2$O$_7$S, 529.2008), $^1$H NMR (DMSO-d$_6$); δ 1.18 (br m, 1H), 1.38 (br m, 1H), 1.46 (s, 3H), 1.74 (br m, 4H), 1.90 (m, 2H), 2.19 (m, 1H), 2.42 (t, J=7.3 Hz 1H), 2.84 (s, 6H, dansyl), 3.60 (t, J=9.5 Hz, 1H), 4.29 (m, 2H), 5.47 (d, J=7.9 Hz, C-5 (OH)), 5.73 (m, 2H), 7.29 (d, J=7.6 Hz, 1H, dansyl), 7.67 (m, 2H, dansyl), 8.11 (d, J=8.8 Hz, 1H, dansyl), 8.26 (dd, J=1.3, 7.3 Hz, 1H, dansyl), 8.59 (d, J=8.8 Hz, 1H, dansyl), 8.99 (s, NH).

Example 5

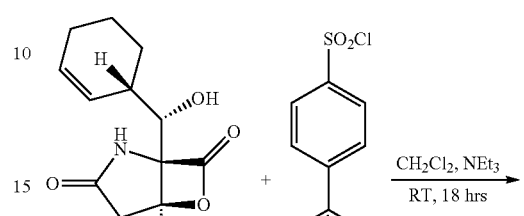

To a solution of compound 3 (10 mg, 0.034 mmol) in dry CH$_2$Cl$_2$ (3.5 mL) was added Et$_3$N (48 μL, 0.34 mmol) and biphenyl-4-sulfonyl chloride (80 mg, 0.32 mmol) and the solution was stirred at room temperature for 18 hours. The reaction was concentrated under reduced pressure, redissolved in 2 mL of ACN and purified by reversed phase HPLC using an ACE 5μ C18 column (22 mm id×150 mm length) at a flow rate of 14.5 mL/min using the following solvent gradient: 10% ACN/water to 90% ACN/water over 18 minutes, then increasing to 100% ACN over 1 minute, and holding at this solvent composition for 5 minutes. The purification was monitored by diode array detection (DAD). The product, compound 5, eluted at 13.5 minutes and was concentrated under reduced pressure to yield 7 mg of product (80% pure). The product was further purified using a slightly modified gradient, i.e. 10% ACN/water to 80% ACN/water over 11 minutes, holding at this solvent composition for 3 min, then increasing to 100% ACN over 1 minute, and holding at this solvent composition for 5 minutes. Compound 5 eluted at 13.5 minutes and was concentrated under reduced pressure to yield pure compound 5 (4.5 mg, 26%). $^1$H NMR (CDCl$_3$, 500 MHz); δ 1.51-1.60 (ca, 2H), 1.74 (s, 3H), 1.74-1.87 (ca, 2H), 1.98-2.15 (ca, 4H), 2.44 (m, 1H), 2.64 (t, J=7.0 Hz 1H), 3.85 (t, J=7.4 Hz, 1H), 4.31 (m, 1H), 4.46 (m, 1H), 5.66 (br d, J=10.4 Hz, 1H), 5.98 (m, 1H), 6.84 (s, 1H, NH), 7.42 (t, J=7.4 Hz, 1H, biphenyl), 7.47 (t, J=7.4 Hz, 2H, biphenyl), 7.59 (d, J=7.4 Hz, 2H, biphenyl), 7.75 (d, J=8.0 Hz, 2H, biphenyl), 7.96 (d, J=8.0 Hz, 2H, biphenyl); $^{13}$C NMR (CDCl$_3$, 125 MH$_z$); δ 176.5, 167.1, 147.0, 139.0, 134.3, 133.3, 129.1 (2×CH), 128.8, 128.4 (2×CH), 128.0 (2×CH), 127.4 (2×CH), 124.1, 85.5, 78.5, 70.3, 67.7, 44.0, 38.0, 26.8, 24.9, 24.6, 20.7, 19.5); ESIMS m/z 512 [M+H]$^+$.

Example 6

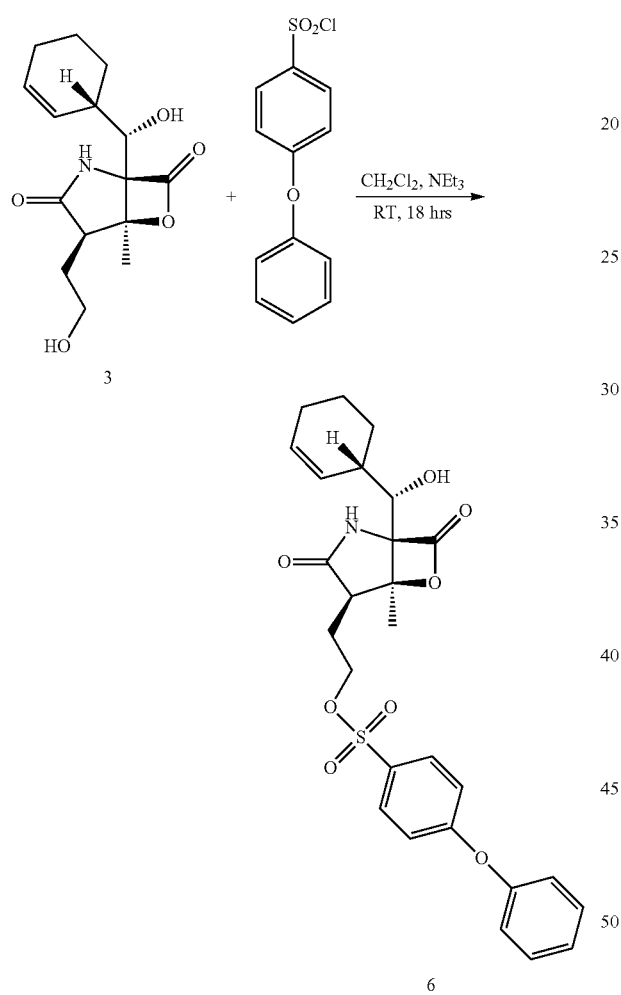

To a solution of compound 3 (12 mg, 0.041 mmol) in dry CH$_2$Cl$_2$ (3.5 mL) was added Et$_3$N (58 µL, 0.41 mmol) and biphenyl-4-sulfonyl chloride (110 mg, 0.30 mmol), and the solution was stirred at room temperature for 18 hours. The reaction was concentrated under reduced pressure, redissolved in 2 mL of ACN and purified by reversed phase HPLC using an ACE 5µ C18 column (22 mm×150 mm) at a flow rate of 14.5 mL/min using the following solvent gradient: 10% ACN/water to 90% ACN/water over 18 minutes, then increasing to 100% ACN over 1 minute, and holding at this solvent composition for 5 minutes. The purification was monitored by diode array detection (DAD). The product, compound 6, eluted at 13.0 minutes and was concentrated under reduced pressure to yield 88% pure compound. The product was further purified using slightly modified gradient, i.e. 10% ACN/water to 80% ACN/water over 11 minutes, holding at this solvent composition for 3 min, then increasing to 100% ACN over a minute, and holding at this solvent composition for 5 minutes. Compound 6 eluted at 13.25 minutes and was concentrated under reduced pressure to yield pure compound 6 (2.6 mg, 12%). $^1$H NMR (CDCl$_3$, 500 MH$_z$); δ 1.51-1.60 (m, 2H), 1.75 (s, 3H), 1.74-1.87 (m, 2H), 1.98-2.15 (m, 4H), 2.47 (m, 1H), 2.63 (t, J=7.2 Hz, 1H), 3.88 (d, J=5.7 Hz, 1H), 4.27 (m, 1H), 4.40 (m, 1H), 5.65 (br dd, J=2.5, 10.0 Hz, 1H), 6.00 (m, 1H), 6.54 (s, 1H, NH), 7.03-7.09 (m, 4H, phenoxyphenyl), 7.22 (t, J=8 Hz, H, phenoxyphenyl), 7.41 (br t, J=8 Hz, 2H, phenoxyphenyl), 7.83 (br d, J=8.0 Hz, 4H, phenoxyphenyl); $^{13}$C NMR (CDCl$_3$, 125 MH$_z$); δ 176.2, 167.1, 162.7, 154.8, 133.6, 130.3 (2×CH), 130.2 (2×CH), 129.0, 125.3, 123.9, 120.5 (2×CH), 117.7 (2×CH), 85.6, 78.4, 70.2, 67.4, 44.0, 38.0, 26.9, 24.9, 24.6, 20.7, 19.5; ESIMS m/z 528 [M+H]$^+$.

Example 7

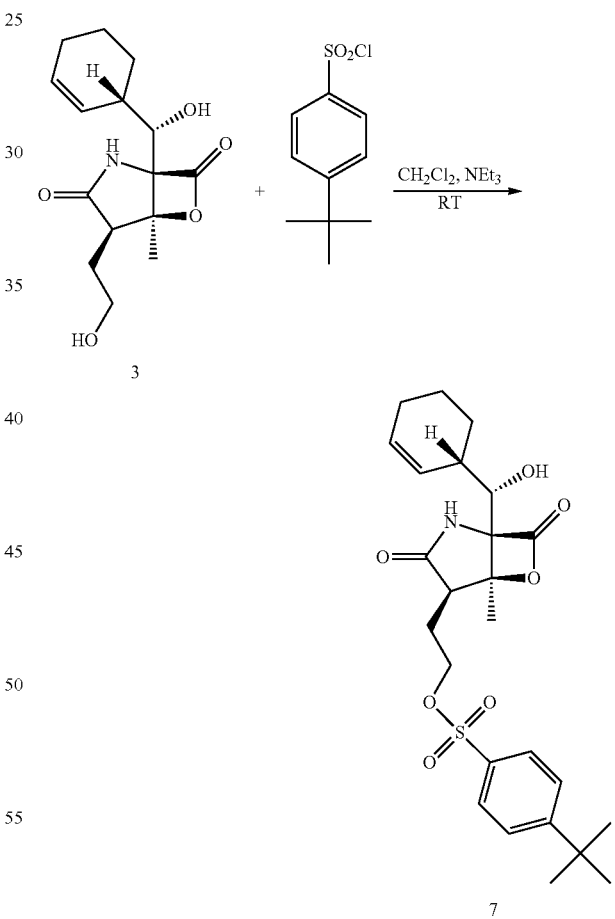

To a solution of compound 3 (20 mg, 0.068 mmol) in dry CH$_2$Cl$_2$ (4 mL) was added Et$_3$N (96 µL, 0.68 mmol) and 4-t-butylphenylsulfonyl chloride (158 mg, 0.68 mmol), and the reaction was stirred at room temperature for 4 hours. The reaction was concentrated under reduced pressure, redissolved in 3 mL of ACN and purified by reversed phase HPLC using an ACE 5µ C18 column (22 mm×150 mm) at a flow rate of 14.5 mL/min using the following solvent gradient: 10% ACN/water to 80% ACN/water over 11 minutes, holding at this solvent composition for 3 min, then increasing to 100% ACN over a minute, and holding at this solvent composition for 5 minutes. The purification was monitored by diode array detection (DAD). The product, compound 7, eluted at 13.5 minutes and was concentrated under reduced pressure to yield 90% pure compound (7.3 mg) which was further purified using normal phase silica plug column and 100% $CH_2Cl_2$ (3 mL), 30% EtOAc/hexanes (6 mL), 50% EtOAc/hexanes (6 mL) and 100% EtOAc (10 mL) gradient. The pure compound, compound 7, was eluted in 30% EtOAc/hexanes which was concentrated under reduced pressure to yield colorless solid of compound 7 (1.6 mg, 4.8%). $^1$H NMR (CDCl$_3$, 500 MH$_z$); δ 1.33 (s, 9H, t-Bu), 1.51-1.62 (m, 4H), 1.73 (s, 3H), 1.75-1.87 (m, 2H), 1.98-2.06 (m, 2H), 2.09 (m, 1H), 2.46 (m, 1H), 2.66 (t, J=7.2 Hz, 1H), 3.88 (d, J=5.7 Hz, 1H), 4.25 (m, 1H), 4.40 (m, 1H), 5.64 (br dd, J=2.5, 10.0 Hz, 1H), 6.01 (m, 1H), 6.44 (s, 1H, NH), 7.55 (br d, J=8.5 Hz, 2H), 7.82 (br d, J=8.5 Hz, 2H); $^{13}$C NMR (CDCl$_3$, 125 MH$_z$); δ 176.1, 167.1, 158.0, 133.8, 132.6, 127.8 (2×CH), 126.4 (2×CH), 123.7, 85.6, 78.2, 70.1, 67.4, 43.9, 37.9, 35.3, 31.0 (t-Bu), 26.9, 24.9, 24.6, 20.6, 19.5; ESIMS m/z 492 [M+H]$^+$.

Example 8 then added biphenyl-4-carbonyl chloride (30 mg, 0.14 mmol) in dry $CH_2Cl_2$ (1 mL). The reaction mixture was warmed to room temperature and stirred for 3 hours. The reaction mixture was concentrated under reduced pressure, redissolved in 2 mL of ACN and purified by reversed phase HPLC using an ACE 5μ C18 column (22 mm×150 mm) at a flow rate of 14.5 mL/min using the following solvent gradient: 10% ACN/water to 80% ACN/water over 11 minutes, holding at this solvent composition for 3 min, then increasing to 100% ACN over a minute, and holding at this solvent composition for 5 minutes. The product, compound 8, eluted at 14.0 minutes and was concentrated under reduced pressure to yield pure compound 8 (3.4 mg, 10.5%). $^1$H NMR (CDCl$_3$, 500 MH$_z$); δ 1.50-1.63 (m, 2H), 1.81 (s, 3H), 1.76-1.91 (m, 2H), 2.02 (br m, 2H), 2.18 (m, 1H, 12-Hb), 2.31 (m, 1H, 12-Ha) 2.51 (m, 1H, 6-H), 2.69 (t, J=7.2 Hz, 1H, 2-H), 3.91 (br d, J=4.4 Hz, 1H, 5-H), 4.59 (br t, J=6.4 Hz, 2H, 13-H$_2$), 5.68 (br dd, J=2.2, 10.0 Hz, 1H, 7-H), 6.01 (m, 1H, 8-H), 6.73 (s, 1H, NH), 7.38 (br t, J=7.2 Hz, 1H), 7.45 (t, J=7.2 Hz, 2H), 7.60 (br t, J=7.2 Hz, 2H), 7.65 (br d, J=8.2 Hz, 2H) and 8.08 (br d, J=8.2 Hz, 2H); $^{13}$C NMR (CDCl$_3$, 125 MH$_z$); δ 176.7, 167.3, 166.2, 145.9, 139.9, 133.6, 130.1 (2×CH), 128.9 (2×CH), 128.7, 128.2, 127.3 (2×CH), 127.1 (2×CH), 123.9, 85.7, 78.5, 70.3, 62.3, 45.3, 38.0, 26.9, 24.9, 24.4, 20.7, 19.9; ESIMS m/z 476 [M+H]$^+$.

Example 9

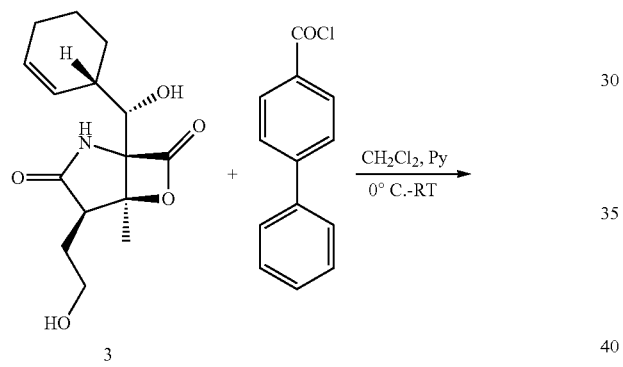

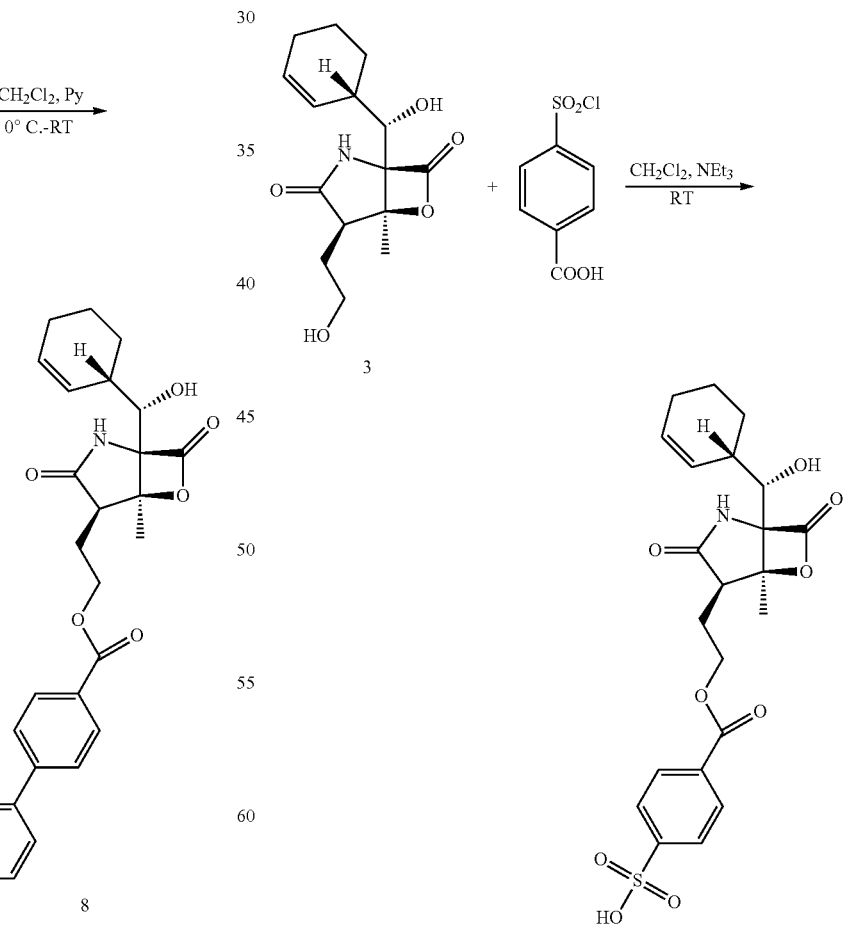

To a solution of compound 3 (20 mg, 0.068 mmol) in dry $CH_2Cl_2$ (3 mL) was added pyridine (200 μL, 0.41 mmol) and stirred for 5 min. The reaction mixture was cooled to 0° C. and To a solution of compound 3 (50 mg, 0.17 mmol) in dry CH$_2$Cl$_2$ (4 mL) was added Et$_3$N (118 μL, 0.85 mmol) and 4-(Chlorosulfonyl)benzoic acid (182 mg, 0.85 mmol) and stirred at room temperature for 16 hours under N$_2$ atmosphere. Added more Et$_3$N (118 μL, 0.85 mmol) and stirred for additional 4 hours. The reaction mixture was concentrated under reduced pressure, re-dissolved in ACN and DMSO (1:1; 2 mL) and purified on reversed phase HPLC using Ace 5μ C18 column (22 mm×150 mm) and solvent gradient of 5% Acetonitrile, 95% water to 100% Acetonitrile over 17 minutes, holding at 100% acetonitrile for 3 min, at a flow rate of 14.5 mL/min. 0.05% of TFA was added to both water and Acetonitrile mobile phase. The purification was monitored by diode array detector (DAD). The product, compound 9, was eluted as a pure compound 9 (12 mg, 0.025 mmol, 15%). $^1$H NMR (DMSO-d$_6$, 500 MH$_z$); 1.21 (m, 1H), 1.40 (m, 1H), 1.69 (m, 1H), 1.74 (s, 3H), 1.83 (m, 1H), 1.91 (brs, 2H), 2.05 (m, 3H), 2.28 (m, 1H), 2.70 (t, J=7.0 Hz, 1H), 3.67 (d, J=9.5 Hz, 1H), 4.49 (m, 2H), 5.71 (br dd, J=2.5, 10.5 Hz, 1H), 5.80 (br d, J=10.5 Hz, 1H), 7.71 (d, J=8.0 Hz, 2H, phenyl), 7.94 (d, J=8.0 Hz, 2H, phenyl), 9.09 (brs, 1H, NH); $^{13}$C NMR (DMSO-d$_6$, 125 MH$_z$); δ 175.5, 168.6, 165.3, 129.4, 128.9 (2×CH), 128.5, 127.7, 125.8 (2×CH), 125.8, 85.6, 78.9, 69.0, 62.6, 45.0, 37.7, 25.3, 24.6, 23.7, 21.0, 19.3; ESIMS m/z 480 [M+H]$^+$.

Example 10

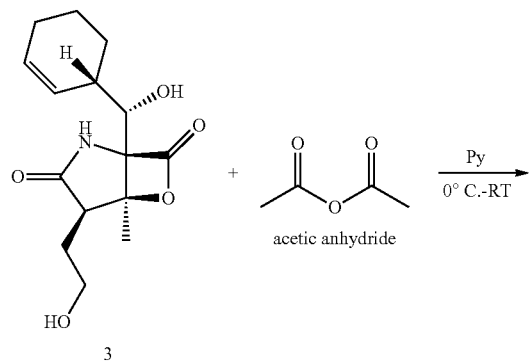

To a solution of compound 3 (12 mg, 0.041 mmol) in anhydrous pyridine (40 μL, 0.08 mmol) was added acetic anhydride (40 μL) and stirred the reaction mixture for 3 hours at room temperature. Then the reaction was quenched by adding some tiny ice cubes and extracted with EtOAc (3×3 mL). The combined organic layer was concentrated by a stream of nitrogen to yield a crude product of compound 10. The crude was re-dissolved in 2 mL ACN and purified by reversed phase HPLC using an ACE 5μ C18 column (22 mm×150 mm) at a flow rate of 14.5 mL/min using the following solvent gradient: 10% ACN/water to 90% ACN/water over 14 minutes, then increasing to 100% ACN over 1 minute, and holding at this solvent composition for 5 minutes. The purification was monitored by diode array detection (DAD). The product, compound 10, eluted at about 8.0 minutes and was concentrated under reduced pressure to yield about 80% pure product which was further purified using the same HPLC method. The pure fraction was concentrated by reduced pressure to yield a colorless solid of compound 10 (1.2 mg, 8.7%). $^1$H NMR (CDCl$_3$, 500 MH$_z$); δ 1.50-1.65 (m, 2H), 1.78 (s, 3H), 1.79-1.90 (m, 2H), 1.96-2.06 (br m, 3H), 2.05 (s, 3H), 2.14 (m, 1H), 2.50 (m, 1H, 6-H), 2.58 (t, J=7.0 Hz, 1H, 2-H), 3.90 (br d, J=5.7 Hz, 1H, 5-H), 4.32 (br t, J=6.4 Hz, 2H, 13-H$_2$), 5.66 (br dd, J=2.2, 10.0 Hz, 1H, 7-H), 6.02 (m, 1H, 8-H), 6.47 (s, 1H, NH); $^{13}$C NMR (CDCl$_3$, 125 MH$_z$); δ 176.5, 170.8, 167.3, 133.8, 123.8, 85.7, 78.3, 70.3, 61.7, 45.1, 37.9, 27.0, 24.9, 24.2, 20.9, 20.7, 19.8; ESIMS m/z 338 [M+H]$^+$.

Example 11

In Vitro Purified Rabbit Muscle 20S Proteasome Activity Assays

The chymotrypsin-like activity of the 20S proteasome was determined essentially as described in Macherla et al *J. Med. Chem.*, 2005, 48 (11), pp 3684-3687. Serial diluted test compounds were added in duplicate to 1 μg/ml purified rabbit 20S proteasome in assay buffer containing 20 mM HEPES, pH7.3, 0.5 mM EDTA, 0.05% Triton X-100 and 0.035% SDS and pre-incubated for 5 min at 37° C. Reactions were initiated by the addition of the Suc-LLVY-AMC peptide substrate at a final concentration of 20 μM. Fluorescence of the cleaved peptide substrate was measured at $\lambda_{ex}$=390 nm and $\lambda_{em}$=460 nm using a Fluoroskan Ascent 96-well microplate reader (Thermo Electron, Waltham, Mass.). The IC$_{50}$ values (the drug concentration at which 50% of the maximal relative fluorescence is inhibited) were calculated by Prism (GraphPad Software) using a sigmoidal dose-response, variable slope model. The caspase-like activity of the 20S proteasome was determined as described above except that Z-LLEAMC was used as the peptide substrate. For the evaluation of the trypsin-like activity, the SDS was omitted from the assay buffer and Boc-LRR-AMC was used as the peptide substrate.

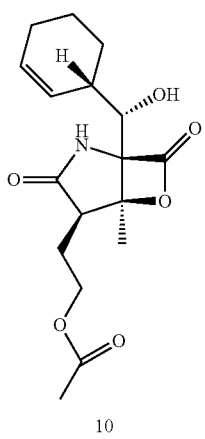

TABLE 2

INHIBITION OF THE CT-L, T-L AND C-L ACTIVITIES OF 20S PROTEASOMES FROM RABBIT (UNLESS OTHERWISE INDICATED) AND β-LACTONE HYDROLYSIS RATES ($T_{1/2}$) FOR SALINOSPORAMIDE A AND ANALOGS

[Structure: bicyclic β-lactone-γ-lactam core with cyclohexenyl-CH(OH)- substituent and R group]

| R | Leaving Group | $T_{1/2}$ (h:min) | Cytotoxicity in RPMI 8226 Average $IC_{50}$ ± SD (nM) | CT-L $IC_{50}$ (nM) | T-L $IC_{50}$ (nM) | C-L $IC_{50}$ (nM) |
|---|---|---|---|---|---|---|
| $CH_2CH_2F$ | | | 875 ± 430 | 10 ± 0.7 | 525 ± 15 | 781 ± 47 |
| $CH_2CH_2Cl$ | Yes | 1:17 ± 5 | 9.8 ± 3 | 2.5 ± 1.2 | 25 ± 4 | 334 ± 31 |
| $CH_2CH_2Br$ | Yes | 1:20 | 7.8 ± 1.4 | 2.6 ± 0.4 | 14 ± 2 | 290 ± 60 |
| $CH_2CH_2I$ | Yes | 1:32 | 6.9 ± 0.9 | 2.8 ± 0.5 | 13 ± 3 | 410 ± 230 |
| $CH_2CH_2OMs$ | Yes | 0:59 | 144 ± 46 | 4.3 ± 0.8 | 65 ± 8 | 873 ± 32 |
| $CH_2CH_2OTs$ | Yes | 1:15 | 27 ± 8.5 | 2.5 ± 0.4 | 9.9 ± 0.2 | 127 ± 5 |
| -CH2CH2-O-SO2-C6H4-tBu | Yes | | 94 ± 18 | 3.2 ± 0.4 | 31 ± 1 | 180 ± 4 |
| -CH2CH2-O-SO2-biphenyl | Yes | | 43 ± 12 | 3.8 ± 0.1 | 15 ± 1 | 101 ± 11 |
| -CH2CH2-O-SO2-C6H4-O-C6H5 | Yes | | 78 ± 25 | 3.2 ± 0.2 | 14 ± 1 | 85 ± 9 |
| $CH_2CH_2ODs$ | Yes | 2:59 | 30 ± 6 | 3.0 ± 0.5 | 12 ± 2.3 | 90 ± 11 |
| $CH_3$ | No | 1:35 | 6,300 ± 4,100 | 7.5 ± 0.6 | 370 ± 44 | 460 ± 49 |
| $CH_2CH_3$ | No | 3:10 | 6,300 ± 3,200 | 26 ± 6.7 | 610 ± 35 | 1200 ± 110 |
| $CH_2CH_2CH_3$ | No | 2:51 | 6,300 ± 3,100 | 24 ± 5 | 1100 ± 200 | 1200 ± 200 |
| $CH_2CH_2OH$ | No | 1:25 | 38,000 ± 4,000 | 14 ± 1.5 | 1200 ± 150 | 1200 ± 57 |
| $CH_2CH_2OC(O)CH_3$ | No | | 20,000 ± 12,000 | 9.1 ± 0.3 | 745 ± 40 | 971 ± 56 |
| -CH2CH2-O-C(O)-biphenyl | No | | 290 ± 108 | 9 ± 2 | 52 ± 5 | 160 ± 9 |

$IC_{50}$ values represent the mean ± standard deviation of 3 or more experiments As shown by the data in Table 2, compounds that bear a bulky group at the R position are potent inhibitors of all three proteolyic subunits (CT-L, C-L and T-L). Notably, compounds with bulky sulfonate ester groups (e.g., dansyl ester or biphenyl ester) or carboxylic ester groups demonstrated markedly lower $IC_{50}$ values for inhibiting the C-L activity. Additionally, the data indicates that the steric bulk of the sulfonate ester and carboxylic ester are accommodated within the three ligand binding sites. As shown by the data, the caspase site tolerates the bulky R group.

The determination of all three rabbit 20S proteolytic activities for additional compounds with sulfonate esters, carboxylic esters and ethers are determined in a similar manner as described above. As with the dansyl and biphenyl analogs, compounds with bulky sulfonate esters are potent inhibitors of all three proteolyic subunits. Similarly, compounds with bulky carboxylic ester and ether groups are also potent inhibitors of the proteolyic subunits. Additionally, the $IC_{50}$ values for inhibiting the C-L activity are lower compared to analogs of Salinosporamide A that have less bulky groups.

Example 12

Dialysis Studies

Rabbit 20S proteasomes were pretreated for 1 hour with the test compounds at their respective $IC_{50}$ values. CT-L activity was measured before and after attempted removal of the compound by dialysis at room temperature.

As shown in FIG. 1, as the size of the $R^1$ group increases, the recovery of the CT-L activity becomes less. These results indicate that as the $R^1$ group increases, the compound demonstrates prolonged inhibition of the 20S proteasome.

Example 13

In Vitro Biology

The test compounds are screened using the National Cancer Institute (NCI) screening panel, which consists of 60 human tumor cell lines that represent leukemia, melanoma and cancers of the lung, colon, brain, ovary, breast, prostate and kidney. A detailed description of the screening procedure can be found at hypertext transfer protocol <http://www.dtp.nci.nih.gov/branches/btb/ivclsp.html>.

In brief, each of the 60 human tumor cell lines are grown in RPMI 1640 medium, supplemented with 5% fetal bovine serum and 2 mM L-glutamine. Cells are plated at their appropriate density in 96-well microtiter plates and are incubated at 37° C., 5% $CO_2$, 95% air and 100% relative humidity. After 24 hours, 100 μL of various 10-fold serial dilutions of the test compound are added to the appropriate wells containing 100 μL of cells, resulting in a final concentration of the test compound ranging from 10 nM to 100 μM. Cells are incubated for an additional 48 hours and a sulforhodamine B protein assay is used to estimate cell viability or growth.

Three dose response parameters are calculated as follows:
$GI_{50}$ indicates the concentration that inhibits growth by 50%.
TGI indicates the concentration that completely inhibits growth.
$LC_{50}$ indicates the concentration that is lethal to 50% of the cells.

Test compounds of Formula (I) are effective against the cell lines of the 60 human tumor cell lines panel.

Example 14

Growth Inhibition of Tumor Cell Lines

B16-F10 (ATCC; CRL-6475), DU 145 (ATCC; HTB-81), HEK293 (ATCC; CRL-1573), HT-29 (ATCC; HTB-38), LoVo (ATCC; CCL-229), MDA-MB-231 (ATCC; HTB-26), MIA PaCa-2 (ATCC; CRL-1420), NCI-H292 (ATCC; CRL-1848), OVCAR-3 (ATCC, HTB-161), PANC-1 (ATCC; CRL-1469), PC-3 (ATCC; CRL-1435), RPMI 8226 (ATCC; CCL-155) and U266 (ATCC; TIB-196) are maintained in appropriate culture media. The cells are cultured in an incubator at 37° C. in 5% $CO_2$ and 95% humidified air.

For cell growth inhibition assays, B16-F10, DU 145, HEK293, HT-29, LoVo, MDA-MB-231, MIA PaCa-2, NCI-H292, OVCAR-3, PANC-1, PC-3, RPMI 8226 and U266 cells are seeded at $1.25 \times 10^3$, $5 \times 10^3$, $1.5 \times 10^4$, $5 \times 10^3$, $5 \times 10^3$, $1 \times 10^4$, $2 \times 10^3$, $4 \times 10^3$, $1 \times 10^4$, $7.5 \times 10^3$, $5 \times 10^3$, $2 \times 10^4$, $2.5 \times 10^4$ cells/well respectively in 90 μl complete media into Corning 3904 black-walled, clear-bottom tissue culture plates. 20 mM stock solutions of the test compound are prepared in 100% DMSO, aliquoted and stored at −80° C. The test compound is serially diluted and added in triplicate to the test wells that result in final concentrations ranging from of 20 μM to 0.2 μM. The plates are returned to the incubator for 48 hours. The final concentration of DMSO is 0.25% in all samples.

Following 48 hours of drug exposure, 10 μl of 0.2 mg/ml resazurin (obtained from Sigma-Aldrich Chemical Co.) in $Mg^{2+}$, $Ca^{2+}$ free phosphate buffered saline are added to each well and the plates are returned to the incubator for 3-6 hours. Since living cells metabolize Resazurin, the fluorescence of the reduction product of Resazurin is measured using a Fusion microplate fluorometer (Packard Bioscience) with $\lambda_{ex}$=535 nm and $\lambda_{em}$=590 nm filters. Resazurin dye in medium without cells is used to determine the background, which was subtracted from the data for all experimental wells. The data is normalized to the average fluorescence of the cells treated with media +0.25% DMSO (100% cell growth) and $EC_{50}$ values (the drug concentration at which 50% of the maximal observed growth inhibition is established) are determined using a standard sigmoidal dose response curve fitting algorithm (generated by XLfit 3.0, ID Business Solutions Ltd or Prism 3.0, GraphPad Software Inc).

Test compounds of Formula (I) are effective in inhibiting the growth B16-F10, DU 145, HEK293, HT-29, LoVo, MDA-MB-231, MIA PaCa-2, NCI-H292, OVCAR-3, PANC-1, PC-3, RPMI 8226 and U266 cells.

Example 15

Multi-Drug Resistant Cell Lines MES-SA/Dx5 and HL-60/MX2

The $EC_{50}$ values of the test compound against the human uterine sarcoma MES-SA cell line and its multidrug-resistant derivative MES-SA/Dx5 are determined to evaluate whether the test compound retains activity against a cell line overexpressing the P-glycoprotein efflux pump. Paclitaxel, a known substrate for the P-glycoprotein pump is included as a control.

The test compound is evaluated against HL-60/MX2, the drug resistant derivative of the human leukemia cell line, HL-60, characterized by having a reduced Topoisomerase II activity and considered to have atypical multidrug resistance. $EC_{50}$ values for growth inhibition are determined for the test compound against the HL-60 and HL-60/MX2. The DNA binding agent Mitoxantrone is included as a control, as HL-60/MX2 cells are reported to be resistant to this chemotherapeutic agent (Harker W. G. et al. 1989).

Test compounds of Formula (I) are effective against the multi drug resistant cell lines MES-SA/Dx5 and HL-60/MX2.

Example 16

Antimicrobial Assays

Minimum inhibitory concentrations (MICs) are determined according to the National Committee for Clinical Laboratory Standards (NCCLS) susceptibility test guideline M7-A5 (Ferraro, M. 2001 Methods for Dilution Antimicrobial Susceptibility Tests for Bacteria that Grow Aerobically; Approved Standard (NCCLS). National Committee for Clinical Laboratory Standards (NCCLS), Villanova, which is incorporated herein by reference in its entirety).

Test compounds of Formula (I) are effective against the microbs tested.

Example 17

Anti-inflammatory Experiment—Inhibition of NF-κB-Mediated Luciferase Activity; HEK293 NF-κB/Luciferase Reporter Cell Line The HEK293 NF-κB/luciferase reporter cell line is a derivative of the human embryonic kidney cell line (ATCC; CRL-1573) and carries a luciferase reporter gene under the regulation of 5× NF-κB binding sites. The reporter cell line is routinely maintained in complete DMEM medium (DMEM plus 10% (v/v) Fetal bovine serum, 2 mM L-glutamine, 10 mM HEPES and Penicillin/Streptomycin at 100 IU/ml and 100 µg/ml, respectively) supplemented with 250 µg/ml G418. When performing the luciferase assay, the DMEM basal medium is replaced with phenol-red free DMEM basal medium and the G418 is omitted. The cells are cultured in an incubator at 37° C. in 5% $CO_2$ and 95% humidified air.

For NF-κB-mediated luciferase assays, HEK293 NF-κB/luciferase cells are seeded at $1.5 \times 10^4$ cells/well in 90 µl phenol-red free DMEM complete medium into Corning 3917 white opaque-bottom tissue culture plates. For test compounds, a 40004 starting dilution is made in 100% DMSO and this dilution is used to generate a 8-point half log dilution series. This dilution series is further diluted 40× in appropriate culture medium and ten µl aliquots are added to the test wells in triplicate resulting in final test concentrations ranging from 1 µM to 320 pM. The plates are returned to the incubator for 1 hour. After 1 hr pretreatment, 10 µl of a 50 ng/ml TNF-α solution, is prepared in the phenol-red free DMEM medium is added, and the plates are incubated for an additional 6 hr. The final concentration of DMSO is 0.25% in all samples.

At the end of the TNF-α stimulation, 100 µl of Steady Lite HTS luciferase reagent (Packard Bioscience) is added to each well and the plates are left undisturbed for 10 min at room temperature before measuring the luciferase activity. The relative luciferase units (RLU) are measured by using a Fusion microplate fluorometer (Packard Bioscience). The $EC_{50}$ values (the drug concentration at which 50% of the maximal relative luciferase unit inhibition is established) are calculated in Prism (GraphPad Software) using a sigmoidal dose response, variable slope model.

Test compounds of Formula (I) are effective in inhibiting NF-κB activity in this cell-based assay.

Inhibition of NF-κB Activation

NF-κB regulates the expression of a large number of genes important in inflammation, apoptosis, tumorigenesis, and autoimmune diseases. In its inactive form, NF-κB complexes with IκB in the cytosol and upon stimulation, IκB is phosphorylated, ubiquitinated and subsequently degraded by the proteasome. The degradation of IκB leads to the activation of NF-κB and its translocation to the nucleus. The effects of test compounds on the activation of NF-κB are evaluated by assessing the NF-κB-mediated luciferase activity in HEK293 NF-κB/Luc cells upon TNF-α stimulation.

Pretreatment of NF-κB/Luc 293 cells with test compounds results in a dose-dependent decrease of luciferase activity upon TNF-α stimulation. The mean $EC_{50}$ values to inhibit NF-κB-mediated luciferase activity are measured which demonstrate that the test compounds are able to inhibit NF-κB activity in this cell-based assay.

Test compounds of Formula (I) are effective in inhibiting NF-κB activation.

It will be understood by those of skill in the art that numerous and various modifications can be made without departing from the spirit of the present disclosure. Therefore, it should be clearly understood that the forms disclosed herein are illustrative only and are not intended to limit the scope of the present disclosure.

What is claimed is:

1. A compound of Formula (I), or pharmaceutically acceptable salt, ester or prodrug thereof:

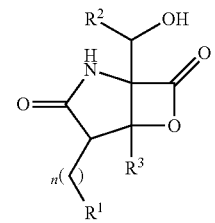

wherein:
$R^1$ is

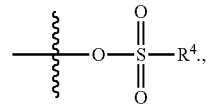

wherein $R^4$ is selected from the group consisting of a mono-substituted, a poly-substituted or an unsubstituted variant of the following residues: aryl, aryl($C_{1-6}$ alkyl), heteroaryl, heteroaryl($C_{1-6}$ alkyl), heterocyclyl, and heterocyclyl($C_{1-6}$ alkyl);

wherein when $R^4$ is a substituted residue, the residue is substituted with one or more groups selected from among alkyl, alkenyl, alkynyl, alkoxy, cycloalkyl, cycloalkenyl, cycloalkynyl, acyl, acylamino, acyloxy, amino, mono-substituted amine, di-substituted amine, alkyl amino, aminoacyl, aminoacyloxy, oxyacylamino, halogen, mono-haloalkyl, di-haloalkyl, trihaloalkyl, mono-haloalkoxy, di-haloalkoxy, tri-haloalkoxy, hydroxy, carboxylalkyl, thioketo, thiol, thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —$SO_2$—H, —$SO_2$—OH, —$SO_2$-alkyl, —$SO_2$-aryl, —$SO_2$-heteroaryl, boronate alkyl, boronic acid, $(OH)_2$B-alkyl, phosphate and phosphate esters, phosphonooxy, phosphonooxyalkyl, azido, azidoalkyl, ammonium, aminoalkyl, salt of an aminoalkyl, carboxyalkyl, a salt of a carboxyalkyl, alkylamino, a salt of an alkylamino, dialkylamino, a salt of a dialkylamino, alkylthio, arylthio, carboxy, cyano, alkoxysulfinyl, thiocyano, boronic acidalkyl, boronic esteralkyl, sulfoalkyl, a salt of a sulfoalkyl, alkoxysulfonylalkyl, sulfooxyalkyl, a salt of a sulfooxyalkyl, alkoxysulfonyloxyalkyl, phosphonooxyalkyl, a salt of a phosphonooxyalkyl, (alkylphosphooxy)alkyl, phosphorylalkyl, a salt of a phosphorylalkyl, (alkylphosphoryl) alkyl, pyridinylalkyl, a salt of a pyridinylalkyl, a salt of a heteroarylalkyl guanidino, a salt of a guanidino, guanidinoalkyl, and

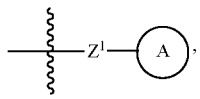

wherein A is selected from the group consisting of a mono-substituted, a poly-substituted or an unsubstituted variant of the following residues: heterocyclyl, aryl and heteroaryl; and $Z^1$ is selected from the group consisting of O, S, N=N, $O(CH_2)_{1-6}$, $S(O)_2N(R^{17})$, $S(O)_2N(R^{17})(CH_2)_{1-6}$, $C(=O)N(R^{17})$, $N(R^{17})C(=O)$, $N(R^{17})C(=O)O$ $(CH_2)_{1-6}$, $N(R^{17})C(=O)O(CH_2)_{1-6}$, $S(O)_2$, $C(=O)$, $(CH_2)_{1-6}C=O$, $O(CH_2)_{1-6}C(=O)$, $(CH_2)_{1-6}N(R^{17})$ $C(=O)$, $CH=CH-C(=O)N(R^{17})$, $CH=CH-C(=O)$, $O(CH_2)_{1-6}I$, $O(CH_2)_{1-6}$ and $N(R^{17a})C(=O)N(R^{17b})$, wherein $R^{17}$, $R^{7a}$ and $R^{17b}$ are independently selected from the group consisting of H, $C_{1-4}$ alkyl, a substituted or unsubstituted benzyl, an allyl, and t-butoxycarbonyl (t-BOC);

$R^2$ is selected from the group consisting of a mono-substituted, a poly-substituted or an unsubstituted variant of the following residues: $C_1$-$C_{12}$ alkyl, $C_2$-$C_{12}$ alkenyl, $C_2$-$C_{12}$ alkynyl, $C_3$-$C_{12}$ cycloalkyl, $C_3$-$C_{12}$ cycloalkenyl, $C_3$-$C_{12}$ cycloalkynyl, $C_3$-$C_{12}$ heterocyclyl, aryl, heteroaryl, arylalkyl, heteroarylalkyl, (cycloalkyl)alkyl, (heterocyclyl)alkyl, arylthio, pyridinylalkyl, a salt of a pyridinylalkyl and a salt of a heteroarylalkyl;

$R^3$ is a mono-substituted, a poly-substituted or an unsubstituted $C_{1-6}$ alkyl or a mono-substituted, a poly-substituted or an unsubstituted $C_{2-6}$ alkenyl;

n is 1, 2 or 3;

provided that when $R^1$ is

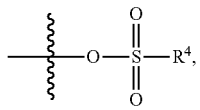

has a molecular weight equal to or greater than 92 g/mol.

2. The compound of claim 1, wherein $R^3$ is an unsubstituted $C_{1-6}$ alkyl.

3. The compound of claim 1, wherein $R^3$ is methyl.

4. The compound of claim 1, wherein n is 2.

5. The compound of claim 1, wherein $R^2$ is selected from the group consisting of a mono-substituted, a poly-substituted or an unsubstituted variant of the following residues: $C_1$-$C_{12}$ alkyl, $C_3$-$C_{12}$ cycloalkyl, $C_3$-$C_{12}$ cycloalkenyl and aryl.

6. The compound of claim 5, wherein $R^2$ is a mono-substituted, a poly-substituted or an unsubstituted $C_1$-$C_{12}$ alkyl.

7. The compound of claim 6, wherein $R^2$ is isopropyl.

8. The compound of claim 5, wherein $R^2$ is a mono-substituted, a poly-substituted or an unsubstituted $C_3$-$C_{12}$ cycloalkyl.

9. The compound of claim 5, wherein $R^2$ is a mono-substituted, a poly-substituted or an unsubstituted $C_3$-$C_{12}$ cycloalkenyl.

10. The compound of claim 9, wherein $R^2$ is a mono-substituted, a poly-substituted or an unsubstituted cyclohexenyl.

11. The compound of claim 5, wherein $R^2$ is a mono-substituted, a poly-substituted or an unsubstituted aryl.

12. The compound of claim 11, wherein $R^2$ is a mono-substituted, a poly-substituted or an unsubstituted phenyl.

13. The compound of claim 1, wherein $R^4$ is selected from the group consisting of a mono-substituted, a poly-substituted or an unsubstituted variant of the following residues: aryl, heteroaryl and heterocyclyl; wherein when $R^4$ is a substituted residue, the residue is substituted with one or more groups selected from among alkyl, alkoxy, acyl, acylamino, acyloxy, amino, mono-substituted amine, di-substituted amine, halogen, mono-haloalkyl, di-haloalkyl, tri-haloalkyl, mono-haloalkoxy, di-haloalkoxy, tri-haloalkoxy, hydroxy, carboxyalkyl, thioketo, thiol, thioalkoxy, alkoxyamino, nitro, —SO-alkyl, $SO_2$—H, —$SO_2$—OH, —$SO_2$-alkyl, azido, ammonium, aminoalkyl, carboxyalkyl, alkylamino, dialkylamino, alkylthio, carboxy, cyano and thiocyano.

14. The compound of claim 1 having the structure:

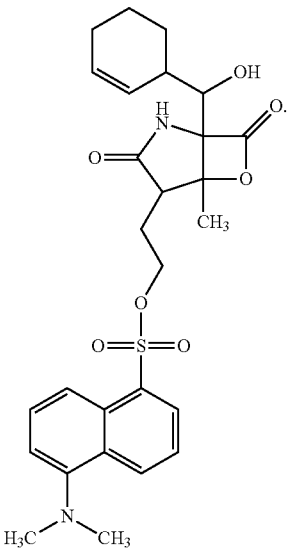 [SMILES: CN(C)c1cccc2c(S(=O)(=O)OCCC3C(=O)NC4(C(O)C5C=CCCC5)C(=O)OC34C)cccc12]

15. The compound of claim 1 having the structure:

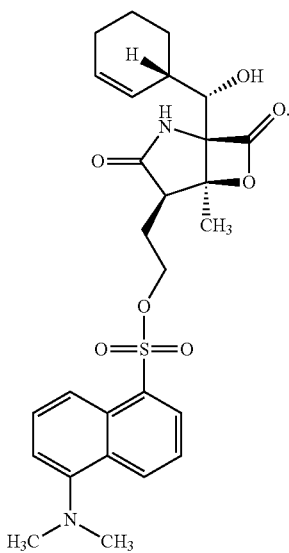

16. A method for treating, alleviating or diagnosing a neoplastic disease comprising administering to a subject a therapeutically effective amount of a compound of claim 1, or pharmaceutically acceptable salt, ester or prodrug thereof, wherein the neoplastic disease is a cancer selected from the group consisting of breast cancer, sarcoma, leukemia, ovarian cancer, bladder cancer, prostate cancer, colon cancer, rectal cancer, stomach cancer, lung cancer, lymphoma, multiple myeloma, pancreatic cancer, kidney cancer, endocrine cancer, melanoma, skin cancer, angiosarcoma, sinus cancer, esophageal cancer, uretal cancer, liver cancer, angioma, central nervous system (CNS) cancer, Mantle cell lymphoma, low IgM secreting lymphoma, Burkitt's lymphoma, B-NHL lymphoma and Waldenstrom's Macroglobulimemia.

17. The method of claim 16, wherein the compound has a structure selected from:

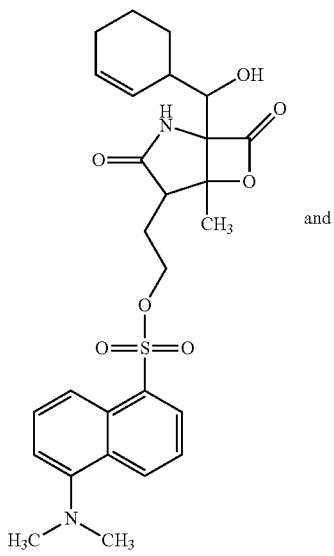

and

-continued

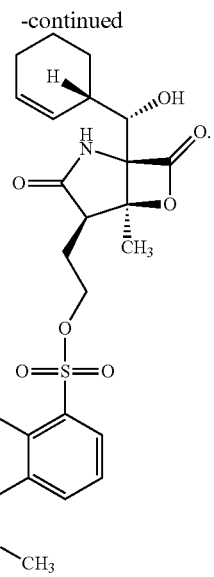

18. A method for inhibiting NF-κB activity comprising administering to a subject a therapeutically effective amount of a compound of claim 1, or pharmaceutically acceptable salt, ester or prodrug thereof.

19. A method for inhibiting proteasome activity comprising administering to a subject a therapeutically effective amount of a compound of claim 1, or pharmaceutically acceptable salt, ester or prodrug thereof.

20. A method for inhibiting the growth of a cancer cell comprising contacting the cancer cell with a therapeutically effective amount of a compound of claim 1, or pharmaceutically acceptable salt, ester or prodrug thereof.

21. The method of claim 20, wherein the cancer cell is selected from the group consisting of breast cancer cell, sarcoma cell, leukemia cell, ovarian cancer cell, bladder cancer cell, prostate cancer cell, colon cancer cell, rectal cancer cell, stomach cancer cell, lung cancer cell, lymphoma cell, multiple myeloma cell, pancreatic cancer cell, kidney cancer cell, endocrine cancer cell, melanoma cell, skin cancer cell, angiosarcoma cell, sinus cancer cell, esophageal cancer cell, uretal cancer cell, liver cancer cell, angioma cell, central nervous system (CNS) cancer cell, Mantle cell lymphoma cell, low IgM secreting lymphoma cell, Burkitt's lymphoma cell, B-NHL lymphoma cell and Waldenstrom's Macroglobulimemia cell.

* * * * *